United States Patent
Wailes et al.

(10) Patent No.: US 12,227,495 B2
(45) Date of Patent: Feb. 18, 2025

(54) HERBICIDAL COMPOUNDS

(71) Applicant: SYNGENTA CROP PROTECTION AG, Basel (CH)

(72) Inventors: Jeffrey Steven Wailes, Bracknell (GB); Janice Black, Bracknell (GB); James Alan Morris, Bracknell (GB); Emma Briggs, Bracknell (GB); Joseph Andrew Tate, Bracknell (GB); Mary Bernadette Aspinall, Bracknell (GB); Sean Ng, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 753 days.

(21) Appl. No.: 17/290,869

(22) PCT Filed: Nov. 1, 2019

(86) PCT No.: PCT/EP2019/079971
§ 371 (c)(1),
(2) Date: May 3, 2021

(87) PCT Pub. No.: WO2020/094524
PCT Pub. Date: May 14, 2020

(65) Prior Publication Data
US 2021/0387976 A1   Dec. 16, 2021

(30) Foreign Application Priority Data

Nov. 5, 2018 (GB) ...................... 1818013

(51) Int. Cl.
| | | |
|---|---|---|
| G01N 33/49 | (2006.01) |
| A01N 25/32 | (2006.01) |
| A01N 43/40 | (2006.01) |
| A01N 43/50 | (2006.01) |
| A01N 43/56 | (2006.01) |
| A01N 43/78 | (2006.01) |
| A01N 43/80 | (2006.01) |
| A01N 43/82 | (2006.01) |
| A01P 13/00 | (2006.01) |
| A61P 1/08 | (2006.01) |
| A61P 39/06 | (2006.01) |
| C07D 401/12 | (2006.01) |
| C07D 409/12 | (2006.01) |
| C07D 413/12 | (2006.01) |
| C07D 417/12 | (2006.01) |
| G01N 33/52 | (2006.01) |
| G01N 33/80 | (2006.01) |
| A61K 33/243 | (2019.01) |

(52) U.S. Cl.
CPC ........... *C07D 413/12* (2013.01); *A01N 25/32* (2013.01); *A01N 43/40* (2013.01); *A01N 43/50* (2013.01); *A01N 43/56* (2013.01); *A01N 43/78* (2013.01); *A01N 43/80* (2013.01); *A01N 43/82* (2013.01); *A01P 13/00* (2021.08); *C07D 401/12* (2013.01); *C07D 409/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 628,310 | A | 7/1899 | Goldner |
| 6,268,310 | B1 | 7/2001 | Ueda et al. |
| 2009/0163545 | A1 | 6/2009 | Goldfarb |
| 2009/0221547 | A1 | 9/2009 | Gao et al. |

FOREIGN PATENT DOCUMENTS

| | | |
|---|---|---|
| EP | 0776894 A1 | 6/1997 |
| WO | 9840379 A1 | 9/1998 |
| WO | 2015089003 A1 | 6/2015 |
| WO | 2015108779 A1 | 7/2015 |

OTHER PUBLICATIONS

Mitsos, C. Isosteres in Medicinal Chemistry. Feb. 1, 2006. (Year: 2006).*
Wermuth, C. Med. Chem. Commun., 2011, 2, 935-941. (Year: 2011).*
Wu, Yimin et al., "Rhodium-catalyzed ortho-heteroarylation of phenols: directing group-enabled switching of the electronic bias for heteroaromatic coupling partner," Chemical Science, vol. 9, No. 33, Jan. 1, 2018, pp. 6878-6882.
Database Chemcats, Chemical Abstracts Service, Columbus Ohio, Sep. 25, 2018, Atomx Chemicals Product List, RN 1211770-65-8.
Written Opinion of the International Searching Authority and International Search Report for PCT/EP2019/079971 mailed Mar. 9, 2020.

(Continued)

*Primary Examiner* — Mina Haghighatian
*Assistant Examiner* — Janice Y Silverman
(74) *Attorney, Agent, or Firm* — BakerHostetler; Toni-Junell Herbert

(57) ABSTRACT

The present invention relates to compounds of Formula (I) or an agronomically acceptable salt of said compounds wherein Q, $R^1$, $R^2$, n and m are as defined herein. The invention further relates to herbicidal compositions which comprise a compound of Formula (I) and to the use of compounds of Formula (I) for controlling weeds, in particular in crops of useful plants.

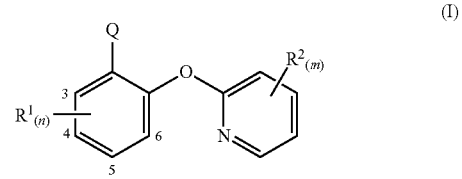

13 Claims, No Drawings

(56) References Cited

OTHER PUBLICATIONS

Database PubChem Compound, NCBI, created Jul. 19, 2005, "3-Chloro-2-[2-(1,3,4-oxadiazol-2-yl) phenoxy]-5-(trifluormethyl) pyridine CL14H7C1F3N3O2," XP055666746, Database accession No. 2766749, last modified May 1, 2021, accessed May 3, 2021.

\* cited by examiner

HERBICIDAL COMPOUNDS

CROSS-REFERENCE TO RELATED APPLICATIONS

This application is a 371 National Stage application of International Application No. PCT/EP2019/079971 filed Nov. 1, 2019, which claims priority to GB 1818013.3, filed Nov. 5, 2018, the entire contents of these applications are hereby incorporated by reference.

The present invention relates to novel herbicidal compounds, to processes for their preparation, to herbicidal compositions which comprise the novel compounds, and to their use for controlling weeds, in particular in crops of useful plants, or for inhibiting plant growth.

Herbicidal heteroaryl-substituted phenoxypyrimidines are disclosed in, for example, WO94/17059, WO2015/089003 and WO2015/108779. The present invention relates to novel herbicidal phenoxypyridine compounds which show improved properties compared to the known pyrimidine compounds—especially improved crop selectivity.

Thus, according to the present invention there is provided a compound of Formula (I):

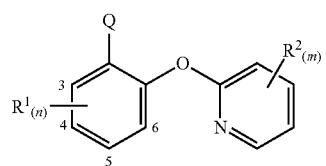

(I)

or an agronomically acceptable salt thereof,
wherein
Q is a 5-membered aromatic heterocyclic ring which is optionally substituted by 1 or 2 $R^3$ substituents independently selected from the group consisting of $C_1$-$C_4$alkyl, $C_2$-$C_4$alkenyl, $C_2$-$C_4$alkynyl, cyclopropyl, $C_1$-$C_4$haloalkyl, $C_1$-$C_2$alkoxy-, $C_1$-$C_2$haloalkoxy-, halogen, —C(O)$C_1$-$C_4$alkyl, $NO_2$, —$CH_2CN$, —CN and —S(O)$_p$$C_1$-$C_4$alkyl;
each $R^1$ is independently selected from the group consisting of halogen, —CN, nitro, $C_1$-$C_4$alkyl, $C_2$-$C_4$alkenyl, $C_2$-$C_4$alkynyl, $C_1$-$C_4$haloalkyl, $C_1$-$C_4$alkoxy-, $C_1$-$C_4$haloalkoxy- and —S(O)$_p$$C_1$-$C_4$alkyl;
each $R^2$ is independently selected from the group consisting of halogen, —CN, $NO_2$, $C_1$-$C_4$alkyl, $C_1$-$C_4$haloalkyl, $C_3$-$C_6$cycloalkyl, $C_2$-$C_4$alkenyl, $C_2$-$C_4$alkynyl, —S(O)$_p$$C_1$-$C_4$alkyl, $C_1$-$C_4$alkoxy, —C(O)$C_1$-$C_4$alkyl, —C(O)$C_1$-$C_4$alkyl and $C_1$-$C_4$haloalkoxy;
m=0, 1 or 2;
n=0, 1 or 2; and
p=0, 1 or 2
with the proviso that Q is not 1,3,4-oxadiazol-2-yl or a C-linked tetrazolyl and wherein if Q is 2-thienyl or 2-furyl then said 2-thienyl or 2-furyl is substituted by 1 or 2 $R^3$ independently selected from the group consisting of $C_1$-$C_2$haloalkyl, halogen and —CN.

$C_1$-$C_4$alkyl- includes, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu). $C_1$-$C_2$alkyl is methyl (Me, $CH_3$) or ethyl (Et, $C_2H_5$).

Halogen (or halo) includes, for example, fluorine, chlorine, bromine or iodine. The same correspondingly applies to halogen in the context of other definitions, such as haloalkyl.

$C_1$-$C_4$haloalkyl- includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoropropyl and 2,2,2-trichloroethyl, heptafluoro-n-propyl and perfluoro-n-hexyl. $C_1$-$C_2$haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, or 1,1-difluoro-2,2,2-trichloroethyl.

$C_1$-$C_2$alkoxy is methoxy or ethoxy.

$C_1$-$C_2$haloalkoxy- includes, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_3$-$C_6$cycloalkyl- includes cyclopropyl (c-propyl (c-Pr)), cyclobutyl (c-butyl (c-Bu)), cyclopentyl (c-pentyl) and cyclohexyl (c-hexyl).

$C_2$-$C_4$alkenyl- includes, for example, —CH=$CH_2$ (vinyl) and —$CH_2$—CH=$CH_2$ (allyl).

$C_2$-$C_4$alkynyl- includes, for example, —C≡CH (ethynyl) and —$CH_2$—C≡CH (propargyl).

$C_1$-$C_4$alkyl-S— (alkylthio) includes, for example, methylthio, ethylthio, propylthio, isopropylthio, n-butylthio, isobutylthio, sec-butylthio or tert-butylthio, preferably methylthio or ethylthio.

$C_1$-$C_4$alkyl-S(O)— (alkylsulfinyl) includes, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_4$alkyl-S(O)$_2$— (alkylsulfonyl) includes, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In one embodiment of the present invention there is provided a compound of Formula (I) wherein n is 0. In another embodiment of the present invention there is provided a compound of Formula (I) wherein n is 1 or 2 and each $R^1$ is independently selected from the group consisting of halogen, —CN, nitro, $C_1$-$C_2$alkyl, $C_1$-$C_2$haloalkyl, $C_1$-$C_2$alkoxy and $C_1$-$C_2$haloalkoxy-. In a preferred embodiment of the present invention there is provided a compound of Formula (I) wherein n is 1 and $R^1$ is halogen (especially fluoro, chloro or bromo) or CN. In an especially preferred embodiment of the present invention there is provided a compound of Formula (I) wherein n is 1 and $R^1$ is fluoro, especially 3-fluoro.

In another embodiment of the present invention there is provided a compound of Formula (I), wherein m=0. In another embodiment of the present invention there is provided a compound of Formula (I) wherein m is 1 or 2. In a preferred embodiment of the present invention there is provided a compound of Formula (I) wherein m is 1 or 2 and each $R^2$ is independently selected from the group consisting of halogen (especially fluoro, chloro or bromo), nitro, —CN and $C_1$-$C_4$haloalkyl (especially trifluoromethyl). In a particularly preferred embodiment of the present invention there is provided a compound of Formula (I) wherein m is 1 or 2 and each $R^2$ is independently selected from the group consisting of fluoro, chloro, bromo, nitro, —CN and trifluoromethyl.

In another embodiment of the present invention there is provided a compound of Formula (I) wherein Q is selected from the group consisting of:
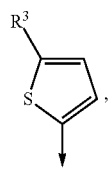 (Q1)
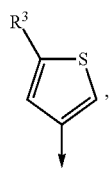 (Q2)
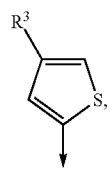 (Q3)
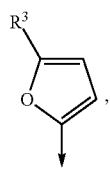 (Q4)
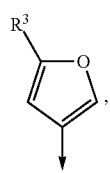 (Q5)
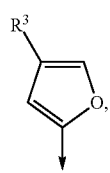 (Q6)
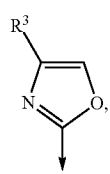 (Q7)
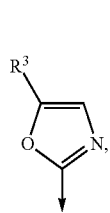 (Q8)
-continued
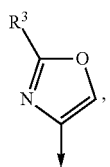 (Q9)
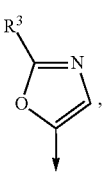 (Q10)
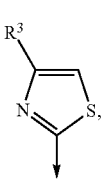 (Q11)
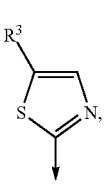 (Q12)
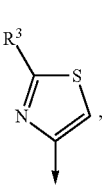 (Q13)
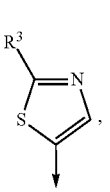 (Q14)
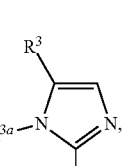 (Q15)
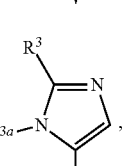 (Q16)
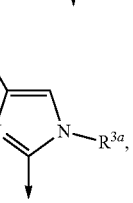 (Q17)

-continued
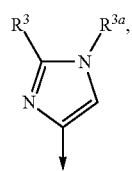 (Q18)
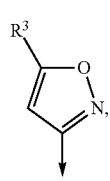 (Q19)
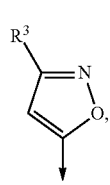 (Q20)
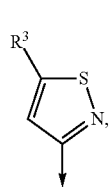 (Q21)
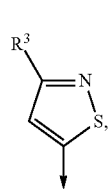 (Q22)
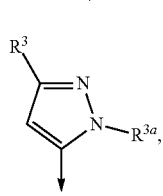 (Q23)
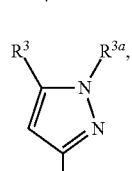 (Q24)
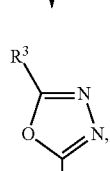 (Q25)
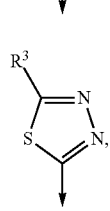 (Q26)
-continued
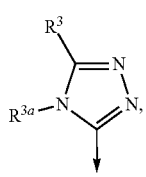 (Q27)
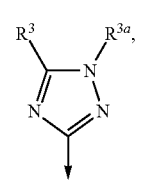 (Q28)
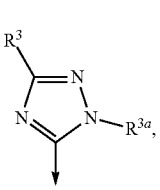 (Q29)
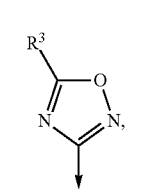 (Q30)
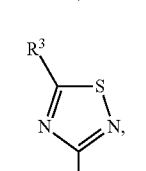 (Q31)
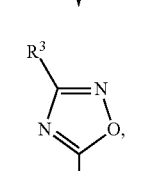 (Q32)
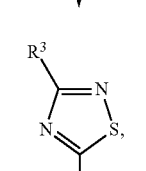 (Q33)
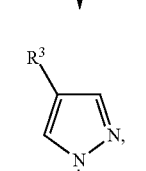 (Q34)
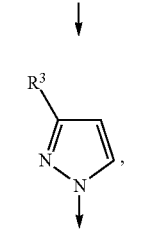 (Q35)

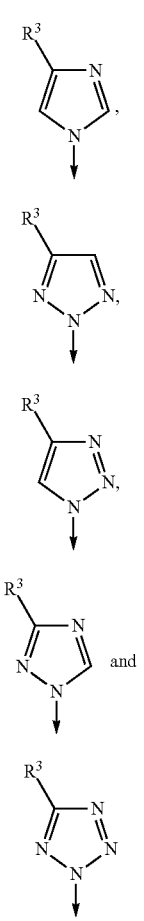

(Q36)
(Q37)
(Q38)
(Q39) and
(Q40)

wherein R³ is selected from the group consisting of hydrogen, $C_1$-$C_4$alkyl, $C_2$-$C_4$alkenyl, $C_2$-$C_4$alkynyl, cyclopropyl, $C_1$-$C_2$haloalkyl, $C_1$-$C_2$alkoxy-, $C_1$-$C_2$haloalkoxy-, halogen, —C(O)$C_1$-$C_4$alkyl, $NO_2$, —$CH_2CN$, —CN and —S(O)$_p$$C_1$-$C_4$alkyl; and $R^{3a}$ is hydrogen or $C_1$-$C_2$alkyl.

In a preferred embodiment of the present invention, Q is Q19, Q20 or Q34.

In another embodiment of the present invention there is provided a compound of Formula (I), wherein R³ is $C_1$-$C_2$haloalkyl. In a more preferred embodiment R³ is difluoromethyl or trifluoromethyl.

Thus, in a preferred embodiment of the present invention the compound of Formula (I) is a compound of Formula (Ia):

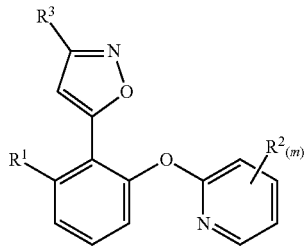

(Ia)

wherein R¹ is hydrogen, fluoro, chloro, bromo or CN and R², m and R³ are as defined previously.

In another preferred embodiment of the present invention the compound of Formula (I) is a compound of Formula (Ib):

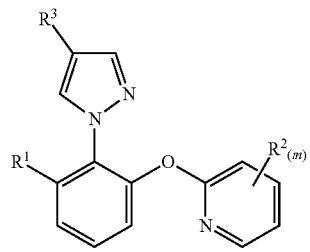

(Ib)

wherein R¹ is hydrogen, fluoro, chloro, bromo or CN and R², m and R³ are as defined previously.

In another preferred embodiment of the present invention the compound of Formula (I) is a compound of Formula (Ic):

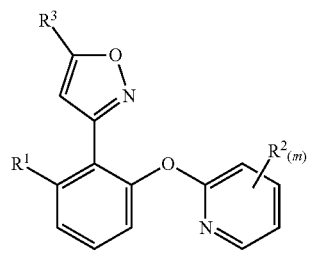

(Ic)

wherein R¹ is hydrogen, fluoro, chloro, bromo or CN and R², m and R³ are as defined previously.

Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

The present invention also provides agronomically acceptable salts of compounds of Formula (I). Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred.

The compounds of Formula (I) according to the invention can be used as herbicides by themselves, but they are generally formulated into herbicidal compositions using formulation adjuvants, such as carriers, solvents and surface-active agents (SAA). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types. These include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a soluble powder (SP), a wettable powder (WP) and a soluble granule (SG). The formulation type chosen in any instance will depend upon the particular purpose envisaged and the physical, chemical and biological properties of the compound of Formula (I).

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SAAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SAAs, to produce spontaneously a thermodynamically stable isotropic liquid formulation. A compound of Formula (I) is present initially in either the water or the solvent/SAA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SAAs), spray additives based on oils, for example certain mineral oils or natural plant oils (such as soy bean and rape seed oil), modified plant oils such as methylated rape seed oil (MRSO), and blends of these with other bio-enhancing adjuvants (ingredients which may aid or modify the action of a compound of Formula (I).

Wetting agents, dispersing agents and emulsifying agents may be SAAs of the cationic, anionic, amphoteric or non-ionic type.

Suitable SAAs of the cationic type include quaternary ammonium compounds (for example cetyltrimethyl ammonium bromide), imidazolines and amine salts.

Suitable anionic SAAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates, lignosulphonates and phosphates/sulphates of tristyrylphenols.

Suitable SAAs of the amphoteric type include betaines, propionates and glycinates.

Suitable SAAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); lecithins and sorbitans and esters thereof, alkyl polyglycosides and tristyrylphenols.

Suitable suspending agents include hydrophilic colloids (such as polysaccharides, polyvinylpyrrolidone or sodium carboxymethylcellulose) and swelling clays (such as bentonite or attapulgite).

The herbicidal compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, bensulfuron (including bensulfuron-methyl), bentazone, bicyclopyrone, bilanafos, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chlorotoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, diquat dibromide, diuron, ethalfluralin, ethofumesate, fenoxaprop (including fenoxaprop-P-ethyl), fenoxasulfone, fenquinotrione, fentrazamide, flazasulfuron, florasulam, florpyrauxifen (including florpyraxifen-benzyl), fluazifop (including fluazifop-P-butyl), flucarbazone (including flucarbazone-sodium), flufenacet, flumetsulam, flumioxazin, flupyrsulfuron (including flupyrsulfuron-methyl-sodium), fluroxypyr (including fluroxypyr-meptyl), fomesafen, foramsulfuron, glufosinate (including the ammonium salt thereof), glyphosate (including the diammonium, isopropylammonium and potassium salts thereof), halauxifen (including halauxifen-methyl), haloxyfop (including haloxyfop-methyl), hexazinone, hydantocidin, imazamox, imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, propanil, propaquizafop, propyrisulfuron, propyzamide, prosulfocarb, prosulfuron, pyraclonil, pyraflufen (including pyraflufen-ethyl), pyrasulfotole, pyridate, pyriftalid, pyrimisulfan, pyroxasulfone, pyroxsulam, quinclorac, quinmerac, quizalofop (including quizalofop-P-ethyl and quizalofop-P-tefuryl), rimsulfuron, saflufenacil, sethoxydim, simazine, S-metolachlor, sulfentrazone, sulfosulfuron, tebuthiuron, tefuryltrione, tembotrione, terbuthylazine, terbutryn, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl]imidazolidin-2-one, (4R)1-(5-tert-butylisoxazol-3-yl)-4-ethoxy-5-hydroxy-3-methyl-imidazolidin-2-one, 3-[2-(3,4-dimethoxyphenyl)-6-methyl-3-oxo-pyridazine-4-carbonyl]bicyclo[3.2.1]octane-2,4-dione, 2-[2-(3,4-dimethoxyphenyl)-6-methyl-3-oxo-pyridazine-4-carbonyl]-5-methyl-cyclohexane-1,3-dione, 2-[2-(3,4-dimethoxyphenyl)-6-methyl-3-oxo-pyridazine-4-carbonyl]cyclohexane-1,3-dione, 2-[2-(3,4-dimethoxyphenyl)-6-methyl-3-oxo-pyridazine-4-carbonyl]-5,5-dimethyl-cyclohexane-1,3-dione, 6-[2-(3,4-dimethoxyphenyl)-6-methyl-3-oxo-pyridazine-4-carbonyl]-2,2,4,4-tetramethyl-cyclohexane-1,3,5-trione, 2-[2-(3,4-dimethoxyphenyl)-6-methyl-3-oxo-pyridazine-4-carbonyl]-5-ethyl-cyclohexane-1,3-dione, 2-[2-(3,4-dimethoxyphenyl)-6-methyl-3-oxo-pyridazine-4-carbonyl]-4,4,6,6-tetramethyl-cyclohexane-1,3-dione, 2-[6-cyclopropyl-2-(3,4-dimethoxyphenyl)-3-oxo-pyridazine-4-carbonyl]-5-methyl-cyclohexane-1,3-dione, 3-[6-cyclopropyl-2-(3,4-dimethoxyphenyl)-3-oxo-pyridazine-4-carbonyl]bicyclo[3.2.1]octane-2,4-dione, 2-[6-cyclopropyl-2-(3,4-dimethoxyphenyl)-3-oxopyridazine-4-carbonyl]-5,5-dimethyl-cyclohexane-1,3-dione, 6-[6-cyclopropyl-2-(3,4-dimethoxyphenyl)-3-oxo-pyridazine-4-carbonyl]-2,2,4,4-tetramethyl-cyclohexane-1,3,5-trione, 2-[6-cyclopropyl-2-(3,4-dimethoxyphenyl)-3-oxo-pyridazine-4-carbonyl]cyclohexane-1,3-dione, 4-[2-(3,4-dimethoxyphenyl)-6-methyl-3-oxo-pyridazine-4-carbonyl]-2,2,6,6-tetramethyl-tetrahydropyran-3,5-dione and 4-[6-cyclopropyl-2-(3,4-dimethoxyphenyl)-3-oxo-pyridazine-4-carbonyl]-2,2,6,6-tetramethyl-tetrahydropyran-3,5-dione.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula (I) with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil.

Particularly preferred are mixtures of a compound of Formula (I) with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048.

Preferably the mixing ratio of compound of Formula (I) to safener is from 100:1 to 1:10, especially from 20:1 to 1:1.

The present invention still further provides a method of controlling weeds at a locus said method comprising application to the locus of a weed controlling amount of a composition comprising a compound of Formula (I). Moreover, the present invention may further provide a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. It is noted that the compounds of the present invention show a much improved selectivity compared to know, structurally similar compounds. Generally the plants to be controlled are unwanted plants (weeds). 'Locus' means the area in which the plants are growing or will grow. The application may be applied to the locus pre-emergence and/or postemergence of the crop plant. Some crop plants may be inherently tolerant to herbicidal effects of compounds of Formula (I). Preferred crop plants include maize, wheat, barley and rice.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2500 g/ha, especially from 25 to 1000 g/ha, more especially from 25 to 250 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to other herbicides or classes of herbicides (e.g. ALS-, GS-, EPSPS-, PPO-, HPPD-, -PDS and ACCase-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*.

In a further aspect of the present invention there is provided the use of a compound of Formula (I) as defined herein as a herbicide.

The compounds of the present invention can be prepared according to the following schemes.

Processes for Preparation of Compounds of Formula (I)

Processes for preparation of compounds, e.g. a compound of formula (I) (which optionally can be an agrochemically acceptable salt thereof), are now described, and form further aspects of the present invention.

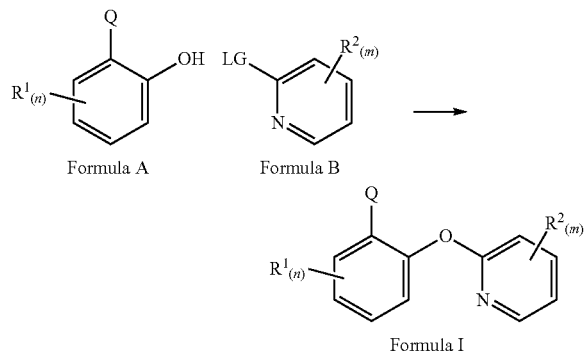

Formula A   Formula B

Formula I

A compound of Formula I may be prepared from a compound of Formula A by reaction with a compound of Formula B (where LG represents a suitable leaving group such as Br, Cl, F or $OSC_2Me$) optionally in the presence of a suitable base and in a suitable solvent at a suitable reaction temperature. Suitable bases may include $K_2CO_3$ or $Cs_2CO_3$. Suitable solvents include DMF. Suitable reaction temperatures are between 20° C. and 120° C. Compounds of Formula B are commercially available or may be prepared by methods known in the literature.

Formula C → Formula A

Alternatively, a compound of Formula A may be prepared from a compound of Formula C (where PG represents a suitable protecting group, such as Me or Ac) via a deprotection reaction. Suitable conditions for deprotection when PG=Me include the use of $BBr_3$ in a suitable solvent, such as DCM. Suitable condition for deprotection when PG=Ac include the use of $K_2CO_3$ or $NH_4OAC$ in a suitable solvent, such as MeOH or $MeOH/H_2O$.

Formula D   Formula E

Formula C

A compound of Formula C may be prepared from a compound of Formula D (where X represents a suitable halogen such as F, Cl, Br or I or a suitable pseudohalogen such as OTf) via reaction with a compound of Formula E (where Y represents a suitable coupling partner functional group such as $-B(OR)_2$ or $-SnR_3$) in the presence of a suitable catalyst/ligand combination, optionally in the presence of a suitable base and in a suitable solvent. Suitable catalysts may include bis-triphenylphosphine-palladium(II) chloride. Suitable bases may include $Cs_2CO_3$. Suitable solvents may include 1,4-dioxane or DMF. Compounds of Formula D and of Formula E are commercially available or may be prepared by methods known in the literature.

Formula F   Formula G

Formula C

In an alternative approach, a compound of Formula C may be prepared from a compound of Formula F (where Y represents a suitable coupling partner functional group such as $-B(OR)_2$ or $-SnR_3$) and a compound of Formula G (where Q is a C-linked heterocycle such as Q1 and Q2 and where X represents a suitable halogen such as F, Cl, Br or I or a suitable pseudohalogen such as OTf) in the presence of a suitable catalyst/ligand combination, optionally in the presence of a suitable base and in a suitable solvent. Suitable catalysts may include tetrakis(triphenylphosphine) palladium. Suitable bases may include $K_2CO_3$. Suitable solvents may include $DCM/H_2O$. Compounds of Formula F and of Formula G are commercially available or may be prepared by methods known in the literature.

Formula H   Formula E

Formula I

In an alternative approach, a compound of Formula I may be prepared from a compound of Formula H (where X represents a suitable halogen such as F, Cl, Br or I or a suitable pseudohalogen such as OTf) and a compound of Formula E (where Y represents a suitable coupling partner functional group such as $-B(OR)_2$ or $-SnR_3$) in the presence of a suitable catalyst/ligand combination, optionally in the presence of a suitable base and in a suitable solvent. Suitable catalysts may include bis-triphenylphosphine-palladium(II) chloride. Suitable bases may include Cs$_2$CO$_3$. Suitable solvents may include 1,4-dioxane or DMF. Compounds of Formula E are commercially available or may be prepared by methods known in the literature.

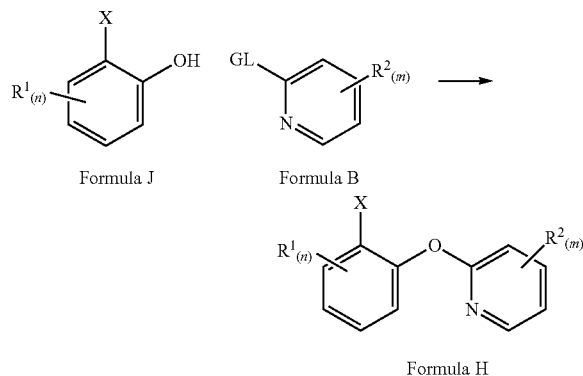

Formula J        Formula B

Formula H

A compound of Formula H may be prepared from a compound of Formula J and a compound of Formula B (where LG represents a suitable leaving group such as Br, Cl, F or OSO$_2$Me) in the presence of a suitable base and in a suitable solvent. Suitable bases may include Cs$_2$CO$_3$, K$_2$CO$_3$ or NaH. Suitable solvents may include DMF or DMSO. Compounds of Formula J and of Formula B are commercially available or may be prepared by methods known in the literature.

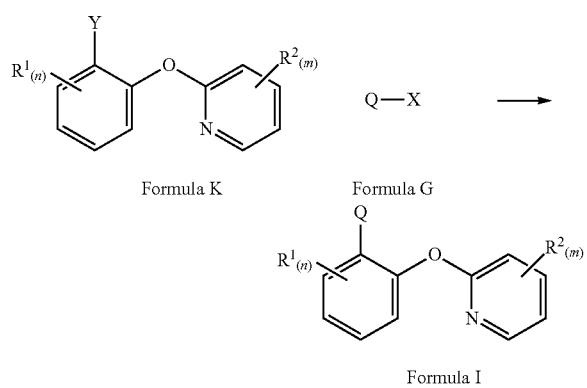

Formula K        Formula G

Formula I

In a further alternative approach, a compound of Formula I may be prepared from a compound of Formula K (where Y represents a suitable coupling partner functional group such as —B(OR)$_2$ or —SnR$_3$) and a compound of Formula G (where Q is a C-linked heterocycle and where X represents a suitable halogen such as F, Cl, Br or I or a suitable pseudohalogen such as OTf) in the presence of a suitable catalyst/ligand combination, optionally in the presence of a suitable base and in a suitable solvent. Suitable catalysts may include tetrakis(triphenylphosphine) palladium. Suitable bases may include K$_2$CO$_3$. Suitable solvents may include DCM/H$_2$O. Compounds of Formula G are commercially available or may be prepared by methods known in the literature.

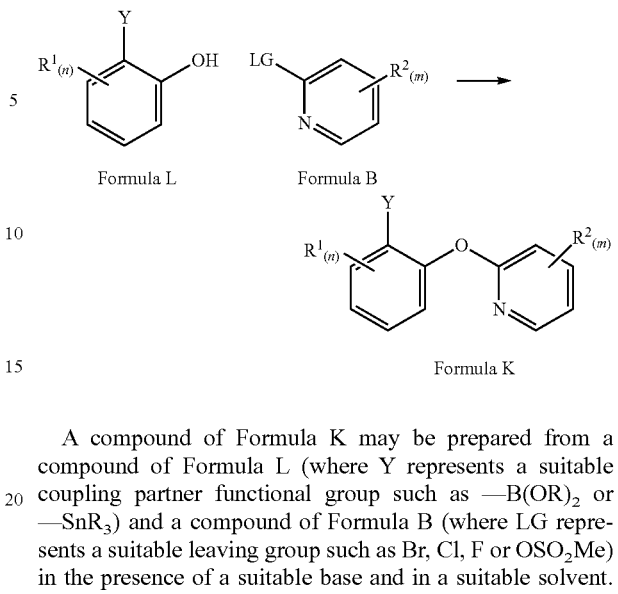

Formula L        Formula B

Formula K

A compound of Formula K may be prepared from a compound of Formula L (where Y represents a suitable coupling partner functional group such as —B(OR)$_2$ or —SnR$_3$) and a compound of Formula B (where LG represents a suitable leaving group such as Br, Cl, F or OSO$_2$Me) in the presence of a suitable base and in a suitable solvent. Suitable bases may include Cs$_2$CO$_3$, K$_2$CO$_3$ or NaH. Suitable solvents may include DMF or DMSO. Compounds of Formula L and of Formula B are commercially available or may be prepared by methods known in the literature.

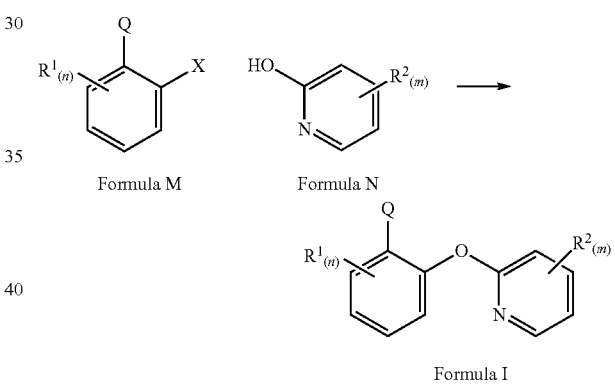

Formula M        Formula N

Formula I

In a yet further alternative approach, a compound of Formula I may be prepared from a compound of Formula M (where X represents a suitable halogen such as F, Cl, Br or I or a suitable pseudohalogen such as OTf) and a compound of Formula N in the presence of a suitable catalyst, optionally in the presence of a suitable base and in a suitable solvent. Suitable catalysts may include copper (I) iodide. Suitable bases may include K$_2$CO$_3$. Suitable solvents may include DMSO. Compounds of Formula M and of Formula N are commercially available or may be prepared by methods known in the literature.

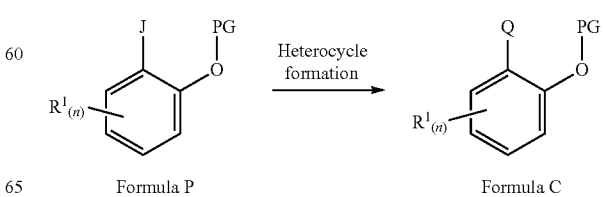

Formula P        Formula C

In a still further alternative approach, a compound of Formula C may be prepared from a compound of Formula P (where J is an alkene, alkyne, oxime, ketone, carboxylic acid, ester, amide, hydrazine, azide or amine) using methods of heterocycle formation known in the literature.

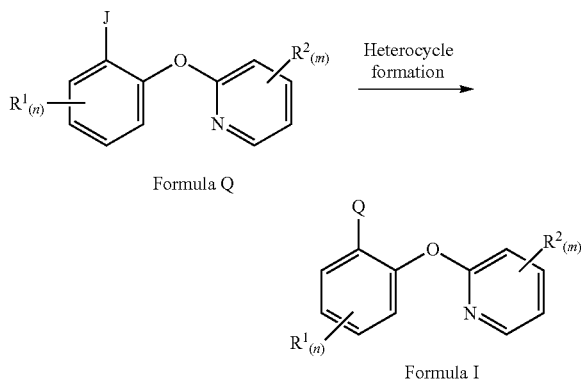

Similarly, a compound of Formula I may be prepared from a compound of formula Q (where J is an alkene, alkyne, oxime, ketone, carboxylic acid, ester, amide, hydrazine, azide or amine) using methods of heterocycle formation known in the literature.

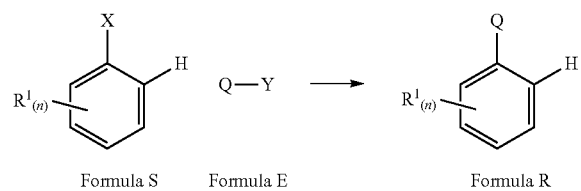

In a further approach, a compound of Formula Ci (a compound of Formula C where Q is a suitable ortho-directing heterocycle such as Q9, Q11, Q12, Q34 or Q35) may be prepared from a compound of Formula R in the presence of a suitable catalyst, a suitable oxidant and a suitable nucleophile. Suitable catalysts may include Pd(OAc)$_2$. Suitable oxidants may include (diacetoxyiodo)benzene. Suitable nucleophiles may include acetic acid.

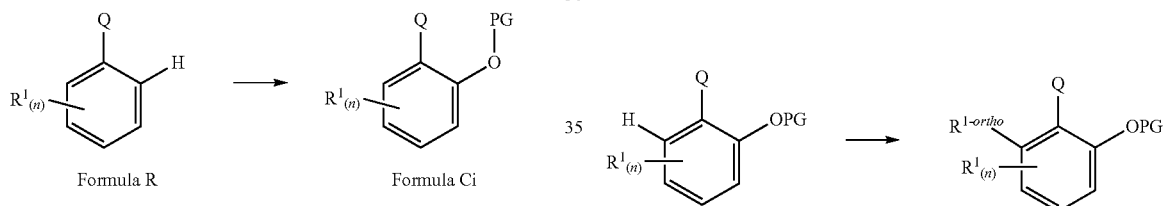

A compound of Formula R may be prepared from a compound of Formula S (where X represents a suitable halogen such as Cl, Br or I or a suitable pseudohalogen such as OTf) via reaction with a compound of Formula E (where Y represents a suitable coupling partner functional group such as —B(OR)$_2$ or —SnR$_3$) in the presence of a suitable catalyst/ligand combination, optionally in the presence of a suitable base and in a suitable solvent. Suitable catalysts may include bis-triphenylphosphine-palladium(II) chloride. Suitable bases may include Cs$_2$CO$_3$. Suitable solvents may include 1,4-dioxane or DMF. Compounds of Formula S and of Formula E are commercially available or may be prepared by methods known in the literature.

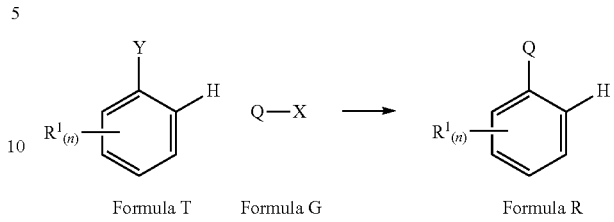

Alternatively, a compound of Formula R may be prepared from a compound of Formula T (where Y represents a suitable coupling partner functional group such as —B(OR)$_2$ or —SnR$_3$) and a compound of Formula G (where Q is a C-linked heterocycle and where X represents a suitable halogen such as F, Cl, Br or I or a suitable pseudohalogen such as OTf) in the presence of a suitable catalyst/ligand combination, optionally in the presence of a suitable base and in a suitable solvent. Suitable catalysts may include tetrakis(triphenylphosphine) palladium. Suitable bases may include K$_2$CO$_3$. Suitable solvents may include DCM/H$_2$O. Compounds of Formula T and of Formula G are commercially available or may be prepared by methods known in the literature.

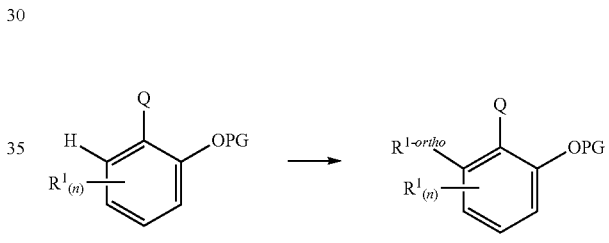

In an alternative approach, a compound of Formula Cii (a compound of Formula C where R$^{1\text{-}ortho}$=halogen and Q is a suitable ortho-directing heterocycle such as Q9, Q11, Q12, Q34 or Q35) may be prepared from a compound of Formula Ciii (a compound of Formula C where R$^{1\text{-}ortho}$=H) via reaction with a suitable halogenation reagent, in the presence of a suitable catalyst and optionally in a suitable solvent. Suitable halogenation reagents may include N-iodosuccinimide, N-bromosuccinimide, N-chlorosuccinimide or N-Fluorobenzenesulfonimide. Suitable catalysts may include Pd(OAc)$_2$. Suitable solvents may include acetic acid.

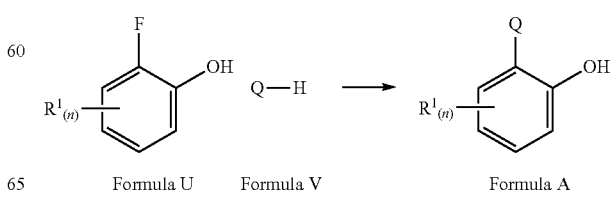

In yet another alternative approach, a compound of Formula A (where Q is an N-linked heterocycle and $R^1$ is an electron withdrawing group such as halogen, CN or $NO_2$) may be prepared from a compound of Formula U via an $S_NAr$ reaction with a compound of Formula V in the presence of a suitable base and in a suitable solvent. Suitable bases may include $K_2CO_3$. Suitable solvents may include N,N-dimethylacetamide. Compounds of Formula U and of Formula V are commercially available or may be prepared by methods known in the literature.

The following non-limiting examples provide specific synthesis methods for representative compounds of the present invention, as referred to in Table 1 below.

EXAMPLE 1: SYNTHESIS OF 5-[2-[(5-CHLORO-3-FLUORO-2-PYRIDYL)OXY]-6-FLUORO-PHENYL]-3-(DIFLUOROMETHYL)ISOXAZOLE (A1)

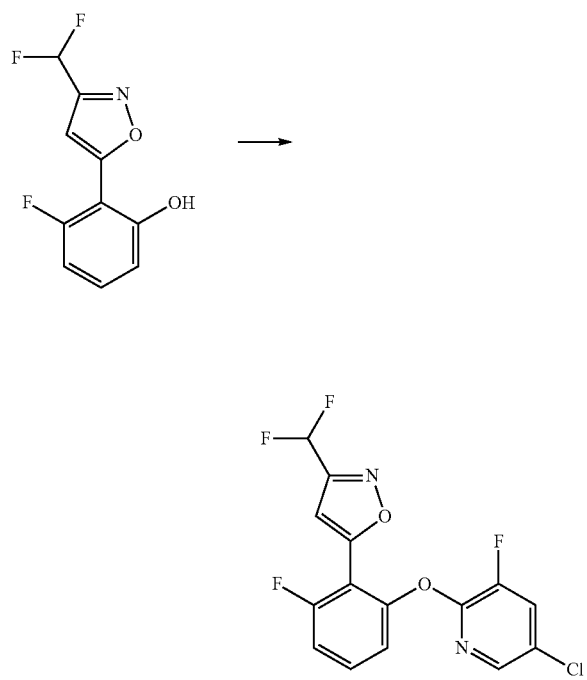 [SMILES: Oc1cccc(F)c1-c1cc(C(F)F)no1 ; Fc1cc(Cl)cnc1Oc1cccc(F)c1-c1cc(C(F)F)no1]

To a stirred solution of 2-[3-(difluoromethyl)isoxazol-5-yl]-3-fluoro-phenol (0.06 g, 0.26 mmol) in N-dimethylformamide (1.8 mL) was added $K_2CO_3$ (0.18 g, 1.3 mmol) followed by 5-chloro-2,3-difluoro-pyridine (0.049 g, 0.33 mmol). The reaction was stirred overnight at RT and then heated to 80° C. for 4 hours. The reaction mixture was cooled to RT, diluted with DCM and acidified with 2M HCl, the phases were separated then the aqueous was re-extracted with DCM and the combined organics evaporated to dryness under reduced pressure. The crude residue was purified by flash chromatography on silica gel using a gradient of 0-10% ethyl acetate in isohexane as eluent to give the desired product as a white solid (0.066 g, 70%).

$^1$H NMR (400 MHz, $CDCl_3$) δ 7.83 (d, 1H), 7.57 (d, 2H), 7.24-7.08 (m, 2H), 6.94-6.61 (m, 2H)

EXAMPLE 2: SYNTHESIS OF 3-(DIFLUOROMETHYL)-5-[2-FLUORO-6-[(5-NITRO-2-PYRIDYL)OXY]PHENYL]ISOXAZOLE (A2)

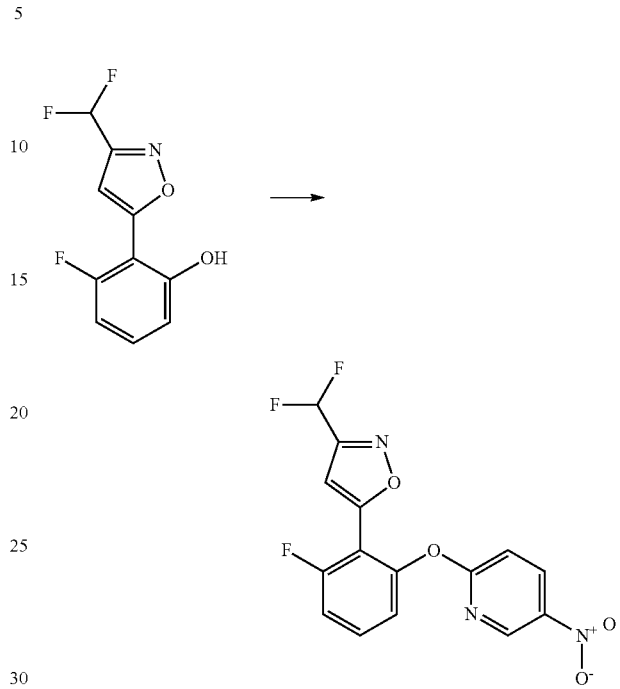

To a stirred solution of the 2-[3-(difluoromethyl)isoxazol-5-yl]-3-fluoro-phenol (0.06 g, 0.26 mmol) in N,N-dimethylformamide (1.8 mL) was added $K_2CO_3$ (0.18 g, 1.3 mmol) followed by 2-chloro-5-nitro-pyridine (0.052 g, 0.33 mmol). The reaction was stirred overnight at RT, then diluted with DCM and acidified with 2M HCl, the phases were separated then the aqueous was re-extracted with DCM and the combined organics evaporated to dryness under reduced pressure. The crude residue was purified by flash chromatography on silica gel using a gradient of 0-20% ethyl acetate in isohexane as eluent to give the desired product as a colourless oil (0.078 g, 85%).

$^1$H NMR (400 MHz, $CDCl_3$) δ 8.95 (d, 1H), 8.64-8.43 (m, 1H), 7.59 (dt, 1H), 7.32-7.10 (m, 3H), 6.97-6.53 (m, 2H)

EXAMPLE 3: SYNTHESIS OF 2-[2-[(5-CHLORO-3-FLUORO-2-PYRIDYL)OXY]-6-FLUORO-PHENYL]-5-(TRIFLUOROMETHYL)OXAZOLE (A3)

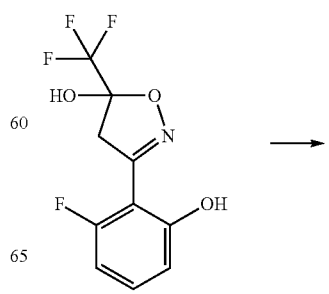

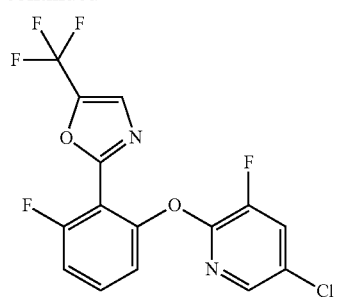

To a stirred solution of 3-(2-fluoro-6-hydroxy-phenyl)-5-(trifluoromethyl)-4H-isoxazol-5-ol (0.100 g, 0.377 mmol) in DMF (5 mL) was added $K_2CO_3$ (0.317 g, 2.26 mmol) and 5-chloro-2,3-difluoropyridine (0.141 g, 0.943 mmol). The reaction was heated at 80° C. for 4 hours and then allowed to cool to RT. The reaction mixture was diluted with EtOAc and $H_2O$, the phases were separated and the aqueous phase was extracted with further EtOAc. The combined organics were washed with $H_2O$, dried over $MgSO_4$ and evaporated to dryness under reduced pressure. The crude residue was purified by flash chromatography over silica gel using 0-10% EtOAc/isohexane as eluent to give the desired product (0.068 g, 48%) as a pale yellow solid.

$^1$H NMR (400 MHz, $CDCl_3$) δ 7.78 (d, 1H), 7.67-7.42 (m, 3H), 7.24-7.05 (m, 2H).

EXAMPLE 4: SYNTHESIS OF 5-NITRO-2-[2-[4-(TRIFLUOROMETHYL)PYRAZOL-1-YL]PHENOXY]PYRIDINE (A14)

Step 1: Synthesis of 1-(2-methoxyphenyl)-4-(trifluoromethyl)pyrazole

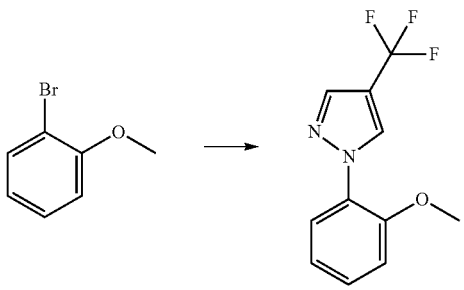

To a stirred solution of 1-bromo-2-methoxy-benzene (0.20 g, 1.07 mmol) in 1,4-dioxane (4 mL) was added 4-(trifluoromethyl)-1H-pyrazole (0.291 g, 2.14 mmol), CuI (0.204 g, 1.07 mmol), N,N'-dimethylethane-1,2-diamine (0.189 mg, 2.74 mmol) and $K_2CO_3$ (0.227 g, 1.64 mmol). The reaction was heated at reflux for 72 hours, allowed to cool to room temperature, absorbed onto silica gel and purified by flash chromatography on silica gel using a gradient of 5-50% EtOAc in isohexane as eluent to give the desired product (0.169 g, 65%) as a colourless oil.

$^1$H NMR (400 MHz, $CDCl_3$) δ 8.31 (s, 1H), 7.88 (s, 1H), 7.72 (d, 1H), 7.36 (t, 1H), 7.11-7.03 (m, 2H), 3.91 (s, 3H).

Step 2: Synthesis of 2-[4-(trifluoromethyl)pyrazol-1-yl]phenol

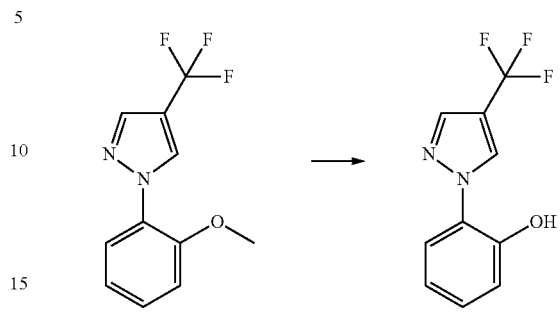

To a stirred solution of 1-(2-methoxyphenyl)-4-(trifluoromethyl)pyrazole (1.25 g, 5.16 mmol) in DCM (100 mL) at 0° C. under an atmosphere of $N_2$ was added $BBr_3$ (12.9 mL of a 1M solution in DCM, 12.9 mmol). The reaction mixture was allowed to warm to 15° C. over 2 hours, quenched with water, the pH adjusted to 7 with saturated $NaHCO_3$ solution and extracted with DCM (×3). The combined organic extracts were washed with brine, dried over $MgSO_4$, absorbed onto silica gel and purified by flash chromatography on silica gel using a gradient of 5-50% EtOAc in isohexane as eluent to give the desired product (1.06 g, 90%) as a white solid.

$^1$H NMR (400 MHz, $CDCl_3$) δ 10.50 (s, 1H), 8.28 (s, 1H), 7.94 (s, 1H), 7.39 (d, 1H), 7.26 (t, 1H), 7.12 (d, 1H), 6.96 (t, 1H).

Step 3: Synthesis of 5-nitro-2-[2-[4-(trifluoromethyl)pyrazol-1-yl]phenoxy]pyridine (A14)

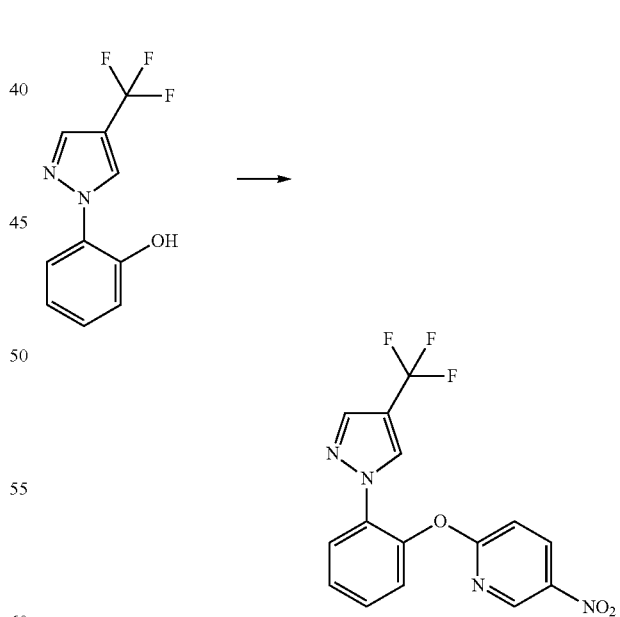

To a stirred solution of 2-[4-(trifluoromethyl)pyrazol-1-yl]phenol (0.20 g, 0.88 mmol) in DMF (5 mL) was added $K_2CO_3$ (0.242 g, 1.75 mmol) and 2-chloro-5-nitro-pyridine (0.166 mg, 1.05 mmol). The reaction was heated at 80° C. for 3 hours, allowed to cool to RT, diluted with $H_2O$ and extracted with $Et_2O$ (×3). The combined organic extracts were washed with brine, dried over MgSO$_4$ and evaporated to dryness under reduced pressure to give a brown solid. The crude product was purified by flash chromatography on silica gel using a gradient of 5-50% EtOAc in isohexane as eluent to give the desired product (0.078 g, 26%) as a pale yellow solid.

$^1$H NMR (400 MHz, CDCl$_3$) δ 8.91 (s, 1H), 8.45 (dd, 1H), 8.02 (s, 1H), 7.79-7.70 (m, 2H), 7.55-7.49 (m, 1H), 7.49-7.42 (m, 1H), 7.32 (d, 1H), 7.03 (d, 1H)

EXAMPLE 5: SYNTHESIS OF 5-CHLORO-2-[2-(4-CHLOROPYRAZOL-1-YL)PHENOXY]-3-FLUORO-PYRIDINE (A24)

Step 1: Synthesis of 5-chloro-3-fluoro-2-(2-iodophenoxy)pyridine

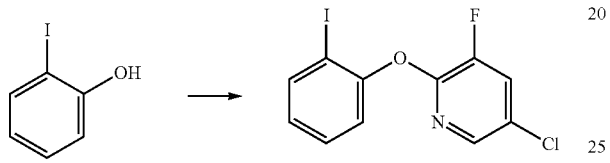

To a stirred solution of 2-iodo phenol (6.40 g, 29.1 mmol) in DMF (64 mL) was added K$_2$CO$_3$ (8.04 g, 58.2 mmol) and 5-chloro, 2,3-difluoropyridine (5.22 g, 34.9 mmol) and the reaction heated at 80° C. for 16 hours. The reaction was cooled to RT, diluted with H$_2$O (200 mL) and extracted with Et$_2$O (3×75 ml_). The combined organic extracts were washed with brine, dried over MgSO$_4$ and evaporated to dryness under reduced pressure to give a yellow oil. The crude product was purified by flash chromatography on silica gel using a gradient of 5-50% EtOAc in cyclohexane to give the desired product (10.10 g, 99%) as a colourless oil.

$^1$H NMR (400 MHz, CDCl$_3$) δ 7.91-7.82 (m, 2H), 7.53 (dd, 1H), 7.41 (t, 1H), 7.18 (d, 1H), 7.01 (t, 1H)

Step 2: Synthesis of 5-chloro-2-[2-(4-chloropyrazol-1-yl)phenoxy]-3-fluoro-pyridine (A24)

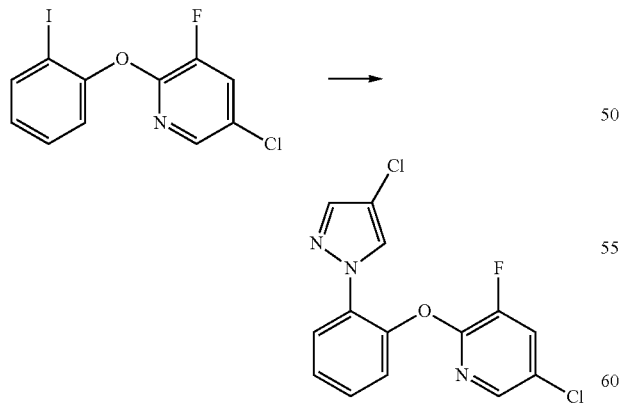

To a stirred solution of 5-chloro-3-fluoro-2-(2-iodophenoxy)pyridine (0.20 g, 0.572 mmol), in 1,4-dioxane (4 mL) was added 4-chloro-1H-pyrazole (0.117 mg, 1.14 mmol), CuI (0.109 g, 0.572 mmol), N,N'-dimethylethane-1,2-diamine (0.108 g, 1.14 mmol) and K$_2$CO$_3$ (0.168 g, 1.22 mmol) and the reaction heated at reflux for 16 hours. The reaction was allowed to cool to RT, diluted with H$_2$O (10 mL) and extracted with EtOAc (3×15 mL). The combined organic extracts were washed with brine, dried over MgSO$_4$ and evaporated to dryness under reduced pressure to give a brown oil. The crude product was purified by flash chromatography on silica gel using a gradient of 5-50% EtOAc in cyclohexane as eluent to give the desired product (27 mg, 14%) as a white solid.

$^1$H NMR (400 MHz, CDCl$_3$) δ 7.81 (s, 1H), 7.72 (d, 1H), 7.69 (dd, 1H), 7.48 (s, 1H), 7.42 (dd, 1H), 7.37-7.28 (m, 2H), 7.19 (dd, 1H).

EXAMPLE 6: SYNTHESIS OF 3-[2-[(5-CHLORO-3-FLUORO-2-PYRIDYL)OXY]-6-FLUORO-PHENYL]-5-(TRIFLUOROMETHYL) ISOXAZOLE (A25)

Step 1: Synthesis of 3-fluoro-2-[5-(trifluoromethyl)isoxazol-3-yl]phenol

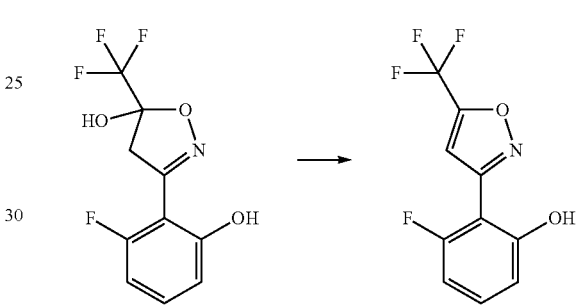

To a stirred solution of 3-(2-fluoro-6-hydroxy-phenyl)-5-(trifluoromethyl)-4H-isoxazol-5-ol (20.0 g, 75.4 mmol) in toluene (150 mL) was added p-toluene sulphonic acid monohydrate (1.59 g, 9.05 mmol). The reaction was heated at reflux for 2 h with azeotropic removal of water then cooled to RT and evaporated to dryness under reduced pressure. The residue was dissolved in CH$_2$Cl$_2$ (500 ml) and added gradually to a stirred solution of saturated aq. NaHCO$_3$ (200 ml). The organic phase was separated and washed with H$_2$O then brine and evaporated to dryness under reduced pressure to leave the desired product (17.41 g, 93%) as an off white solid which was used without further purification.

$^1$H NMR (400 MHz, CDCl$_3$) δ 9.54 (s, 1H), 7.35 (m, 2H), 6.94 (d, 1H), 6.76 (t, 1H).

Step 2: Synthesis of 3-[2-[(5-chloro-3-fluoro-2-pyridyl)oxy]-6-fluoro-phenyl]-5-(trifluoromethyl) isoxazole (A25)

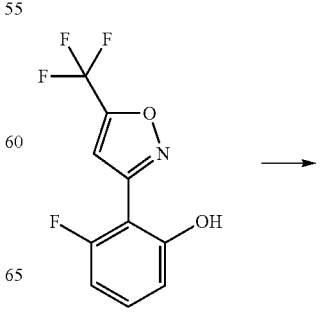

-continued

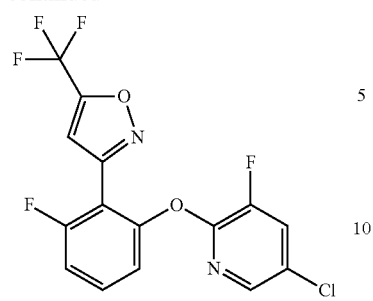

To a solution of 3-fluoro-2-[5-(trifluoromethyl)isoxazol-3-yl]phenol (1.00 g, 4.05 mmol) in N,N-dimethylformamide (15 mL) was added 5-chloro-2,3-difluoro-pyridine (3.03 g, 20.2 mmol) and potassium carbonate (0.85 g, 6.07 mmol). The reaction was heated at 80° C. for 3.5 hours, allowed to cool to RT and then quenched by addition of $H_2O$. The reaction was then extracted with EtOAc (×3) and the combined organic extracts washed with $H_2O$ and brine before being dried over $MgSO_4$, and evaporated to dryness under reduced pressure to leave a yellow oil. The crude product was purified by flash chromatography on silica gel using a gradient of 100% cyclohexane to 10% EtOAc/cyclohexane as eluent to give the desired product (30 mg, 2%) as a pale yellow gum.

$^1$H NMR (400 MHz, $CDCl_3$) δ 7.81 (s, 1H), 7.54 (m, 2H), 7.15 (t, 1H), 7.10 (d, 1H), 6.99 (s, 1H)

EXAMPLE 7: SYNTHESIS OF 5-CHLORO-3-FLUORO-2-(2-IMIDAZOL-1-YLPHENOXY) PYRIDINE (A28)

Step 1: Synthesis of 1-(2-methoxyphenyl)imidazole

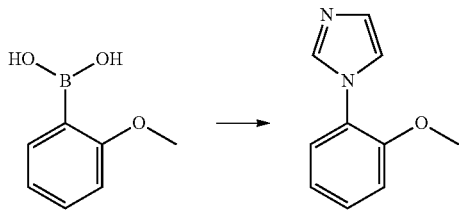

A mixture of imidazole (0.806 g, 0.012 mol), (2-methoxyphenyl)boronic acid (1.50 g, 0.0099 mol) and Cu(I)Cl (0.100 g, 0.001 mol) in MeOH (50 mL) was heated at reflux overnight. The reaction mixture was allowed to cool to RT and evaporated to dryness under reduced pressure. The crude product was purified by flash chromatography on silica gel using a gradient of 0-5% MeOH/DCM as eluent to give the desired product (133 mg, 7%) as a brown oil.

$^1$H NMR (400 MHz, $CDCl_3$) δ 7.79 (s, 1H), 7.34 (t, 1H), 7.28 (d, 1H), 7.20 (s, 1H), 7.16 (s, 1H), 7.09-7.00 (m, 2H), 3.84 (s, 3H)

Step 2: Synthesis of 2-imidazol-1-ylphenol

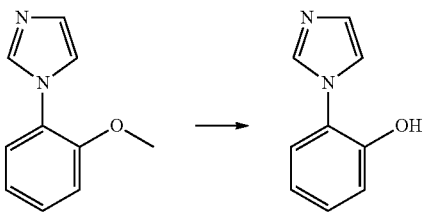

To a solution of 1-(2-methoxyphenyl)imidazole (55 mg, 0.89 mmol) in dichloromethane (18 mL) at 0° C., under nitrogen, was added dropwise boron tribromide (1M solution in DCM) (2.22 mL, 2.22 mmol) maintaining temperature at <5° C. Once addition was complete, the reaction mixture was allowed to stir at this temperature for 1 hour and then allowed to warm to RT and stirred at RT for 72 hours. The reaction mixture was quenched with water and adjusted to pH 7 with saturated aqueous sodium bicarbonate solution then washed with DCM (×3). An off-white solid precipitated out of the aqueous layer. The solid was filtered off, washed with a little water and dried in a vacuum oven at 40° C. for 3 hours to give the desired product (133 mg, 93%) as a beige solid.

$^1$H NMR (400 MHz, $CD_3OD$) δ=7.92 (s, 1H), 7.38 (s, 1H), 7.30 (d, 1H), 7.22 (t, 1H), 7.09 (s, 1H), 7.01 (d, 1H), 6.93 (t, 1H)

Step 3: Synthesis of 5-chloro-3-fluoro-2-(2-imidazol-1-ylphenoxy)pyridine (A28)

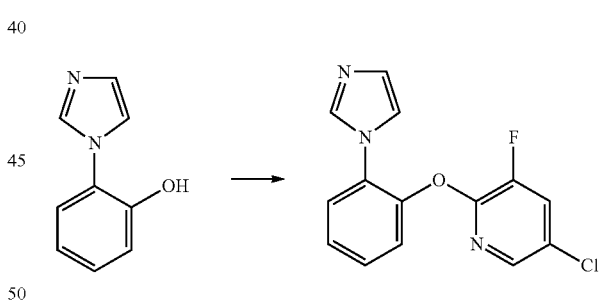

A mixture of 5-chloro-2,3-difluoro-pyridine (0.149 g, 0.10 mmol), 2-imidazol-1-ylphenol (0.133 g, 0.83 mmol) and $K_2CO_3$ (0.230 g, 1.66 mmol) in DMF (5 mL) was heated at 90° C. overnight. The reaction mixture was allowed to cool to RT, diluted with water and extracted with EtOAc (×3). The combined organic extracts were washed with brine, dried over $MgSO_4$ and evaporated to dryness under reduced pressure. The crude product was purified by flash chromatography on silica gel using a gradient of 0-5% MeOH in DCM as eluent to give the desired product (0.226 g, 94%) as a yellow oil.

$^1$H NMR (400 MHz, $CDCl_3$) δ 7.71 (s, 1H), 7.68 (s, 1H), 7.51-7.34 (m, 4H), 7.31 (d, 1H), 7.14 (s, 1H), 7.03 (s, 1H)

EXAMPLE 8: SYNTHESIS OF 3-[(5-CHLORO-3-FLUORO-2-PYRIDYL)OXY]-2-[4-(TRIFLUOROMETHYL)PYRAZOL-1-YL]BENZONITRILE (A33)

Step 1: Synthesis of 3-hydroxy-2-[4-(trifluoromethyl)pyrazol-1-yl]benzonitrile

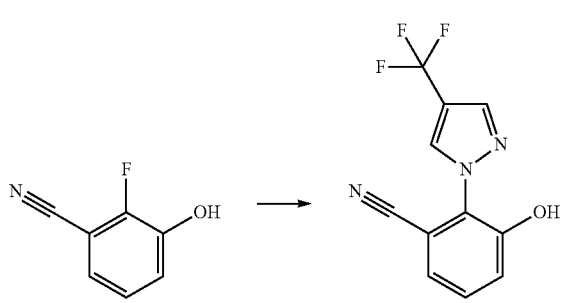 [SMILES: N#Cc1cccc(O)c1F ; N#Cc1cccc(O)c1-n1cc(C(F)(F)F)cn1]

To a solution of 2-fluoro-3-hydroxy-benzonitrile (1.0 g, 7.3 mmol) and 4-(trifluoromethyl)-1H-pyrazole (1.1 g, 8.0 mmol) in N,N-dimethylacetamide (15 mL) under a nitrogen atmosphere was added powdered $K_2CO_3$ (3.1 g, 22 mmol). The resultant mixture was heated at 150° C. for 22 hours. The reaction mixture was allowed to cool to RT, diluted with water and extracted with EtOAc (×4). The combined organic extracts were washed with brine, dried over $MgSO_4$ and evaporated to dryness to give an orange liquid. The crude product was purified by flash chromatography on silica gel using a gradient of 20 to 40% EtOAc in cyclohexane as eluent to give the desired product (594 mg, 32%) as a yellow solid.

$^1$H NMR (400 MHz, CDCl$_3$) δ=8.64 (s, 1H), 8.07 (s, 1H), 7.42-7.35 (m, 3H).

Step 2: Synthesis of 3-[(5-chloro-3-fluoro-2-pyridyl)oxy]-2-[4-(trifluoromethyl)pyrazol-1-yl]benzonitrile (A33)

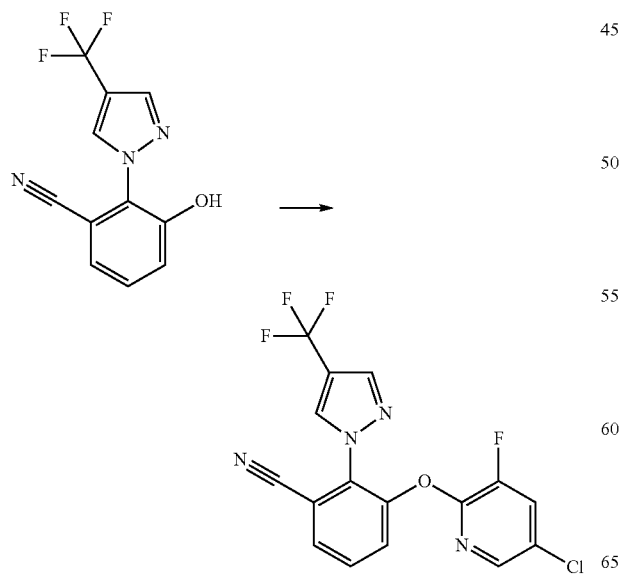

To a solution of 3-hydroxy-2-[4-(trifluoromethyl)pyrazol-1-yl]benzonitrile (0.180 g, 0.711 mmol) and 5-chloro-2,3-difluoro-pyridine (0.138 g, 0.924 mmol) in N,N-dimethylformamide (4.50 mL) was added $K_2CO_3$ (0.248 g, 1.78 mmol). The mixture was heated under microwave irradiation at 130° C. for 1 hour. The reaction mixture was poured into water and extracted with EtOAc (×3). The combined organic extracts were washed with 1M NaOH solution then brine, dried over $MgSO_4$ and evaporated to dryness under reduced pressure to give a brown liquid. The crude product was purified by flash chromatography on silica gel using a gradient of 0 to 50% EtOAc in cyclohexane as eluent to give the desired product (0.191 g, 63%) as a white solid.

$^1$H NMR (400 MHz, CDCl$_3$) δ=8.03 (s, 1H), 7.87 (s, 1H), 7.78 (d, 1H), 7.75 (dd, 1H), 7.64 (d, 1H), 7.63 (s, 1H), 7.48 (dd, 1H)

EXAMPLE 9: SYNTHESIS OF 5-CHLORO-3-FLUORO-2-[3-METHOXY-2-[4-(TRIFLUOROMETHYL)PYRAZOL-1-YL]PHENOXY]PYRIDINE (A36)

Step 1: Synthesis of 1-(2-methoxyphenyl)-4-(trifluoromethyl)pyrazole

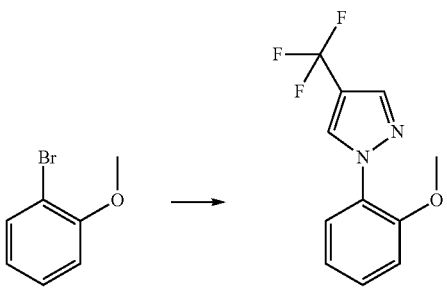

A solution of 4-(trifluoromethyl)-1H-pyrazole (291 mg, 2.14 mmol), 1-bromo-2-methoxy-benzene (200 mg, 1.07 mmol), Cu(I)I (204 mg, 1.07 mmol), N,N'-dimethylethane-1,2-diamine (188 mg, 2.14 mmol) and $K_2CO_3$ (227 mg, 2.25 mmol) in 1,4-dioxane (20 mL) was heated at reflux for 18 hours. The reaction was allowed to cool to RT and evaporated to dryness under reduced pressure. The crude product was purified by flash chromatography on silica gel using a gradient of 5-50% EtOAc in cyclohexane as eluent to give the desired product (169 mg, 65%) as a colourless oil.

$^1$H NMR (400 MHz, CDCl$_3$) δ=8.31 (s, 1H), 7.88 (s, 1H), 7.72 (d, 1H), 7.36 (t, 1H), 7.11-7.03 (m, 2H), 3.91 (s, 3H).

Step 2: Synthesis of [3-methoxy-2-[4-(trifluoromethyl)pyrazol-1-yl]phenyl]acetate

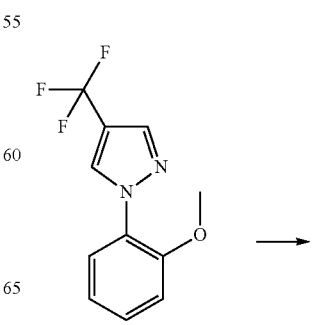

-continued

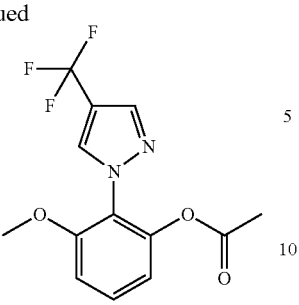

A solution of 1-(2-methoxyphenyl)-4-(trifluoromethyl)pyrazole (326 mg, 1.35 mmol), Pd(OAc)₂ (31 mg, 0.13 mmol) and (diacetoxyiodo)benzene (1.77 g, 5.38 mmol) in acetic acid (13.5 mL) was heated at 100° C. for 2 hours. The reaction was allowed to cool to RT, then evaporated to dryness under reduced pressure and azeotroped three times with toluene. The crude product was purified by flash chromatography on silica gel using a gradient of 5-100% EtOAc in cyclohexane as eluent to give the desired product (292 mg, 72%) as a yellow solid.

$^1$H NMR (400 MHz, CDCl₃) δ=7.90 (s, 1H), 7.81 (s, 1H), 7.46 (t, 1H), 6.95 (d, 1H), 6.85 (d, 1H), 3.83 (s, 3H), 2.08 (s, 3H)

Step 3: Synthesis of 3-methoxy-2-[4-(trifluoromethyl)pyrazol-1-yl]phenol

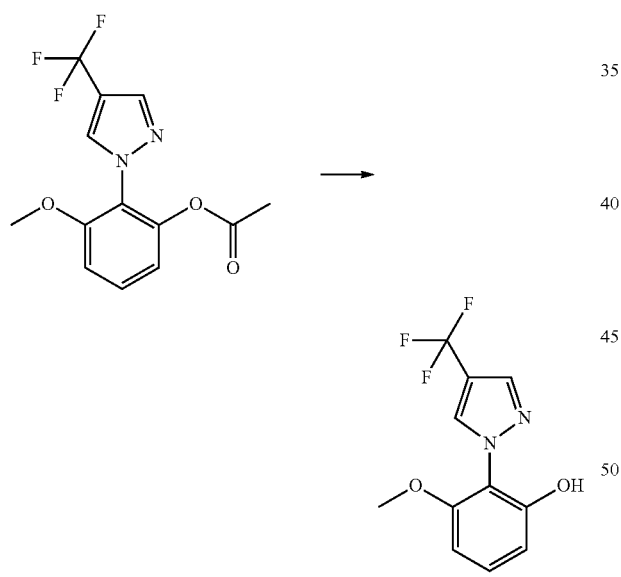

A solution of [3-methoxy-2-[4-(trifluoromethyl)pyrazol-1-yl]phenyl]acetate (295 mg, 0.95 mmol) and NaOH (133 mg, 3.32 mmol) in MeOH (5.7 mL) and H₂O (0.57 mL) was stirred at RT overnight. The reaction was diluted with water, made acidic with 2M HCl and extracted with DCM (×3). The combined organic extracts were washed with brine, dried over MgSO₄ and evaporated to dryness under reduced pressure to give the desired product (245 mg, quant) which was used without further purification.

$^1$H NMR (400 MHz, CDCl₃) δ=10.1 (br, 1H), 8.52 (s, 1H), 7.91 (s, 1H), 7.17 (t, 1H), 6.74 (d, 1H), 6.59 (d, 1H), 3.91 (s, 3H)

Step 4: Synthesis of 5-chloro-3-fluoro-2-[3-methoxy-2-[4-(trifluoromethyl)pyrazol-1-yl]phenoxy]pyridine (A36)

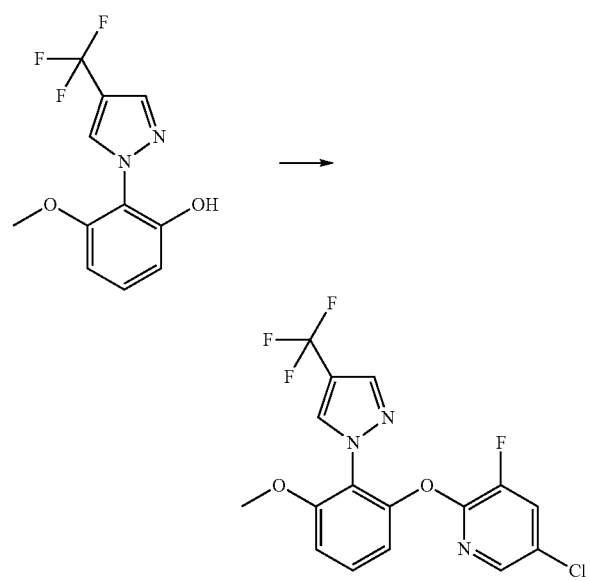

A solution of 3-methoxy-2-[4-(trifluoromethyl)pyrazol-1-yl]phenol (150 mg, 0.58 mmol), 5-chloro-2,3-difluoro-pyridine (104 mg, 0.70 mmol) and K₂CO₃ (161 mg, 1.16 mmol) in DMF (2 mL) was heated at 80° C. for 18 hours. The reaction was allowed to cool to RT, diluted with water and extracted with EtOAc (×3). The combined organic extracts were washed with brine, dried over MgSO₄ and evaporated to dryness under reduced pressure. The crude product was purified by flash chromatography on silica gel using a gradient of 5-30% EtOAc in cyclohexane as eluent to give the desired product (169 mg, 75%) as a colourless gum.

$^1$H NMR (400 MHz, CDCl₃) δ=7.78 (s, 1H), 7.72 (s, 2H), 7.47 (t, 1H), 7.39 (dd, 1H), 7.00-6.91 (m, 2H), 3.83 (s, 3H)

EXAMPLE 10: SYNTHESIS OF 5-CHLORO-3-FLUORO-2-[3-IODO-2-[4-(TRIFLUOROMETHYL)PYRAZOL-1-YL]PHENOXY]PYRIDINE (A57)

Step 1: Synthesis of 1-(2-iodo-6-methoxy-phenyl)-4-(trifluoromethyl)pyrazole

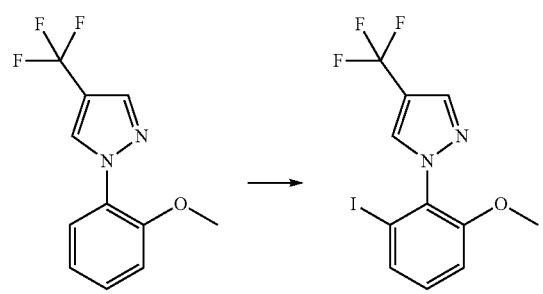 [SMILES: COc1ccccc1-n1cc(C(F)(F)F)cn1 ; COc1cccc(I)c1-n1cc(C(F)(F)F)cn1]

A solution of 1-(2-methoxyphenyl)-4-(trifluoromethyl)pyrazole (270 mg, 1.11 mmol), Pd(OAc)₂ (26 mg, 0.11 mmol) and N-iodosuccinimide (284 mg, 1.23 mmol) in acetic acid (11.5 mL) was heated at 100° C. for 2 hours. The reaction was allowed to cool to RT, then evaporated to dryness under reduced pressure and azeotroped three times with toluene. The crude product was purified by flash chromatography on silica gel using a gradient of 5-30% EtOAc in cyclohexane as eluent to give the desired product (397 mg, 97%) as a pale yellow gum.

$^1$H NMR (400 MHz, CDCl$_3$) δ=7.95 (s, 1H), 7.75 (s, 1H), 7.52 (d, 1H), 7.16 (t, 1H), 7.00 (d, 1H), 3.77 (s, 3H)

Step 2: Synthesis of 3-iodo-2-[4-(trifluoromethyl) pyrazol-1-yl]phenol

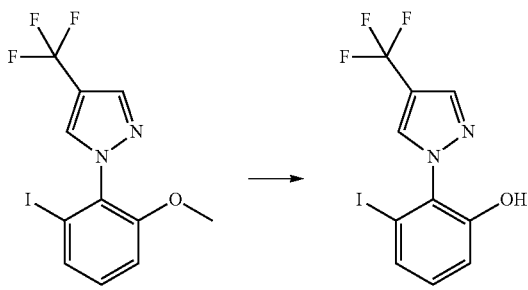 [SMILES: COc1cccc(I)c1-n1cc(C(F)(F)F)cn1 ; Oc1cccc(I)c1-n1cc(C(F)(F)F)cn1]

To a solution of 1-(2-iodo-6-methoxy-phenyl)-4-(trifluoromethyl)pyrazole (234 mg, 0.64 mmol) in dichloromethane (12.5 mL) under an atmosphere of nitrogen was added BBr$_3$ (1M solution in DCM) (1.59 mL, 1.59 mmol) dropwise. The reaction mixture was stirred at RT for 2.5 hours, then quenched with water. The reaction was basified with saturated aqueous sodium bicarbonate solution and extracted with DCM (×3). The combined organic extracts were washed with brine, dried over MgSO$_4$ and evaporated to dryness under reduced pressure to give the desired product (228 mg, quant) as a beige solid which was used without further purification.

$^1$H NMR (400 MHz, CDCl$_3$) δ=8.20 (s, 1H), 8.02 (s, 1H), 7.51 (d, 1H), 7.11-7.01 (m, 2H)

Step 3: Synthesis of 5-chloro-3-fluoro-2-[3-iodo-2-[4-(trifluoromethyl)pyrazol-1-yl]phenoxy]pyridine (A57)

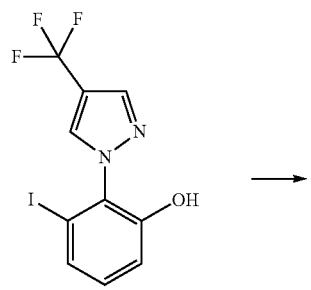

-continued

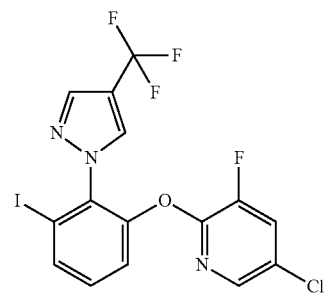

A solution of 3-iodo-2-[4-(trifluoromethyl)pyrazol-1-yl] phenol (228 mg, 0.64 mmol), 5-chloro-2,3-difluoro-pyridine (116 mg, 0.77 mmol) and K$_2$CO$_3$ (178 mg, 1.29 mmol) in DMF (2 mL) was heated at 80° C. for 18 hours. The reaction was allowed to cool to RT, diluted with water and extracted with EtOAc (×3). The combined organic extracts were washed with brine, dried over MgSO$_4$ and evaporated to dryness under reduced pressure. The crude product was purified by flash chromatography on silica gel using a gradient of 5-30% EtOAc in cyclohexane as eluent to give the desired product (210 mg, 67%) as a white solid.

$^1$H NMR (400 MHz, CDCl$_3$ δ=7.88 (dd, 1H), 7.80 (dd, 2H), 7.72 (s, 1H), 7.40 (dd, 1H), 7.36-7.22 (m, 2H)

EXAMPLE 11: SYNTHESIS OF 5-CHLORO-2-[2-(5-CHLORO-2-THIENYL)PHENOXY]-3-FLUORO-PYRIDINE (A66)

Step 1: Synthesis of 2-chloro-5-(2-methoxyphenyl)thiophene

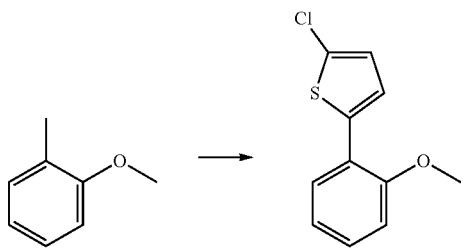

A degassed solution of 1-iodo-2-methoxy-benzene (500 mg, 2.14 mmol), (5-chloro-2-thienyl)boronic acid (416 mg, 2.56 mmol), Pd(OAc)$_2$ (25 mg, 0.11 mmol), 2-Dicyclohexylphosphino-2'-methylbiphenyl (MePhos) (159 mg, 0.43 mmol) and KF (372 mg, 6.41 mmol) in 1,4-dioxane (7.5 mL) under an N$_2$ atmosphere was heated at reflux for 18 hours. The reaction was allowed to cool to RT, diluted with water and extracted with EtOAc (×3). The combined organic extracts were washed with brine, dried over MgSO$_4$ and evaporated to dryness under reduced pressure. The crude product was purified by flash chromatography on silica gel using a gradient of 5-15% EtOAc in cyclohexane as eluent to give the desired product (438 mg, 91%) as an orange oil.

$^1$H NMR (400 MHz, CDCl$_3$ δ=7.58 (d, 1H), 7.28-7.20 (m, 2H), 7.02-6.92 (m, 2H), 6.88 (d, 1H), 3.92 (s, 3H)

Step 2: Synthesis of 2-(5-chloro-2-thienyl)phenol

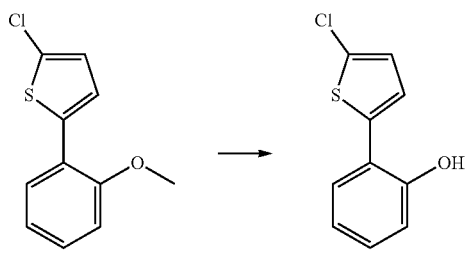

To a solution of 2-chloro-5-(2-methoxyphenyl)thiophene (438 mg, 1.95 mmol) in DCM (39 mL) at room temperature and under an N₂ atmosphere was added dropwise BBr₃ (1M solution in DCM) (4.87 mL, 4.87 mmol). The reaction mixture was stirred for 3 hours and then was quenched with water, made basic with saturated aqueous sodium bicarbonate and extracted with EtOAc (×3). The combined organic extracts were washed with brine, dried over MgSO₄ and evaporated to dryness under reduced pressure to give an orange solid (559 mg) which was used without further purification.

Step 3: Synthesis of 5-chloro-2-[2-(5-chloro-2-thienyl)phenoxy]-3-fluoro-pyridine (A66)

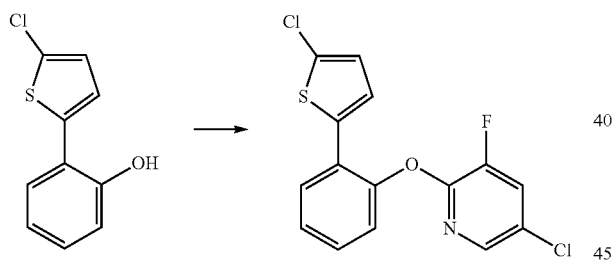

A stirred solution of the crude 2-(5-chloro-2-thienyl)phenol from step 2 above (559 mg), 5-chloro-2,3-difluoropyridine (476 mg, 3.18 mmol) and K₂CO₃ (733 mg, 5.31 mmol) in DMF (5 mL) was heated at 80° C. for 18 hours. The reaction was allowed to cool to RT, diluted with water and extracted with EtOAc (×3). The combined organic extracts were washed with brine, dried over MgSO₄ and evaporated to dryness under reduced pressure. The crude product was purified by flash chromatography on silica gel first using a gradient of 5-25% EtOAc in cyclohexane as eluent and secondly using a gradient of 0-10% EtOAc in cyclohexane to give the desired product (51 mg) as an orange gum.

¹H NMR (400 MHz, CDCl₃) δ=7.81 (s, 1H), 7.62 (d, 1H), 7.51 (d, 1H), 7.40-7.22 (m, 2H), 7.19-7.11 (m, 2H), 6.82 (s, 1H)

EXAMPLE 12: SYNTHESIS OF 5-CHLORO-3-FLUORO-2-[2-[4-(TRIFLUOROMETHYL)-2-THIENYL]PHENOXY]PYRIDINE (A97)

Step 1: Synthesis of 2-(2-methoxyphenyl)-4-(trifluoromethyl)thiophene

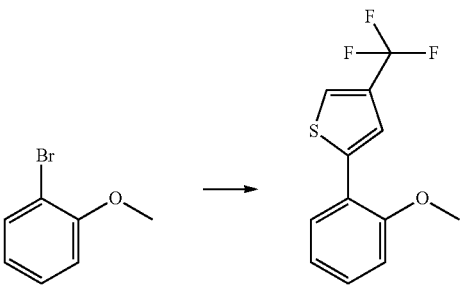

A degassed solution of 3-(trifluoromethyl)thiophene (0.56 g, 3.68 mmol), 1-bromo-2-methoxybenzene (0.688 g, 3.68 mmol), K₂CO₃ (0.771 g, 5.52 mmol), Pd(OAc)₂ (17 mg, 0.076 mmol), pivalic acid (0.128 mL, 1.10 mmol) and tricyclohexylphosphine tetrafluoroborate (54 mg, 0.147 mmol) in N,N-dimethylacetamide (12 mL) was heated at 100° C. under an atmosphere of N₂ for 18 hours. The reaction was allowed to cool to RT, diluted with water and extracted with EtOAc (×3). The combined organic extracts were washed with brine, dried over MgSO₄ and evaporated to dryness under reduced pressure. The crude product was purified twice by flash chromatography on silica gel both times using a gradient of 0-5% EtOAc in cyclohexane to give the desired product (210 mg, 22%) as a pale yellow oil.

¹H NMR (400 MHz, CDCl₃) δ 7.69-7.61 (m, 2H), 7.58 (s, 1H), 7.30 (t, 1H), 7.04-6.97 (m, 2H), 3.94 (s, 3H)

Step 2: Synthesis of 2-[4-(trifluoromethyl)-2-thienyl]phenol

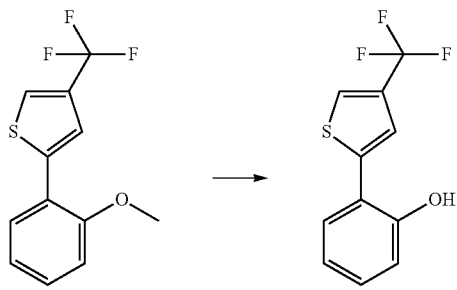 [SMILES: COc1ccccc1-c1cc(C(F)(F)F)cs1 ; Oc1ccccc1-c1cc(C(F)(F)F)cs1]

To a solution of 2-(2-methoxyphenyl)-4-(trifluoromethyl)thiophene (210 mg, 0.81 mmol) in DMF (2.5 mL) under an atmosphere of N₂ were added 1-dodecanethiol (0.397 mL, 1.626 mmol) and lithium t-butoxide (1M in THF) (1.6 mL, 1.6 mmol). The reaction mixture was heated at 100° C. for 18 hours. The reaction mixture was allowed to cool to room temperature, diluted with water and extracted with EtOAc (×3). The combined organic extracts were washed with brine, dried over MgSO₄ and evaporated to dryness under reduced pressure. The crude product was purified by flash chromatography on silica gel using a gradient of 0-20%

EtOAc in cyclohexane as eluent to give the desired product (189 mg, 95%) as a yellow oil.

¹H NMR (400 MHz, CDCl₃) δ=7.71 (s, 1H), 7.52 (s, 1H), 7.48 (d, 1H), 7.29-7.20 (m, 1H), 6.97 (t, 1H), 6.91 (d, 1H), 5.34 (s, 1H)

Step 3: Synthesis of 5-chloro-3-fluoro-2-[2-[4-(trifluoromethyl)-2-thienyl]phenoxy]pyridine (A97)

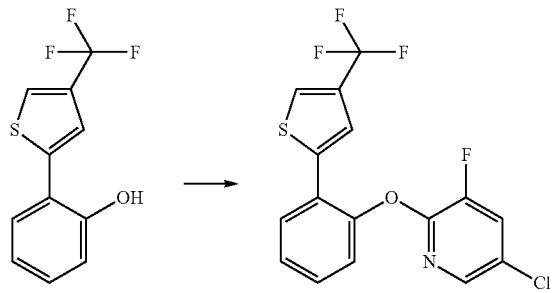 [SMILES: Oc1ccccc1-c1cc(C(F)(F)F)cs1 ; Fc1cc(Cl)cnc1Oc1ccccc1-c1cc(C(F)(F)F)cs1]

A solution of 2-[4-(trifluoromethyl)-2-thienyl]phenol (174 mg, 0.71 mmol), 5-chloro-2,3-difluoro-pyridine (128 mg, 0.86 mmol) and K₂CO₃ (197 mg, 1.43 mmol) in DMF (5 mL) was heated at 140° C. for 30 minutes under microwave irradiation. The reaction was allowed to cool to RT, diluted with water and extracted with EtOAc (×3). The combined organic extracts were washed with brine, dried over MgSO₄ and evaporated to dryness under reduced pressure. The crude product was purified by flash chromatography twice on silica gel first using a gradient of 0-5% EtOAc in cyclohexane as eluent followed by a gradient of 0-30% DCM in cyclohexane as eluent to give the desired product (136 mg, 51%) as a colourless gum.

¹H NMR (400 MHz, CDCl₃) δ=7.80 (s, 1H), 7.69 (d, 1H), 7.61 (s, 1H), 7.52-7.48 (m, 2H), 7.40 (t, 1H), 7.31 (t, 1H), 7.20 (d, 1H)

EXAMPLE 13: SYNTHESIS OF 2-[2-[3,5-BIS(TRIFLUOROMETHYL)PYRAZOL-1-YL]PHENOXY]-5-CHLORO-3-FLUORO-PYRIDINE (A123)

Step 1: Synthesis of 1-(2-methoxyphenyl)-3,5-bis(trifluoromethyl)pyrazole

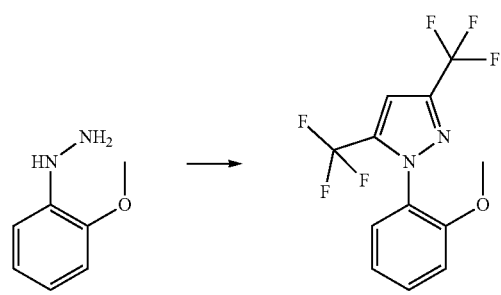

A solution of (2-methoxyphenyl)hydrazine hydrochloride (500 mg, 2.86 mmol) and 1,1,1,5,5,5-hexafluoropentane-2,4-dione (596 mg, 2.86 mmol) in EtOH (3.6 mL) and conc. H₂SO₄ (0.1 mL) was heated at reflux for 18 hours. The reaction was allowed to cool to RT, diluted with water and extracted with EtOAc (×3). The combined organic extracts were washed with brine, dried over MgSO₄ and evaporated to dryness under reduced pressure. The crude product was purified by flash chromatography on silica gel using a gradient of 0-50% EtOAc in cyclohexane as gradient to give the desired product (101 mg, 11%) as a yellow oil.

¹H NMR (400 MHz, CDCl₃ δ=7.52 (t, 1H), 7.34 (d, 1H), 7.09-7.00 (m, 3H), 3.79 (s, 3H)

Step 2: Synthesis of 2-[3,5-bis(trifluoromethyl)pyrazol-1-yl]phenol

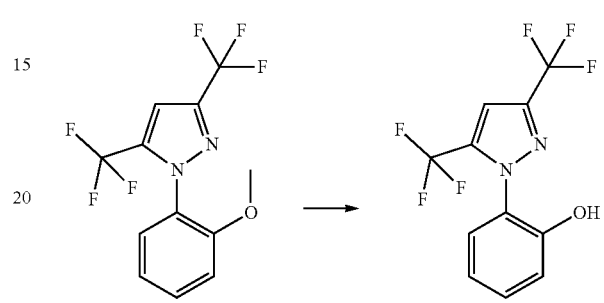

To a stirred solution of 1-(2-methoxyphenyl)-3,5-bis(trifluoromethyl)pyrazole (101 mg, 0.33 mmol) in dichloromethane (6.5 mL) under an N₂ atmosphere was added boron tribromide (1M solution in DCM) (0.81 mL, 0.81 mmol) dropwise. The reaction was stirred at RT overnight. The reaction mixture was quenched with water and extracted with DCM (×3). The combined organic extracts were washed with brine, dried over MgSO₄ and evaporated to dryness under reduced pressure to give the desired product (91 mg, 94%) as a yellow gum, which was used without further purification.

¹H NMR (400 MHz, CDCl₃) δ=7.45-7.30 (m, 2H), 7.18-7.07 (m, 2H), 7.02 (t, 1H), 6.32 (s, 1H)

Step 3: Synthesis of 2-[2-[3,5-bis(trifluoromethyl)pyrazol-1-yl]phenoxy]-5-chloro-3-fluoro-pyridine (A123)

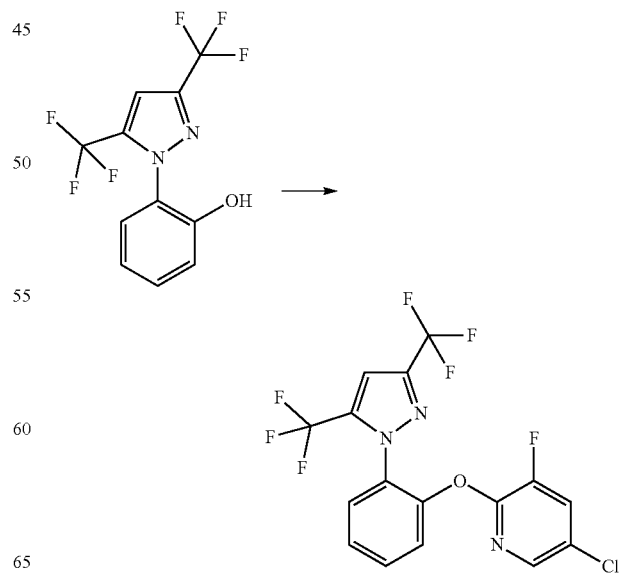

A solution of 2-[3,5-bis(trifluoromethyl)pyrazol-1-yl]phenol (97 mg, 0.23 mmol), 5-chloro-2,3-difluoro-pyridine (55 mg, 0.35 mmol) and K$_2$CO$_3$ (85 mg, 0.61 mmol) in DMF (5 mL) was heated at 140° C. under microwave irradiation for 30 minutes. The reaction was allowed to cool to RT, diluted with water and extracted with EtOAc (×3). The combined organic extracts were washed with brine, dried over MgSO$_4$ and evaporated to dryness under reduced pressure. The crude product was purified by flash chromatography on silica gel using a gradient of 0-10% EtOAc in cyclohexane as eluent to give the desired product (97 mg, 75%) as a brown gum.

$^1$H NMR (400 MHz, CDCl$_3$ δ=7.84 (s, 1H), 7.61 (t, 1H), 7.52 (d, 1H), 7.45 (d, 1H), 7.43-7.35 (m, 2H), 6.96 (s, 1H)

EXAMPLE 14: SYNTHESIS OF 2-[2-[(5-CHLORO-3-FLUORO-2-PYRIDYL)OXY]PHENYL]THIAZOLE (A147)

Step 1: Synthesis of 2-thiazol-2-ylphenol

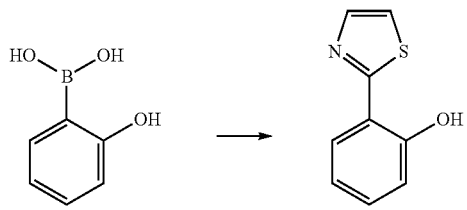 [SMILES: OB(O)c1ccccc1O ; Oc1ccccc1-c1nccs1]

A degassed solution of 2-chlorothiazole (260 mg, 2.18 mmol), (2-hydroxyphenyl)boronic acid (250 mg, 1.81 mmol), Na$_2$CO$_3$ (576 mg, 5.44 mmol), tetrakis(triphenylphosphine)palladium (21 mg, 0.018 mmol) in toluene (2.5 mL), EtOH (2.5 mL) and water (1.25 mL) was heated at 160° C. for 30 minutes under microwave irradiation. The reaction was allowed to cool to RT, diluted with water and extracted with EtOAc (×3). The combined organic extracts were washed with brine, dried over MgSO$_4$ and evaporated to dryness under reduced pressure. The crude product was purified by flash chromatography on silica gel using a gradient of 0-50% EtOAc in cyclohexane as eluent to give the desired product (127 mg, 40%) as a pale green oil.

$^1$H NMR (400 MHz, CDCl$_3$) δ=12.3 (s, 1H), 7.79 (s, 1H), 7.63 (d, 1H), 7.35-7.21 (m, 2H), 7.05 (d, 1H), 6.90 (t, 1H)

Step 2: Synthesis of 2-[2-[(5-chloro-3-fluoro-2-pyridyl)oxy]phenyl]thiazole (A147)

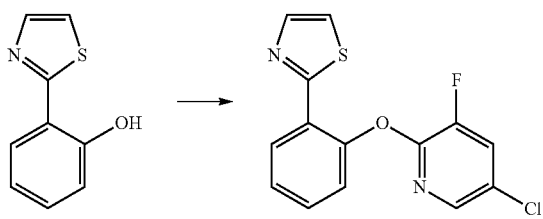 [SMILES: Oc1ccccc1-c1nccs1 ; Fc1cc(Cl)cnc1Oc1ccccc1-c1nccs1]

A solution of 2-thiazol-2-ylphenol (127 mg, 0.72 mmol), 5-chloro-2,3-difluoro-pyridine (129 mg, 0.86 mmol) and K$_2$CO$_3$ (198 mg, 1.43 mmol) in DMF (5 mL) was heated at 140° C. for 30 minutes under microwave irradiation. The reaction was allowed to cool to RT, diluted with water and extracted with EtOAc (×3). The combined organic extracts were washed with brine, dried over MgSO$_4$ and evaporated to dryness under reduced pressure. The crude product was purified by flash chromatography on silica gel using a gradient of 0-20% EtOAc in cyclohexane as eluent to give the desired product (208 mg, 95%) as a pale yellow oil.

$^1$H NMR (400 MHz, CDCl$_3$) δ=8.42 (d, 1H), 7.88 (s, 1H), 7.73 (s, 1H), 7.55 (d, 1H), 7.46 (t, 1H), 7.41-7.32 (m, 2H), 7.21 (d, 1H)

TABLE 1

Examples of herbicidal compounds of the present invention.

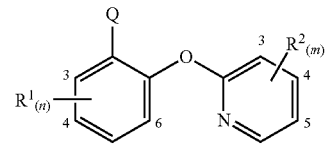

| Compound | n | R$^1$ | Q | m | R$^2$ | $^1$H NMR (400 MHz, CDCl$_3$ unless stated) |
|---|---|---|---|---|---|---|
| A1 | 1 | 3-F | 5-(3-difluoromethyl)-isoxazole | 2 | 3-F, 5-Cl | 7.83 (d, 1H), 7.57 (d, 2H), 7.24-7.08 (m, 2H), 6.94-6.61 (m, 2H) |
| A2 | 1 | 3-F | 5-(3-difluoromethyl)-isoxazole | 1 | 5-NO$_2$ | 8.95 (d, 1H), 8.64-8.43 (m, 1H), 7.59 (dt, 1H), 7.32-7.10 (m, 3H), 6.97-6.53 (m, 2H) |
| A3 | 1 | 3-F | 2-(5-trifluoromethyl)-oxazole | 2 | 3-F, 5-Cl | 7.78 (d, 1H), 7.67-7.42 (m, 3H), 7.24-7.05 (m, 2H) |
| A4 | 1 | 3-F | 5-(3-difluoromethyl)-isoxazole | 2 | 3-Cl, 5-Cl | 8.07-7.40 (m, 3H), 7.23-7.02 (m, 2H), 7.00-6.51 (m, 2H) |
| A5 | 1 | 3-F | 5-(3-difluoromethyl)-isoxazole | 1 | 6-Cl | 7.75-7.61 (m, 1H), 7.55-7.45 (m, 1H), 7.21-7.00 (m, 3H), 6.95-6.56 (m, 3H) |
| A6 | 1 | 3-F | 5-(3-difluoromethyl)-isoxazole | 1 | 5-CF$_3$ | 8.35 (s, 1H), 7.94 (d, 1H), 7.60-7.50 (m, 1H), 7.23-6.99 (m, 3H), 6.80 (s, 1H), 6.75 (t, 1H) |
| A7 | 1 | 3-F | 5-(3-difluoromethyl)-isoxazole | 1 | 6-F | 7.85-7.77 (m, 1H), 7.55-7.47 (m, 1H), 7.21-7.02 (m, 2H), 6.95-6.57 (m, 4H) |
| A8 | 1 | 3-F | 5-(3-difluoromethyl)-isoxazole | 1 | 4-CF$_3$ | 8.24 (d, 1H), 7.58-7.50 (m, 1H), 7.26-7.05 (m, 4H), 6.80 (s, 1H), 6.75 (t, 1H) |
| A9 | 1 | 3-F | 5-(3-difluoromethyl)-isoxazole | 1 | 5-Cl | 8.03 (d, 1H), 7.73-7.62 (m, 1H), 7.57-7.43 (m, 1H), 7.19-7.09 (m, 1H), 7.09-7.03 (m, 1H), 6.99 (d, 1H), 6.80 (d 1H), 6.75 (t, 1H) |
| A10 | 1 | 3-F | 5-(3-difluoromethyl)-isoxazole | 2 | 3-F, 5-F | 7.76 (d, 1H), 7.53-7.48 (m, 1H), 7.41-7.31 (m, 1H), 7.22-6.98 (m, 2H), 6.88 (d, 1H), 6.75 (t, 1H) |

TABLE 1-continued

Examples of herbicidal compounds of the present invention.

| Compound | n | R¹ | Q | m | R² | ¹H NMR (400 MHz, CDCl₃ unless stated) |
|---|---|---|---|---|---|---|
| A11 | 1 | 3-F | 5-(3-difluoromethyl)-isoxazole | 2 | 4-Cl, 6-Cl | 7.54-7.49 (m, 1H), 7.22-7.12 (m, 1H), 7.10-7.05 (m, 2H), 6.95 (s, 1H), 6.82 (d, 1H), 6.78 (t, 1H) |
| A12 | 1 | 3-F | 5-(3-difluoromethyl)-isoxazole | 1 | 5-CN | 8.36 (d, 1H), 7.97 (dd, 1H), 7.59-7.51 (m, 1H), 7.29-7.06 (m, 3H), 6.81 (d, 1H), 6.75 (t, 1H) |
| A13 | 1 | 3-F | 5-(3-difluoromethyl)-isoxazole | 2 | 3-F, 4-Cl | 7.96 (s, 1H), 7.55-7.48 (m, 1H), 7.19-7.00 (m, 3H), 6.81 (d, 1H), 6.78 (t, 1H) |
| A14 | 0 | — | 4-(trifluoromethyl)-pyrazol-1-yl | 1 | 5-NO₂ | 8.91 (s, 1H), 8.45 (dd, 1H), 8.02 (s, 1H), 7.79-7.70 (m, 2H), 7.55-7.49 (m, 1H), 7.49-7.42 (m, 1H), 7.32 (d, 1H), 7.03 (d, 1H) |
| A15 | 0 | — | 4-(trifluoromethyl)-pyrazol-1-yl | 1 | 5-CF₃ | 8.32 (s, 1H), 8.03 (s, 1H), 7.89 (dd, 1H), 7.79-7.71 (m, 2H), 7.52-7.46 (m, 1H), 7.46-7.38 (m, 1H), 7.30 (d, 1H), 7.01 (d, 1H) |
| A16 | 0 | — | 4-(trifluoromethyl)-pyrazol-1-yl | 2 | 3-F, 5-Cl | 8.18 (s, 1H), 7.81-7.73 (m, 3H), 7.51-7.43 (m, 2H), 7.40 (t, 1H), 7.32 (d, 1H) |
| A17 | 0 | — | 4-(trifluoromethyl)-pyrazol-1-yl | 1 | 5-Cl | 8.09 (s, 1H), 8.02 (d, 1H), 7.80 (s, 1H), 7.76 (dd, 1H), 7.62 (dd, 1H), 7.49-7.41 (m, 1H), 7.41-7.33 (m, 1H), 7.25 (d, 1H), 6.88 (d, 1H) |
| A18 | 0 | — | 4-(trifluoromethyl)-pyrazol-1-yl | 2 | 3-F, 5-F | 8.20 (s, 1H), 7.81-7.73 (m, 2H), 7.72 (s, 1H), 7.49-7.42 (m, 1H), 7.41-7.34 (m, 1H), 7.34-7.22 (m, 2H) |
| A19 | 0 | — | 4-(trifluoromethyl)-pyrazol-1-yl | 1 | 5-CN | 8.34 (s, 1H), 8.01 (s, 1H), 7.90 (dd, 1H), 7.79-7.70 (m, 2H), 7.55-7.48 (m, 1H), 7.48-7.41 (m, 1H), 7.31 (d, 1H), 7.01 (d, 1H) |
| A20 | 1 | 3-F | 5-(3-difluoromethyl)-isoxazole | 2 | 3-F, 5-Br | 7.90 (d, 1H), 7.66 (dd, 1H), 7.52 (dt, 1H), 7.17 (ddd, 1H), 7.10 (td, 1H), 6.95-6.57 (m, 2H) |
| A21 | 1 | 3-F | 5-(3-difluoromethyl)-isoxazole | 2 | 3-F, 5-CF₃ | 8.11 (dd, 1H), 7.73 (dd, 1H), 7.56 (dt, 1H), 7.26-7.18 (m, 1H), 7.16 (td, 1H), 6.92-6.57 (m, 2H) |
| A22 | 1 | 3-F | 5-(3-difluoromethyl)-isoxazole | 2 | 3-F, 5-NO₂ | 8.73 (d, 1H), 8.32 (dd, 1H), 7.60 (dt, 1H), 7.30-7.22 (m, 1H), 7.18 (td, 1H), 6.94-6.56 (m, 2H) |
| A23 | 1 | 3-F | 5-(3-difluoromethyl)-isoxazole | 2 | 3-F, 5-CN | 8.08 (d, 1H), 7.79 (dd, 1H), 7.57 (dt, 1H), 7.23 (ddd, 1H), 7.15 (td, 1H), 6.97-6.58 (m, 2H) |
| A24 | 0 | — | 4-(chloro)pyrazol-1-yl | 2 | 3-F, 5-Cl | 7.81 (s, 1H), 7.72 (d, 1H), 7.69 (dd, 1H), 7.48 (s, 1H), 7.42 (dd, 1H), 7.37-7.28 (m, 2H), 7.19 (dd, 1H) |
| A25 | 1 | 3-F | 3-(5-trifluoromethyl)-isoxazole | 2 | 3-F, 5-Cl | 7.81 (s, 1H), 7.54 (m, 2H), 7.15 (t, 1H), 7.10 (d, 1H), 6.99 (s, 1H) |
| A26 | 0 | — | 4-cyano-pyrazol-1-yl | 2 | 3-F, 5-Cl | 8.32 (s, 1H), 7.91 (s, 1H), 7.82 (d, 1H), 7.79 (dd, 1H), 7.53 (dd, 1H), 7.51-7.45 (m, 1H), 7.45-7.39 (m, 1H), 7.30 (dd, 1H) |
| A27 | 0 | — | 4-bromo-pyrazol-1-yl | 2 | 3-F, 5-Cl | 7.91 (s, 1H), 7.79 (d, 1H), 7.75 (dd, 1H), 7.57 (s, 1H), 7.49 (dd, 1H), 7.44-7.33 (m, 2H), 7.27 (dd, 1H) |
| A28 | 0 | — | imidazo-1-yl | 2 | 3-F, 5-Cl | 7.71 (s, 1H), 7.68 (s, 1H), 7.51-7.34 (m, 4H), 7.31 (d, 1H), 7.14 (s, 1H), 7.03 (s, 1H) |
| A29 | 0 | — | 1,2,4-triazo-1-yl | 2 | 3-F, 5-Cl | 8.58 (s, 1H), 8.01 (s, 1H), 7.82-7.78 (m, 2H), 7.52-7.38 (m, 3H), 7.32 (d, 1H) |
| A30 | 1 | 3-F | 3-(5-difluoromethyl)-isoxazole | 2 | 3-F, 5-Cl | 8.80 (s, 1H), 7.55-7.40 (m, 2H), 7.18 (t, 1H), 7.09 (d, 1H), 6.84 (s, 1H), 6.75 (t, 1H) |
| A31 | 1 | 3-F | 5-(3-trifluoromethyl)-isoxazole | 2 | 3-F, 5-Cl | ⊐ 7.82 (s, 1H), 7.57-7.51 (m, 2H), 7.18 (t, 1H), 7.11 (d, 1H), 6.88 (s, 1H) |

TABLE 1-continued

Examples of herbicidal compounds of the present invention.

| Compound | n | R¹ | Q | m | R² | ¹H NMR (400 MHz, CDCl₃ unless stated) |
|---|---|---|---|---|---|---|
| A32 | 1 | 3-CN | 4-(trifluoromethyl)pyrazol-1-yl | 1 | 5-Cl | 8.00 (d, 1H), 7.93 (s, 1H), 7.87 (s, 1H), 7.73 (d, 1H), 7.67-7.55 (m, 3H), 6.85 (d, 1H) |
| A33 | 1 | 3-CN | 4-(trifluoromethyl)pyrazol-1-yl | 2 | 3-F, 5-Cl | 8.03 (s, 1H), 7.87 (s, 1H), 7.78-7.70 (m, 2H), 7.67-7.60 (m, 2H), 7.48 (dd, 1H) |
| A34 | 1 | 3-CN | 4-(trifluoromethyl)pyrazol-1-yl | 2 | 3,5-di-F | 8.03 (s, 1H), 7.87 (s, 1H), 7.75-7.70 (m, 2H), 7.65-7.60 (m, 2H), 7.30 (ddd, 1H) |
| A35 | 1 | 3-F | 2-(5-difluoromethyl)oxazole | 2 | 3-F, 5-Cl | 7.78 (s, 1H), 7.55-7.45 (m, 2H), 7.38 (s, 1H), 7.20-7.10 (m, 2H), 6.68 (t, 1H) |
| A36 | 1 | 3-OMe | 4-(trifluoromethyl)pyrazol-1-yl | 2 | 3-F, 5-Cl | 7.78 (s, 1H), 7.72 (s, 2H), 7.47 (t, 1H), 7.39 (dd, 1H), 7.00-6.91 (m, 2H), 3.83 (s, 3H) |
| A37 | 1 | 3-F | 5-(3-difluoromethyl)-isoxazole | 2 | 3-CN, 5-Cl | 8.15 (d, 1H), 8.00 (d, 1H), 7.60-7.52 (m, 1H), 7.27-7.20 (m, 1H), 7.15 (dd, 1H), 6.90 (d, 1H), 6.76 (t, 1H) |
| A38 | 1 | 3-F | 5-(3-difluoromethyl)-isoxazole | 2 | 3-NO₂, 5-Cl | 8.41 (d, 1H), 8.20 (d, 1H), 7.60-7.54 (m, 1H), 7.24 (t, 1H), 7.12 (d, 1H), 6.94 (d, 1H), 6.74 (t, 1H) |
| A39 | 1 | 3-F | 5-(3-difluoromethyl)-isoxazole | 2 | 3-F, 5-SO₂Me | 8.36 (d, 1H), 7.99 (dd, 1H), 7.59 (td, 1H), 7.28-7.24 (m, 1H), 7.15 (d, 1H), 6.89 (s, 1H), 6.76 (t, 1H), 3.10 (s, 3H) |
| A40 | 1 | 3-F | 5-(3-difluoromethyl)-isoxazole | 1 | 5-SO₂Me | 8.61 (d, 1H), 8.22 (dd, 1H), 7.59-7.53 (m, 1H), 7.25-7.19 (m, 2H), 7.12 (d, 1H), 6.83 (d, 1H), 6.75 (t, 1H), 3.08 (s, 3H). |
| A41 | 1 | 3-F | 5-(3-difluoromethyl)-isoxazole | 1 | 5-Br | 8.13 (d, 1H), 7.82 (dd, 1H), 7.51 (dt, 1H), 7.14 (ddd, 1H), 7.06 (td, 1H), 6.95 (d, 1H), 6.78 (s, 1H), 6.75 (t, 1H) |
| A42 | 1 | 3-Cl | 5-(3-difluoromethyl)-isoxazole | 2 | 3-F, 5-Cl | 7.83 (d, 1H), 7.53-7.40 (m, 3H), 7.21 (dd, 1H), 6.78 (t, 1H), 6.69 (s, 1H) |
| A43 | 0 | — | 5-(3-difluoromethyl)-isoxazole | 2 | 3-F, 5-Cl | 8.05 (dd, 1H), 7.88 (d, 1H), 7.59 (dd, 1H), 7.56-7.50 (m, 1H), 7.39 (dt, 1H), 7.29-7.21 (m, 1H), 6.87 (s, 1H), 6.75 (t, 1H) |
| A44 | 1 | 3-Br | 5-(3-difluoromethyl)-isoxazole | 2 | 3-F, 5-Cl | 7.84 (d, 1H), 7.63 (dd, 1H), 7.50-7.40 (m, 2H), 7.23 (d, 1H), 6.80 (t, 1H), 6.64 (s, 1H) |
| A45 | 0 | — | 1,2,3-triazo-2-yl | 2 | 3-F, 5-Cl | 7.84 (dd, 1H), 7.63 (d, 1H), 7.60 (s, 2H), 7.45-7.28 (m, 4H) |
| A46 | 1 | 3-NO₂ | 4-(trifluoromethyl)pyrazol-1-yl | 2 | 3-F, 5-Cl | 7.99 (s, 1H), 7.89 (dd, 1H), 7.84-7.73 (m, 1H), 7.72-7.60 (m, 2H), 7.49 (dd, 1H) |
| A47 | 1 | 3-F | 5-(3-difluoromethyl)-isoxazole | 1 | 6-CF₃ | 7.87 (t, 1H), 7.53-7.48 (m, 1H), 7.38 (d, 1H), 7.20-7.12 (m, 3H), 6.79 (s, 1H), 6.75 (t, 1H) |
| A48 | 1 | 3-F | 5-(3-difluoromethyl)-isoxazole | 1 | 6-OCF₂H | 7.77 (t, 1H), 7.52-7.48 (m, 1H), 7.14 (t, 1H), 7.08 (d, 1H), 6.95 (t, 1H), 6.80 (d, 1H), 6.76 (d, 1H), 6.75 (t, 1H), 6.60 (d, 1H) |
| A49 | 1 | 3-F | 5-(3-difluoromethyl)-isoxazole | 1 | 3-CN | 8.23 (d, 1H), 8.03 (d, 1H), 7.60-7.52 (m, 1H), 7.25-7.10 (m, 3H), 6.87 (s, 1H), 6.65 (t, 1H) |
| A50 | 1 | 3-F | 5-(3-difluoromethyl)-isoxazole | 2 | 5,6-di-F | 7.62-7.55 (m, 1H), 7.54-7.49 (m, 1H), 7.18-7.10 (m, 2H), 6.87 (s, 1H), 6.75 (t, 1H), 6.61 (dd, 1H) |
| A51 | 1 | 3-F | 5-(3-difluoromethyl)-isoxazole | 2 | 3-Cl, 5-CF₃ | 8.20 (s, 1H), 8.01 (s, 1H), 7.58-7.53 (m, 1H), 7.21 (t, 1H), 7.14 (d, 1H), 6.90 (s, 1H), 6.78 (t, 1H) |
| A53 | 1 | 3-F | 5-(3-difluoromethyl)-isoxazole | 1 | 3-F | 7.86 (d, 1H), 7.54-7.45 (m, 2H), 7.18-7.08 (m, 2H), 7.05-7.00 (m, 1H), 6.85 (s, 1H), 6.75 (t, 1H) |
| A54 | 1 | 3-Me | 4-(trifluoromethyl)pyrazol-1-yl | 2 | 3-F, 5-Cl | 7.80 (s, 1H), 7.79-7.70 (m, 2H), 7.49-7.34 (m, 2H), 7.24 (d, 1H), 7.15 (d, 1H), 2.18 (s, 3H) |

TABLE 1-continued

Examples of herbicidal compounds of the present invention.

| Compound | n | R¹ | Q | m | R² | $^1$H NMR (400 MHz, CDCl$_3$ unless stated) |
|---|---|---|---|---|---|---|
| A55 | 1 | 3-F | 5-(3-difluoromethyl)-isoxazole | 1 | 6-CHF$_2$ | 7.85 (t, 1H), 7.52-7.45 (m, 1H), 7.36 (d, 1H), 7.17-7.05 (m, 3H), 6.80 (s, 1H), 6.73 (t, 1H), 6.32 (t, 1H) |
| A56 | 1 | 3-F | 5-(3-difluoromethyl)-isoxazole | 1 | 4-Et | 8.00 (d, 1H), 7.49-7.42 (m, 1H), 7.08 (t, 1H), 7.05 (d, 1H), 6.88-6.85 (m, 1H), 6.84 (s, 1H), 6.80 (s, 1H), 6.77 (t, 1H), 2.67 (q, 2H), 1.27 (t, 3H) |
| A57 | 1 | 3-I | 4-(trifluoromethyl)pyrazol-1-yl | 1 | 3-F, 5-Cl | 7.88 (dd, 1H), 7.80 (dd, 2H), 7.72 (s, 1H), 7.40 (dd, 1H), 7.36-7.22 (m, 2H) |
| A58 | 1 | 3-F | 4-(trifluoromethyl)pyrazol-1-yl | 1 | 3-F, 5-Cl | 7.84 (s, 1H), 7.76 (s, 2H), 7.53-7.45 (m, 1H), 7.41 (dd, 1H), 7.22-7.12 (m, 2H) |
| A59 | 1 | 3-Br | 4-(trifluoromethyl)pyrazol-1-yl | 1 | 3-F, 5-Cl | 7.81-7.70 (m, 3H), 7.65 (d, 1H), 7.48-7.35 (m, 2H), 7.30 (d, 1H) |
| A60 | 1 | 3-F | 5-(3-difluoromethyl)-isoxazole | 1 | 4-Cl | 8.30 (d, 1H), 7.60-7.52 (m, 1H), 7.23 (t, 1H), 7.02 (d, 1H), 6.85-6.50 (m, 3H), 6.77 (t, 1H) |
| A61 | 2 | 3,4-di-Br | 4-(trifluoromethyl)pyrazol-1-yl | 2 | 3-F, 5-Cl | 7.85 (d, 1H), 7.82-7.78 (m, 2H), 7.72 (s, 1H), 7.41 (dd, 1H), 7.25 (d, 1H) |
| A62 | 1 | 3-F | 5-(3-difluoromethyl)-isoxazole | 1 | 4-OCF$_3$ | 8.29 (d, 1H), 7.58-7.52 (m, 1H), 7.22 (q, 1H), 7.04 (d, 1H), 6.87-6.80 (m, 3H), 6.76 (t, 1H) |
| A63 | 1 | 3-F | 5-(3-difluoromethyl)-isoxazole | 2 | 3-NO$_2$, 4-Me | 7.98 (d, 1H), 7.53 (q, 1H), 7.18 (t, 1H), 7.14 (d, 1H), 6.96 (d, 1H), 6.88 (s, 1H), 6.76 (t, 1H), 2.43 (s, 3H) |
| A64 | 1 | 3-F | 5-(3-difluoromethyl)-isoxazole | 1 | 5-OCF$_3$ | 8.00 (d, 1H), 7.62 (dd, 1H), 7.55-7.49 (m, 1H), 7.15 (t, 1H), 7.10-7.04 (m, 2H), 6.80 (s, 1H), 6.75 (t, 1H) |
| A65 | 1 | 3-F | 5-(3-difluoromethyl)-isoxazole | 1 | 4-Me | 7.98 (d, 1H), 7.48 (q, 1H), 7.10 (t, 1H), 7.04 (d, 1H), 6.87-6.77 (m, 3H), 6.75 (t, 1H), 2.47 (s, 3H) |
| A66 | 0 | — | 5-chloro-2-thienyl | 2 | 3-F, 5-Cl | 7.81 (s, 1H), 7.62 (d, 1H), 7.51 (d, 1H), 7.40-7.22 (m, 2H), 7.19-7.11 (m, 2H), 6.82 (d, 1H) |
| A67 | 0 | — | 5-cyano-2-thienyl | 2 | 3-F, 5-Cl | 7.81 (s, 1H), 7.71 (d, 1H), 7.60-7.49 (m, 2H), 7.43 (t, 1H), 7.40-7.31 (m, 2H), 7.20 (d, 1H) |
| A69 | 0 | — | 5-chloro-3-thienyl | 2 | 3-F, 5-Cl | 7.77 (s, 1H), 7.50 (d, 1H), 7.44 (d, 1H), 7.41-7.32 (m, 1H), 7.32-7.26 (m, 1H), 7.21 (s, 1H), 7.20-7.11 (m, 2H) |
| A70 | 0 | — | 3-thienyl | 2 | 3-F, 5-Cl | 7.75 (s, 1H), 7.58 (d, 1H), 7.45 (s, 1H), 7.41 (d, 1H), 7.36-7.21 (m, 4H), 7.20 (d, 1H) |
| A71 | 0 | — | 4-methoxy-2-thienyl | 2 | 3-F, 5-Cl | 7.81 (s, 1H), 7.68 (d, 1H), 7.49 (d, 1H), 7.38-7.24 (m, 2H), 7.14 (d, 1H), 7.04 (s, 1H), 6.20 (s, 1H), 3.77 (s, 3H) |
| A72 | 0 | — | 2,5-dimethyl-pyrazol-3-yl | 2 | 3-F, 5-Cl | 7.74 (s, 1H), 7.44-7.50 (m, 1H), 7.41-7.30 (m, 3H), 7.25-7.21 (m, 1H), 5.92 (s, 1H), 3.70 (s, 3H), 2.19 (s, 3H) |
| A73 | 0 | — | 2-methyl-5-(trifluoromethyl)pyrazol-3-yl | 2 | 3-F, 5-Cl | 7.78 (s, 1H), 7.59-7.51 (m, 1H), 7.45-7.36 (m, 3H), 7.30-7.22 (m, 1H), 6.41 (s, 1H), 3.82 (s, 3H) |
| A74 | 0 | — | 5-methyl-sulfanyl-1,3,4-thiadiazol-2-yl | 2 | 3-F, 5-Cl | 8.45 (d, 1H), 7.87 (d, 1H), 7.59 (d, 1H), 7.52 (t, 1H), 7.39 (t, 1H), 7.20 (d, 1H), 2.81 (s, 3H) |
| A75 | 0 | | 5-methyl-sulfonyl-1,3,4-thiadiazol-2-yl | 0 | 3-F, 5-Cl | 8.60 (d, 1H), 7.91 (s, 1H), 7.68-7.55 (m, 2H), 7.42 (t, 1H), 7.28-7.20 (m, 1H), 3.48 (s, 3H) |
| A76 | 1 | 3-F | 5-(3-difluoromethyl)-isoxazole | 2 | 3-Me, 6-CN | 7.87 (d, 1H), 7.55-7.50 (m, 1H), 7.20 (t, 1H), 7.15 (d, 1H), 6.95 (d, 1H), 6.88 (s, 1H), 6.75 (t, 1H), 2.35 (s, 3H) |

TABLE 1-continued

Examples of herbicidal compounds of the present invention.

| Compound | n | $R^1$ | Q | m | $R^2$ | $^1$H NMR (400 MHz, CDCl$_3$ unless stated) |
|---|---|---|---|---|---|---|
| A77 | 1 | 3-F | 5-(3-difluoromethyl)-isoxazole | 1 | 5-CHF$_2$ | 8.20 (d, 1H), 7.55-7.48 (m, 1H), 7.19-7.10 (m, 3H), 7.08 (d, 1H), 6.78 (s, 1H), 6.75 (t, 1H), 6.65 (t, 1H) |
| A78 | 1 | 3-F | 5-(3-difluoromethyl)-isoxazole | 2 | 4,5-di-CF$_3$ | 8.52 (d, 1H), 7.60-7.54 (m, 1H), 7.45 (s, 1H), 7.25 (t, 1H), 7.12 (d, 1H), 6.85 (s, 1H), 6.77 (t, 1H) |
| A79 | 1 | 3-F | 5-(3-difluoromethyl)-isoxazole | 1 | 6-CN | 7.85 (t, 1H), 7.55-7.50 (m, 1H), 7.81 (d, 1H), 7.25 (d, 1H), 7.18 (t, 1H), 7.11 (d, 1H), 6.81 (s, 1H), 6.72 (t, 1H) |
| A80 | 1 | 3-F | 5-(3-difluoromethyl)-isoxazole | 2 | 3-CF$_3$, 6-Cl | 8.02 (d, 1H), 7.55-7.50 (m, 1H), 7.18 (t, 1H), 7.11 (d, 1H), 7.02 (d, 1H), 6.82 (s, 1H), 6.78 (t, 1H) |
| A81 | 0 | — | 4-(trifluoromethyl)triazol-2-yl | 2 | 3-F, 5-Cl | 7.93 (d, 1H), 7.89 (s, 1H), 7.70 (s, 1H), 7.54 (t, 1H), 7.50-7.39 (m, 3H) |
| A82 | 0 | — | 4-(trifluoromethyl)triazole-1-yl | 2 | 3-F, 5-Cl | 8.33 (s, 1H), 7.81-7.89 (m, 2H), 7.57 (t, 1H), 7.52 (d, 1H), 7.45 (t, 1H), 7.38 (d, 1H) |
| A83 | 1 | 6-Br | 5-(3-difluoromethyl)-isoxazole | 2 | 3-F, 5-Cl | 7.99 (d, 1H), 7.78 (dd, 1H), 7.76 (d, 1H), 7.59 (dd, 1H), 7.34 (t, 1H), 6.76 (s, 1H), 6.75 (t, 1H) |
| A84 | 1 | 3-Br | 5-(3-difluoromethyl)-isoxazole | 2 | 3-CN, 5-F | 8.11 (s, 1H), 7.72-7.66 (m, 2H), 7.47 (t, 1H), 7.29 (d, 1H), 6.74 (t, 1H), 6.70 (s, 1H) |
| A85 | 1 | 3-Cl | 5-(3-difluoromethyl)-isoxazole | 2 | 3-CN, 5-F | 8.11 (s, 1H), 7.72-7.68 (m, 1H), 7.57-7.48 (m, 2H), 7.28-7.22 (m, 1H), 6.74 (s, 1H), 6.74 (t, 1H) |
| A86 | 1 | 3-Br | 5-(3-difluoromethyl)-isoxazole | 1 | 4-Cl | 8.01 (d, 1H), 7.61 (d, 1H), 7.43 (t, 1H), 7.21 (d, 1H), 7.01 (d, 1H), 6.88 (s, 1H), 6.77 (t, 1H), 6.57 (s, 1H) |
| A87 | 1 | 3-Br | 5-(3-difluoromethyl)-isoxazole | 1 | 4-CN | 8.25 (d, 1H), 7.67 (d, 1H), 7.47 (t, 1H), 7.25-7.18 (m, 2H), 7.10 (s, 1H), 6.75 (t, 1H), 6.58 (s, 1H) |
| A88 | 1 | 3-Br | 5-(3-difluoromethyl)-isoxazole | 1 | 5-NO$_2$ | 8.98 (s, 1H), 8.46 (d, 1H), 7.70 (d, 1H), 7.50 (t, 1H), 7.28-7.22 (m, 1H), 6.99 (d, 1H), 6.74 (t, 1H), 6.60 (s, 1H) |
| A89 | 1 | 3-Br | 5-(3-difluoromethyl)-isoxazole | 2 | 3,5-di-Cl | 7.90 (s, 1H), 7.71 (s, 1H), 7.63 (d, 1H), 7.44 (t, 1H), 7.26 (d, 1H), 6.76 (t, 1H), 6.64 (s, 1H) |
| A90 | 1 | 3-Br | 5-(3-difluoromethyl)-isoxazole | 1 | 5-CF$_3$ | 8.36 (s, 1H), 7.88 (d, 1H), 7.63 (d, 1H), 7.43 (t, 1H), 7.24 (d, 1H), 6.95 (d, 1H), 6.72 (t, 1H), 6.58 (s, 1H) |
| A91 | 1 | 3-Cl | 5-(3-difluoromethyl)-isoxazole | 1 | 4-CN | 8.26 (d, 1H), 7.57-7.45 (m, 2H), 7.21-7.16 (m, 2H), 7.14 (s, 1H), 6.75 (t, 1H), 6.63 (s, 1H) |
| A92 | 1 | 3-Cl | 5-(3-difluoromethyl)-isoxazole | 1 | 4-Cl | 8.00 (d, 1H), 7.50 (t, 1H), 7.43 (d, 1H), 7.18 (d, 1H), 7.02 (d, 1H), 6.90 (d, 1H), 6.75 (t, 1H), 6.61 (s, 1H) |
| A93 | 1 | 6-F | 5-(3-difluoromethyl)-isoxazole | 2 | 3-F, 5-Cl | 7.85-7.79 (m, 2H), 7.60 (dd, 1H), 7.41 (dt, 1H), 7.37-7.30 (m, 1H), 6.84 (s, 1H), 6.77 (t, 1H) |
| A94 | 1 | 6-Me | 5-(3-difluoromethyl)-isoxazole | 2 | 3-F, 5-Cl | 7.85 (dd, 1H), 7.75 (d, 1H), 7.56 (dd, 1H), 7.46-7.39 (m, 1H), 7.39-7.33 (m, 1H), 6.73 (t, 1H), 6.72 (s, 1H), 2.18 (s, 3H) |
| A95 | 1 | 6-Cl | 5-(3-difluoromethyl)-isoxazole | 2 | 3-F, 5-Cl | 7.95 (dd, 1H), 7.77 (d, 1H), 7.60 (dt, 2H), 7.40 (t, 1H), 6.78 (s, 1H), 6.75 (t, 1H) |
| A96 | 0 | — | 4-methoxypyrazol-1-yl | 2 | 3-F, 5-Cl | 7.79-7.72 (m, 2H), 7.60 (s, 1H), 7.45 (dd, 1H), 7.39-7.31 (m, 3H), 7.30-7.22 3.71 (s, 3H) |
| A97 | 0 | — | 4-(trifluoromethyl)thien-2-yl | 2 | 3-F, 5-Cl | 7.80 (s, 1H), 7.69 (d, 1H), 7.61 (s, 1H), 7.52-7.48 (m, 2H), 7.40 (t, 1H), 7.31 (t, 1H), 7.20 (d, 1H) |
| A98 | 1 | 3-Br | 5-(3-difluoromethyl)-isoxazole | 1 | 6-F | 7.74 (q, 1H), 7.60 (d, 1H), 7.41 (t, 1H), 7.29-7.20 (m, 1H), 6.75 (t, 1H), 6.70 (d, 1H), 6.65-6.55 (m, 2H) |

TABLE 1-continued

Examples of herbicidal compounds of the present invention.

| Compound | n | R¹ | Q | m | R² | ¹H NMR (400 MHz, CDCl₃ unless stated) |
|---|---|---|---|---|---|---|
| A99 | 1 | 3-Br | 5-(3-difluoromethyl)-isoxazole | 1 | 4-CF₃ | 8.26 (d, 1H), 7.64 (dd, 1H), 7.45 (t, 1H), 7.29-7.18 (m, 2H), 7.08 (s, 1H), 6.73 (t, 1H), 6.56 (s, 1H) |
| A100 | 1 | 3-Br | 5-(3-difluoromethyl)-isoxazole | 1 | 5-Cl | 8.04 (s, 1H), 7.63-7.57 (m, 2H), 7.41 (t, 1H), 7.20 (d, 1H), 6.81 (d, 1H), 6.76 (t, 1H), 6.57 (s, 1H) |
| A101 | 1 | 3-Br | 5-(3-difluoromethyl)-isoxazole | 2 | 3,5-di-F | 7.85 (s, 1H), 7.58 (d, 1H), 7.38 (t, 1H), 7.21 (t, 1H), 6.93 (d, 1H), 6.84 (t, 1H), 6.75 (s, 1H) |
| A102 | 1 | 3-Br | 5-(3-difluoromethyl)-isoxazole | 1 | 5-CN | 8.39 (s, 1H), 7.90 (d, 1H), 7.67 (d, 1H), 7.46 (t, 1H), 7.25 d, 1H), 6.95 (d, 1H), 6.73 (t, 1H), 6.58 (s, 1H) |
| A103 | 1 | 3-Br | 5-(3-difluoromethyl)-isoxazole | 2 | 3-F, 5-Br | 7.93 (s, 1H), 7.67-7.55 (m, 2H), 7.45 (t, 1H), 7.27 (d, 1H), 6.77 (t, 1H), 6.66 (s, 1H) |
| A104 | 1 | 3-Br | 5-(3-difluoromethyl)-isoxazole | 2 | 3-F, 5-CF₃ | 8.14 (s, 1H), 7.71-7.62 (m, 2H), 7.48 (t, 1H), 7.29 (d, 1H), 6.75 (t, 1H), 6.66 (s, 1H) |
| A105 | 1 | 3-Br | 5-(3-difluoromethyl)-isoxazole | 2 | 3-CN, 5-Cl | 8.18 (s, 1H), 7.91 (s, 1H), 7.69 (d, 1H), 7.47 (t, 1H), 7.29 (d, 1H), 6.75 (t, 1H), 6.71 (s, 1H) |
| A106 | 1 | 3-Br | 5-(3-difluoromethyl)-isoxazole | 1 | 5-Br | 8.15 (s, 1H), 7.75 (d, 1H), 7.60 d, 1H), 7.41 (t, 1H), 7.20 (d, 1H), 6.77 (d, 1H), 6.76 (t, 1H), 6.56 (s, 1H) |
| A107 | 1 | 3-Br | 5-(3-difluoromethyl)-isoxazole | 1 | 3-CN | 8.26 (s, 1H), 7.95 (d, 1H), 7.70 (d, 1H), 7.48 (t, 1H), 7.32 (d, 1H), 7.11 (m, 1H), 6.75 (t, 1H), 6.69 (s, 1H) |
| A108 | 1 | 3-Cl | 5-(3-difluoromethyl)-isoxazole | 1 | 5-NO₂ | 8.98 (s, 1H), 8.49 (d, 1H), 7.53 (m, 2H), 7.24 (d, 1H), 7.01 (d, 1H), 6.75 (t, 1H), 6.67 (s, 1H) |
| A109 | 1 | 3-Cl | 5-(3-difluoromethyl)-isoxazole | 2 | 3,5-di-Cl | 7.90 (s, 1H), 7.73 (s, 1H), 7.51 (t, 1H), 7.45 (d, 1H), 7.20 (d, 1H), 6.75 (t, 1H), 6.68 (s, 1H) |
| A110 | 1 | 3-Cl | 5-(3-difluoromethyl)-isoxazole | 1 | 5-CF₃ | 8.35 (s, 1H), 7.89 (dd, 1H), 7.54-7.42 (m, 2H), 7.20 (d, 1H), 6.98 (d, 1H), 6.71 (t, 1H), 6.61 (s, 1H) |
| A111 | 1 | 3-Cl | 5-(3-difluoromethyl)-isoxazole | 1 | 6-F | 7.75 (q, 1H), 7.48 (t, 1H), 7.42 (d, 1H), 7.20 (d, 1H), 6.75 (t, 1H), 6.77-6.70 (m, 1H), 6.65-6.58 (m, 2H) |
| A112 | 1 | 3-Cl | 5-(3-difluoromethyl)-isoxazole | 1 | 4-CF₃ | 8.26 (d, 1H), 7.52 (t, 1H), 7.46 (dd, 1H), 7.23-7.18 (m, 2H), 7.11 (s, 1H), 6.74 (s, 1H), 6.60 (s, 1H) |
| A113 | 1 | 3-Cl | 5-(3-difluoromethyl)-isoxazole | 1 | 5-Cl | 8.05 (s, 1H), 7.66 (d, 1H), 7.49 (t, 1H), 7.44 (d, 1H), 7.19 (d, 1H) 6.86 (d, 1H), 6.75 (t, 1H), 6.51 (s, 1H) |
| A114 | 1 | 3-Cl | 5-(3-difluoromethyl)-isoxazole | 2 | 3,5-di-F | 7.86 (s, 1H), 7.47-7.40 (m, 2H), 7.21 (t, 1H), 7.90 (d, 1H), 6.83 (t, 1H), 6.77 (s, 1H) |
| A115 | 1 | 3-Cl | 5-(3-difluoromethyl)-isoxazole | 1 | 5-CN | 8.38 (s, 1H), 7.91 (d, 1H), 7.55-7.45 (m, 2H), 7.20 (d, 1H), 7.00 (d, 1H), 6.74 (t, 1H), 6.64 (s, 1H) |
| A116 | 1 | 3-Cl | 5-(3-difluoromethyl)-isoxazole | 2 | 3-F, 5-Br | 7.91 (s, 1H), 7.60 (d, 1H), 7.52-7.42 (m, 2H), 7.20 (d, 1H), 6.75 (t, 1H), 6.70 (s, 1H) |
| A117 | 1 | 3-Cl | 5-(3-difluoromethyl)-isoxazole | 2 | 3-F, 5-CF₃ | 8.12 (s, 1H), 7.67 (d, 1H), 7.58-7.45 (m, 2H), 7.28-7.22 (m, 1H), 6.74 (t, 1H), 6.70 (s, 1H) |
| A118 | 1 | 3-Cl | 5-(3-difluoromethyl)-isoxazole | 2 | 3-CN, 5-CF₃ | 8.19 (s, 1H), 7.92 (s, 1H), 7.58-7.49 (m, 2H), 7.29-7.21 (m, 1H), 6.75 (s, 1H), 6.75 (t, 1H) |
| A119 | 1 | 3-Cl | 5-(3-difluoromethyl)-isoxazole | 1 | 5-Br | 8.14 (s, 1H), 7.77 (d, 1H), 7.49 (t, 1H), 7.43 (d, 1H), 7.18 (d, 1H), 6.80 (d, 1H), 6.76 (t, 1H), 6.61 (s, 1H) |
| A120 | 1 | 3-Cl | 5-(3-difluoromethyl)-isoxazole | 1 | 3-CN | 8.25 (d, 1H), 7.97 (d, 1H), 7.58-7.45 (m, 2H), 7.30-7.23 (m, 1H), 7.12-7.08 (m, 1H), 6.74 (t, 1H), 6.73 (s, 1H) |

TABLE 1-continued

Examples of herbicidal compounds of the present invention.

| Compound | n | R¹ | Q | m | R² | ¹H NMR (400 MHz, CDCl₃ unless stated) |
|---|---|---|---|---|---|---|
| A121 | 0 | — | 3-(trifluoromethyl)pyrazole-1-yl | 2 | 3-F, 5-Cl | 7.89 (s, 1H), 7.80-7.71 (m, 2H), 7.49-7.42 (m, 2H), 7.40 (t, 1H), 7.32 (d, 1H), 6.56 (s, 1H) |
| A122 | 0 | — | 5-(trifluoromethyl)pyrazole-1-yl | 2 | 3-F, 5-Cl | 7.82 (s, 1H), 7.60-7.53 (m, 2H), 7.51 (d, 1H), 7.41-7.32 (m, 3H), 6.70 (s, 1H) |
| A123 | 0 | — | 3,5-bis(trifluoromethyl)pyrazol-1-yl | 2 | 3-F, 5-Cl | 7.84 (s, 1H), 7.61 (t, 1H), 7.52 (d, 1H), 7.45 (d, 1H), 7.43-7.35 (m, 2H), 6.96 (s, 1H) |
| A124 | 1 | 3-F | 5-(3-difluoromethyl)-isoxazole | 2 | 4-Cl, 5-CO₂Et | 8.60 (s, 1H), 7.55-7.50 (m, 1H), 7.20 (t, 1H), 7.12 (s, 1H), 7.05 (d, 1H), 6.80 (d, 1H), 6.75 (t, 1H), 4.37 (q, 2H), 1.38 (t, 3H) |
| A126 | 0 | — | 5-(3-methyl-1,2,4-oxadiazole) | 2 | 3-F, 5-Cl | 8.20 (d, 1H), 7.75 (s, 1H), 7.66 (t, 1H), 7.53 (dd, 1H), 7.44 (t, 1H), 7.30 (d, 1H), 2.38 (s, 3H) |
| A128 | 0 | — | 3-(5-methyl-1,2,4-oxadiazole) | 2 | 3-F, 5-Cl | 8.16 (d, 1H), 7.74 (s, 1H), 7.56 (t, 1H), 7.50 (d, 1H), 7.42 (t, 1H), 7.30 (d, 1H), 2.55 (s, 3H) |
| A129 | 0 | — | 2-(4-methyl-thiazole) | 2 | 3-F, 5-Cl | 8.35 (d, 1H), 7.80 (s, 1H), 7.53 (dd, 1H), 7.41 (t, 1H), 7.35 (t, 1H), 7.18 (d, 1H), 6.87 (s, 1H), 2.46 (s, 3H) |
| A130 | 0 | — | 2-(5-methyl-1,2,4-oxadiazole) | 2 | 3-F, 5-Cl | 8.12 (d, 1H), 7.75 (s, 1H), 7.60 (t, 1H), 7.55 (dd, 1H), 7.42 (t, 1H), 7.31 (d, 1H), 2.49 (s, 3H) |
| A131 | 0 | — | 4-(5-methyl-thiadiazole) | 2 | 3-F, 5-Cl | 7.76 (d, 1H), 7.62 (d, 1H), 7.55 (t, 1H), 7.41 (t, 1H), 7.37 (dd, 1H), 7.31 (d, 1H), 2.58 (s, 3H) |
| A132 | 0 | — | 2-(1,3,4-oxadiazole) | 2 | 3-F, 5-Cl | 8.40 (s, 1H), 8.17 (d, 1H), 7.75 (s, 1H), 7.62 (t, 1H), 7.55 (dd, 1H), 7.44 (t, 1H), 7.31 (d, 1H) |
| A137 | 1 | 3-F | 5-(3-difluoromethyl)-isoxazole | 2 | 3-CO₂Et, 6-Cl | 8.25 (d, 1H), 7.55-7.50 (m, 1H), 7.18 (t, 1H), 7.12 (d, 1H), 6.97 (d, 1H), 6.81 (s, 1H), 6.75 (t, 1H), 4.38 (q, 2H), 1.40 (t, 3H) |
| A142 | 0 | — | 2-(5-difluoromethyl-sulfanyl)-1,3,4-thiadiazole | 2 | 3-F, 5-Cl | 8.52 (d, 1H), 7.99 (s, 1H), 7.61 (d, 1H), 7.58-7.51 (m, 1H), 7.45-7.37 (m, 1H), 7.42 (t, 1H), 7.22 (d, 1H) |
| A143 | 0 | — | 3-methyl-imidazo-4-yl | 2 | 3-F, 5-Cl | 8.86 (br, 1H), 7.81 (s, 1H), 7.65-7.58 (m, 1H), 7.48 (d, 1H), 7.42-7.37 (m, 2H), 7.23 (t, 2H), 3.80 (s, 3H) |
| A144 | 0 | — | 2-methyl-pyrazol-3-yl | 2 | 3-F, 5-Cl | 7.98 (d, 1H), 7.29 (s, 1H), 7.46 (dd, 1H), 7.35-7.24 (m, 3H), 7.17 (d, 1H), 6.55 (s, 1H), 3.90 (s, 3H) |
| A145 | 0 | — | 5-iso-thiazole | 2 | 3-F, 5-Cl | 8.42 (s, 1H), 7.82-7.75 (m, 2H), 7.58-7.51 (m, 2H), 7.45 (t, 1H), 7.36 (t, 1H), 7.25 (d, 1H) |
| A146 | 0 | — | 5-thiazole | 2 | 3-F, 5-Cl | 8.73 (s, 1H), 8.12 (s, 1H), 7.80 (s, 1H), 7.69 (d, 1H), 7.49 (d, 1H), 7.42 (t, 1H), 7.32 (t, 1H), 7.21 (d, 1H) |
| A147 | 0 | — | 2-thiazole | 2 | 3-F, 5-Cl | 8.42 (d, 1H), 7.88 (s, 1H), 7.73 (s, 1H), 7.55 (d, 1H), 7.46 (t, 1H), 7.41-7.32 (m, 2H), 7.21 (d, 1H) |
| A148 | 0 | — | 3-furan | 2 | 3-F, 5-Cl | 7.78 (d, 2H), 7.56 (d, 1H), 7.47 (d, 1H), 7.39 (s, 1H), 7.36-7.21 (m, 2H), 7.16 (d, 1H), 6.69 (s, 1H) |
| A149 | 0 | — | 2-furan | 2 | 3-F, 5-Cl | 7.98-7.88 (m, 1H), 7.82 (s, 1H), 7.51 (d, 1H), 7.41 (s, 1H), 7.35-7.26 (m, 2H), 7.20-7.12 (m, 1H), 6.73 (s, 1H), 6.41 (s, 1H) |
| A154 | 1 | 3-F | 5-(3-difluoromethyl)-isoxazole | 2 | 5-CO₂Et, 6-Me | 8.25 (d, 1H), 7.50 (q, 1H), 7.13 (t, 1H), 7.09 (d, 1H), 6.84-6.78 (m, 2H), 6.75 (t, 1H), 4.37 (q, 2H), 2.61 (s, 3H), 1.37 (t, 3H) |

TABLE 1-continued

Examples of herbicidal compounds of the present invention.

| Compound | n | R¹ | Q | m | R² | $^1$H NMR (400 MHz, CDCl$_3$ unless stated) |
|---|---|---|---|---|---|---|
| A156 | 1 | 3-F | 5-(3-difluoromethyl)-isoxazole | 2 | 4-CO$_2$Et, 6-Br | 7.75 (s, 1H), 7.55-7.48 (m, 1H), 7.48 (s, 1H), 7.17 (t, 1H), 7.10 (d, 1H), 6.84 (s, 1H), 6.76 (t, 1H), 4.42 (q, 2H), 1.40 (t, 3H) |
| A158 | 1 | 3-CF$_3$ | 4-(trifluoromethyl)pyrazol-1-yl | 2 | 3-F, 5-Cl | 7.83-7.78 (m, 2H), 7.78-7.67 (m, 3H), 7.60 (dd, 1H), 7.41 (dd, 1H) |
| A159 | 1 | 3-Cl | 4-(trifluoromethyl)pyrazol-1-yl | 2 | 3-F, 5-Cl | 7.81-7.71 (m, 3H), 7.53-7.42 (m, 2H), 7.40 (dd, 1H), 7.29 (dd, 1H) |
| A160 | 1 | 3-CN | 5-(3-difluoromethyl)-isoxazole | 2 | 3,5-di-F | 7.81-7.71 (m, 2H), 7.66 (t, 1H), 7.55 (dd, 1H), 7.38 (ddd, 1H), 6.98 (s, 1H), 6.80 (t, 1H) |
| A161 | 1 | 3-CN | 5-(3-difluoromethyl)-isoxazole | 1 | 5-Cl | 8.03 (d, 1H), 7.78-7.68 (m, 2H), 7.65 (t, 1H), 7.51 (dd, 1H), 6.98 (d, 1H), 6.89 (s, 1H), 6.79 (t, 1H) |
| A162 | 1 | 3-CN | 5-(3-difluoromethyl)-isoxazole | 2 | 3-F, 5-Cl | 7.82 (d, 1H), 7.77 (dd, 1H), 7.67 (t, 1H), 7.59-7.54 (m, 2H), 6.98 (s, 1H), 6.80 (t, 1H) |
| A163 | 0 | — | 3-(5-difluoromethyl)-isoxazole | 2 | 3-F, 5-Cl | 7.97 (d, 1H), 7.82 (s, 1H), 7.58-7.50 (m, 2H), 7.38 (t, 1H), 7.22 (d, 1H), 6.95 (s, 1H), 6.73 (t, 1H) |
| A167 | 0 | — | pyrazol-1-yl | 2 | 3-F, 5-Cl | 7.86 (s, 1H), 7.82-7.71 (m, 2H), 7.60 (s, 1H), 7.42 (d, 1H), 7.40-7.32 (m, 2H), 7.32-7.22 (m, 1H), 6.31 (s, 1H) |
| A168 | 0 | — | (4-difluoromethyl)triazol-2-yl | 2 | 3-F, 5-Cl | 7.90 (d, 1H), 7.85 (s, 1H), 7.71 (s, 1H), 7.52 (t, 1H), 7.49-7.37 (m, 3H), 6.75 (t, 1H) |
| A169 | 0 | — | (4-difluoromethyl)triazol-1-yl | 2 | 3-F, 5-Cl | 8.25 (s, 1H), 7.84 (d, 1H), 7.80 (s, 1H), 7.55 (t, 1H), 7.52-7.40 (m, 2H), 7.36 (d, 1H), 6.88 (t, 1H) |
| A170 | 0 | — | 2(5-difluoromethyl)oxazole | 2 | 3-F, 5-Cl | 8.10 (d, 1H), 7.65 (s, 1H), 7.52 (t, 1H), 7.45 (d, 1H), 7.32 (t, 1H), 7.25-7.20 (m, 2H), 6.55 (t, 1H) |
| A171 | 1 | 4-Cl | thiazol-2-yl | 2 | 3-F, 5-Cl | 8.43 (s, 1H), 7.90 (d, 1H), 7.83 (s, 1H), 7.55 (d, 1H), 7.43-7.37 (m, 2H), 7.16 (d, 1H) |
| A172 | 1 | 3-F | 5-(3-difluoromethyl)-isoxazole | 2 | 5-Cl, 6-CN | 7.85 (d, 1H), 7.57-7.52 (m, 1H), 7.26-7.18 (m, 2H), 7.10 (d, 1H), 6.85 (d, 1H), 6.67 (t, 1H) |
| A173 | 1 | 3-F | 5-(3-difluoromethyl)-isoxazole | 2 | 3-CN, 4-Cl | 8.19 (s, 1H), 7.56-7.52 (m, 1H), 7.33 (s, 1H), 7.21 (t, 1H), 7.07 (d, 1H), 6.84 (d, 1H), 6.76 (t, 1H) |
| A174 | 1 | 3-F | thiazol-2-yl | 2 | 3-F, 5-Cl | 7.82 (s, 1H), 7.75 (s, 1H), 7.50-7.39 (m, 3H), 7.14 (t, 1H), 7.09 (d, 1H) |
| A175 | 1 | 3-Br | thiazol-2-yl | 2 | 3-F, 5-Cl | 7.84 (dd, 2H), 7.61 (d, 1H), 7.42 (s, 1H), 7.41-7.35 (m, 2H), 7.25-7.20 (m, 1H) |
| A176 | 1 | 3-Cl | thiazol-2-yl | 2 | 3-F, 5-Cl | 7.88-7.80 (m, 2H), 7.48-7.41 (m, 3H), 7.38 (d, 1H), 7.21-7.15 (m, 1H) |

BIOLOGICAL EXAMPLES

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 500 g/ha unless otherwise stated. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=81-100%; 4=61-80%; 3=41-60%; 2=21-40%; 1=0-20%).

TABLE B1

| | | Post-emergence Test | | | | | |
|---|---|---|---|---|---|---|---|
| Compound | Rate (g/ha) | AMARE | SOLNI | SETFA | LOLPE | ECHCG | IPOHE |
| A1 | 500 | 5 | 5 | 5 | 5 | 5 | 5 |
| A2 | 500 | 5 | 5 | 5 | 5 | 5 | 4 |
| A3 | 500 | 2 | 3 | 4 | 1 | 1 | 1 |
| A4 | 500 | 5 | 5 | 3 | 1 | 1 | 1 |
| A6 | 500 | 4 | 5 | 5 | 4 | 5 | 3 |
| A7 | 500 | 2 | 5 | 5 | 2 | 4 | 2 |
| A8 | 500 | 2 | 5 | 4 | 1 | 2 | 1 |
| A9 | 500 | 5 | 5 | 5 | 5 | 5 | 4 |
| A10 | 500 | 5 | 5 | 5 | 5 | 5 | 5 |
| A12 | 500 | 5 | 5 | 5 | 5 | 5 | 5 |
| A14 | 1000 | 5 | 5 | 5 | 5 | 5 | 4 |
| A15 | 1000 | 1 | 4 | 3 | 1 | 2 | 2 |
| A16 | 1000 | 4 | 5 | 5 | 5 | 5 | 5 |
| A17 | 1000 | 5 | 5 | 5 | 5 | 5 | 5 |
| A18 | 250 | 3 | 3 | 3 | 2 | 4 | 2 |
| A19 | 1000 | 5 | 5 | 5 | 5 | 5 | 5 |
| A20 | 1000 | 5 | 5 | 4 | 4 | 4 | 5 |
| A21 | 1000 | 4 | 3 | 4 | 3 | 4 | 3 |
| A22 | 1000 | 4 | 4 | 3 | 2 | 2 | 3 |
| A23 | 1000 | 5 | 5 | 5 | 5 | 5 | 5 |
| A24 | 1000 | 4 | 4 | 4 | 3 | 4 | 3 |
| A25 | 1000 | 5 | 5 | 5 | 5 | 4 | 4 |
| A26 | 1000 | 5 | 5 | 5 | 3 | 5 | 3 |
| A27 | 250 | 4 | 5 | 5 | 2 | 5 | 2 |
| A28 | 1000 | 5 | 4 | 1 | 1 | 1 | 1 |
| A29 | 1000 | 4 | 4 | 2 | 1 | 1 | 2 |
| A30 | 1000 | 5 | 5 | 5 | 5 | 5 | 5 |
| A31 | 1000 | 5 | 5 | 5 | 5 | 5 | 5 |
| A32 | 1000 | 5 | 5 | 5 | 5 | 5 | 5 |
| A33 | 1000 | 5 | 5 | 5 | 5 | 5 | 5 |
| A34 | 1000 | 5 | 5 | 5 | 5 | 5 | 5 |
| A35 | 1000 | 5 | 5 | 4 | 1 | 1 | 2 |
| A36 | 1000 | 5 | 5 | 5 | 4 | 4 | 2 |
| A37 | 1000 | 5 | 5 | 5 | 4 | 4 | 5 |
| A38 | 1000 | 5 | 5 | 1 | 1 | 1 | 1 |
| A39 | 1000 | 3 | 3 | 1 | 1 | 1 | 1 |
| A40 | 1000 | 3 | 4 | 1 | 1 | 1 | 1 |
| A41 | 1000 | 5 | 5 | 5 | 5 | 5 | 5 |
| A42 | 250 | 5 | 5 | 5 | 5 | 4 | 4 |
| A43 | 1000 | 5 | 5 | 5 | 5 | 4 | 4 |
| A44 | 1000 | 5 | 5 | 5 | 5 | 5 | 5 |
| A46 | 1000 | 5 | 5 | 4 | 3 | 3 | 2 |
| A47 | 1000 | 3 | 3 | 1 | 1 | 1 | 1 |
| A48 | 1000 | 5 | 5 | 2 | 1 | 1 | 2 |
| A49 | 1000 | 5 | 5 | 2 | 1 | 3 | 3 |
| A50 | 1000 | 3 | 5 | 3 | 1 | 2 | 1 |
| A51 | 1000 | 4 | 5 | 1 | 1 | 1 | 1 |
| A54 | 1000 | 3 | 5 | 5 | 4 | 3 | 1 |
| A55 | 1000 | 5 | 5 | 2 | 1 | 1 | 1 |
| A57 | 1000 | 5 | 5 | 4 | 1 | 1 | 2 |
| A58 | 1000 | 5 | 5 | 5 | 5 | 4 | 5 |
| A59 | 1000 | 5 | 5 | 5 | 4 | 3 | 5 |
| A60 | 1000 | 4 | 4 | 2 | 1 | 1 | 2 |
| A61 | 1000 | 5 | 5 | 2 | 1 | 1 | 2 |
| A62 | 1000 | 4 | 3 | 3 | 2 | 3 | 3 |
| A66 | 1000 | 5 | 5 | 2 | 1 | 3 | 2 |
| A69 | 1000 | 3 | 4 | 3 | 1 | 4 | 2 |
| A70 | 1000 | 3 | 4 | 2 | 1 | 3 | 1 |
| A71 | 1000 | 4 | 5 | 2 | 1 | 1 | 1 |
| A76 | 250 | 2 | 4 | 1 | 1 | 1 | 3 |
| A77 | 250 | 5 | 5 | 5 | 2 | 2 | 1 |
| A78 | 1000 | 3 | 4 | 1 | 1 | 1 | 1 |
| A80 | 1000 | 5 | 5 | 1 | 1 | 1 | 1 |
| A81 | 1000 | 5 | 4 | 4 | 1 | 4 | 2 |
| A82 | 1000 | 5 | 5 | 5 | 5 | 4 | 5 |
| A83 | 1000 | 5 | 4 | 4 | 4 | 4 | 2 |
| A84 | 1000 | 5 | 5 | 5 | 5 | 5 | 5 |
| A85 | 1000 | 5 | 5 | 5 | 5 | 5 | 5 |
| A86 | 1000 | 4 | 4 | 4 | 4 | 4 | 4 |
| A87 | 1000 | 4 | 4 | 5 | 3 | 3 | 3 |
| A88 | 1000 | 5 | 4 | 4 | 3 | 4 | 2 |
| A89 | 1000 | 5 | 4 | 5 | 3 | 4 | 4 |
| A90 | 1000 | 5 | 4 | 5 | 4 | 4 | 4 |
| A91 | 1000 | 4 | 4 | 4 | 4 | 4 | 4 |
| A92 | 1000 | 4 | 4 | 4 | 4 | 4 | 4 |

TABLE B1-continued

Post-emergence Test

| Compound | Rate (g/ha) | AMARE | SOLNI | SETFA | LOLPE | ECHCG | IPOHE |
|---|---|---|---|---|---|---|---|
| A93 | 1000 | 5 | 3 | 5 | 3 | 4 | 3 |
| A94 | 1000 | 4 | 4 | 3 | 2 | 2 | 1 |
| A95 | 1000 | 4 | 4 | 4 | 3 | 3 | 1 |
| A97 | 1000 | 5 | 4 | 5 | 3 | 4 | 4 |
| A98 | 1000 | 4 | 4 | 5 | 3 | 4 | 3 |
| A99 | 1000 | 5 | 4 | 4 | 3 | 4 | 2 |
| A100 | 250 | 5 | NT | 5 | NT | 5 | 2 |
| A101 | 1000 | 5 | 5 | 5 | 4 | 4 | 5 |
| A102 | 1000 | 5 | 5 | 5 | 4 | 4 | 5 |
| A103 | 1000 | 5 | 5 | 5 | 5 | 4 | 5 |
| A104 | 1000 | 4 | 5 | 4 | 3 | 4 | 4 |
| A105 | 1000 | 5 | 5 | 5 | 4 | 4 | 5 |
| A106 | 1000 | 5 | 5 | 5 | 5 | 4 | 4 |
| A107 | 1000 | 5 | 5 | 5 | 3 | 4 | 4 |
| A108 | 1000 | 5 | 4 | 4 | 4 | 4 | 3 |
| A109 | 1000 | 5 | 5 | 5 | 3 | 4 | 4 |
| A110 | 1000 | 5 | 5 | 5 | 4 | 4 | 4 |
| A111 | 1000 | 5 | 5 | 5 | 4 | 4 | 4 |
| A112 | 1000 | 4 | 4 | 4 | 3 | 3 | 3 |
| A113 | 1000 | 5 | 4 | 5 | 5 | 4 | 5 |
| A114 | 1000 | 5 | 5 | 5 | 4 | 4 | 5 |
| A115 | 1000 | 5 | 5 | 5 | 4 | 4 | 5 |
| A116 | 1000 | 5 | 5 | 5 | 5 | 4 | 5 |
| A117 | 1000 | 5 | 4 | 4 | 4 | 4 | 5 |
| A118 | 1000 | 5 | 5 | 5 | 5 | 5 | 5 |
| A119 | 1000 | 5 | 5 | 5 | 5 | 4 | 5 |
| A120 | 1000 | 5 | 5 | 5 | 3 | 4 | 4 |
| A121 | 1000 | 4 | 4 | 3 | 1 | 3 | 2 |
| A159 | 1000 | 5 | 5 | 5 | 4 | 3 | 4 |
| A160 | 1000 | 5 | 5 | 5 | 5 | 5 | 5 |
| A161 | 1000 | 5 | 5 | 5 | 5 | 5 | 5 |
| A162 | 1000 | 5 | 5 | 5 | 5 | 4 | 5 |
| A163 | 250 | 5 | NT | 5 | NT | 5 | 3 |
| A169 | 250 | 5 | NT | 5 | NT | 5 | 5 |

NT = Not Tested

TABLE B2

Pre-emergence Test

| Compound | Rate (g/ha) | AMARE | SOLNI | SETFA | LOLPE | ECHCG | IPOHE |
|---|---|---|---|---|---|---|---|
| A1 | 500 | 5 | 5 | 5 | 5 | 5 | 5 |
| A2 | 500 | 5 | 4 | 5 | 4 | 5 | 2 |
| A3 | 500 | 3 | 3 | 3 | 1 | 3 | 1 |
| A4 | 500 | 3 | 3 | 2 | 1 | 2 | 1 |
| A6 | 500 | 5 | 5 | 5 | 4 | 4 | 2 |
| A7 | 500 | 5 | 5 | 4 | 1 | 4 | 1 |
| A8 | 500 | 5 | 4 | 3 | 1 | 2 | 1 |
| A9 | 500 | 5 | 5 | 5 | 4 | 5 | 3 |
| A10 | 500 | 5 | 5 | 5 | 5 | 5 | 5 |
| A12 | 500 | 5 | 5 | 5 | 5 | 5 | 5 |
| A14 | 1000 | 5 | 5 | 5 | 5 | 5 | 3 |
| A15 | 1000 | 5 | 4 | 5 | 3 | 5 | 1 |
| A16 | 1000 | 5 | 5 | 5 | 5 | 5 | 5 |
| A17 | 1000 | 5 | 5 | 5 | 5 | 5 | 5 |
| A18 | 250 | 5 | 5 | 5 | 1 | 5 | 1 |
| A19 | 1000 | 5 | 5 | 5 | 5 | 5 | 5 |
| A20 | 1000 | 4 | 3 | 5 | 5 | 5 | 3 |
| A21 | 1000 | 5 | 2 | 5 | 4 | 5 | 2 |
| A22 | 1000 | 5 | 1 | 3 | 1 | 3 | 1 |
| A23 | 1000 | 5 | 4 | 5 | 5 | 5 | 5 |
| A24 | 1000 | 5 | 3 | 5 | 4 | 5 | 3 |
| A25 | 1000 | 5 | 5 | 5 | 5 | 5 | 5 |
| A26 | 1000 | 5 | 5 | 5 | 5 | 5 | 4 |
| A27 | 250 | 5 | 5 | 4 | 3 | 5 | 1 |
| A28 | 1000 | 3 | 1 | 1 | 1 | 1 | 1 |
| A29 | 1000 | 5 | 3 | 4 | 1 | 1 | 1 |
| A30 | 1000 | 5 | 5 | 5 | 5 | 5 | 5 |
| A31 | 1000 | 5 | 5 | 5 | 5 | 5 | 5 |
| A32 | 1000 | 5 | 5 | 5 | 4 | 5 | 5 |

TABLE B2-continued

| | | Pre-emergence Test | | | | | |
|---|---|---|---|---|---|---|---|
| Compound | Rate (g/ha) | AMARE | SOLNI | SETFA | LOLPE | ECHCG | IPOHE |
| A33 | 1000 | 5 | 5 | 5 | 4 | 5 | 2 |
| A34 | 1000 | 5 | 5 | 5 | 5 | 5 | 5 |
| A35 | 1000 | 3 | 5 | 5 | 1 | 5 | 1 |
| A36 | 1000 | 5 | 5 | 5 | 3 | 5 | 5 |
| A37 | 1000 | 5 | 5 | 5 | 5 | 5 | 5 |
| A38 | 1000 | 4 | 1 | 1 | 1 | 1 | 1 |
| A39 | 1000 | 5 | 1 | 1 | 1 | 1 | 1 |
| A40 | 1000 | 2 | 1 | 1 | 1 | 1 | 1 |
| A41 | 1000 | 5 | 5 | 5 | 5 | 5 | 3 |
| A42 | 250 | 5 | 4 | 5 | 5 | 5 | 3 |
| A43 | 1000 | 5 | 5 | 5 | 5 | 5 | 4 |
| A44 | 1000 | 5 | 5 | 5 | 5 | 5 | 5 |
| A46 | 1000 | 4 | 1 | 5 | 1 | 4 | 1 |
| A47 | 1000 | 1 | 1 | 1 | 1 | 1 | 1 |
| A48 | 1000 | 1 | 1 | 1 | 1 | 1 | 1 |
| A49 | 1000 | 5 | 5 | 5 | 1 | 3 | 1 |
| A50 | 1000 | 4 | 4 | 4 | 1 | 1 | 1 |
| A51 | 1000 | 1 | 1 | 1 | 1 | 1 | 1 |
| A54 | 1000 | 5 | 5 | 5 | 5 | 3 | 1 |
| A55 | 1000 | 2 | 2 | 4 | 1 | 1 | 1 |
| A57 | 1000 | 5 | 4 | 5 | 1 | 1 | NT |
| A58 | 1000 | 5 | 5 | 5 | 5 | 5 | 5 |
| A59 | 1000 | 5 | 5 | 5 | 4 | 2 | 2 |
| A60 | 1000 | 5 | 1 | 1 | 1 | 2 | 1 |
| A61 | 1000 | 1 | 1 | 2 | 1 | 1 | 1 |
| A62 | 1000 | 4 | 1 | 1 | 1 | 1 | 1 |
| A69 | 1000 | 3 | 1 | 1 | 1 | 1 | 1 |
| A70 | 1000 | 2 | 1 | 1 | 1 | 1 | 1 |
| A71 | 1000 | 5 | 1 | 1 | 1 | 1 | 1 |
| A77 | 250 | 5 | 4 | 5 | 2 | 2 | 1 |
| A78 | 1000 | 1 | 1 | 2 | 1 | 1 | 1 |
| A80 | 1000 | 2 | 1 | 1 | 1 | 1 | 1 |
| A81 | 1000 | 5 | 3 | 4 | 1 | 4 | 2 |
| A82 | 1000 | 5 | 4 | 5 | 5 | 5 | 5 |
| A83 | 1000 | 4 | 1 | 2 | 1 | 2 | 1 |
| A84 | 1000 | 5 | 4 | 5 | 5 | 5 | 5 |
| A85 | 1000 | 5 | 5 | 5 | 5 | 5 | 5 |
| A86 | 1000 | 4 | 2 | 5 | 4 | 5 | 1 |
| A87 | 1000 | 4 | 3 | 5 | 4 | 4 | 1 |
| A88 | 1000 | 5 | 4 | 5 | 4 | 5 | 1 |
| A89 | 1000 | 4 | 2 | 4 | 2 | 4 | 3 |
| A90 | 1000 | 4 | 4 | 5 | 5 | 5 | 3 |
| A91 | 1000 | 4 | 3 | 5 | 4 | 5 | 4 |
| A92 | 1000 | 4 | 2 | 5 | 5 | 1 | 4 |
| A93 | 1000 | 4 | 4 | 4 | 3 | 4 | 3 |
| A94 | 1000 | 4 | 2 | 2 | 2 | 3 | 1 |
| A95 | 1000 | 4 | 1 | 3 | 1 | 4 | 1 |
| A97 | 1000 | 4 | 2 | 4 | 2 | 3 | 2 |
| A98 | 1000 | 4 | 3 | 5 | 3 | 5 | 1 |
| A99 | 1000 | 5 | 1 | 4 | 3 | 4 | 1 |
| A100 | 250 | 5 | NT | 5 | NT | 2 | 1 |
| A101 | 1000 | 5 | 4 | 5 | 5 | 5 | 5 |
| A102 | 1000 | 5 | 4 | 5 | 5 | 5 | 4 |
| A103 | 1000 | 5 | 3 | 5 | 5 | 5 | 5 |
| A104 | 1000 | 4 | 2 | 5 | 4 | 4 | 4 |
| A105 | 1000 | 5 | 5 | 5 | 5 | 5 | 5 |
| A106 | 1000 | 4 | 3 | 5 | 5 | 5 | 3 |
| A107 | 1000 | 5 | 2 | 5 | 2 | 4 | 3 |
| A108 | 1000 | 4 | 4 | 5 | 5 | 5 | 1 |
| A109 | 1000 | 4 | 3 | 4 | 2 | 2 | 1 |
| A110 | 1000 | 5 | 4 | 5 | 4 | 4 | 4 |
| A111 | 1000 | 5 | 4 | 5 | 4 | 5 | 1 |
| A112 | 1000 | 5 | 2 | 5 | 3 | 4 | 1 |
| A113 | 1000 | 5 | 4 | 5 | 5 | 5 | 4 |
| A114 | 1000 | 5 | 4 | 5 | 5 | 5 | 5 |
| A115 | 1000 | 5 | 4 | 5 | 5 | 5 | 5 |
| A116 | 1000 | 5 | 4 | 5 | 5 | 5 | 4 |
| A117 | 1000 | 5 | 2 | 5 | 4 | 4 | 5 |
| A118 | 1000 | 5 | 4 | 5 | 5 | 5 | 4 |
| A119 | 1000 | 5 | 4 | 5 | 5 | 5 | 4 |
| A120 | 1000 | 5 | 4 | 5 | 2 | 5 | 3 |
| A121 | 1000 | 4 | 1 | 3 | 1 | 4 | 1 |
| A126 | 250 | 5 | NT | 3 | NT | 4 | 1 |
| A159 | 1000 | 5 | 5 | 5 | 5 | 5 | 2 |
| A160 | 1000 | 5 | 4 | 5 | 5 | 5 | 5 |

TABLE B2-continued
| | | Pre-emergence Test | | | | | |
|---|---|---|---|---|---|---|---|
| Compound | Rate (g/ha) | AMARE | SOLNI | SETFA | LOLPE | ECHCG | IPOHE |
| A161 | 1000 | 5 | 4 | 5 | 5 | 5 | 5 |
| A162 | 1000 | 5 | 4 | 5 | 5 | 5 | 5 |
| A163 | 250 | 5 | NT | 5 | NT | 4 | 1 |
| A169 | 250 | 5 | NT | 5 | NT | 5 | 5 |
NT = Not Tested
BIOLOGICAL EXAMPLES
TABLE B3
| TEST | | Compound | Rate | GLYMA | AMARE |
|---|---|---|---|---|---|
| 1 | PYRIMIDINE COMPARATOR WO2015/108779 CMP 55 | 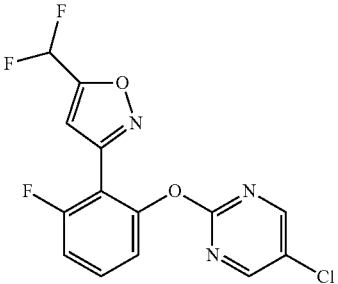 [SMILES: Fc1cccc(Oc2ncc(Cl)cn2)c1-c1cc(C(F)F)on1] | 500<br>250 | 90<br>70 | 100<br>100 |
| | A30 | 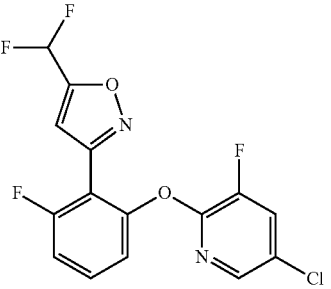 [SMILES: Fc1cc(Cl)cnc1Oc1cccc(F)c1-c1cc(C(F)F)on1] | 500<br>250 | 0<br>0 | 100<br>100 |
| 2 | PYRIMIDINE COMPARATOR WO2015/108779 CMP 144 | 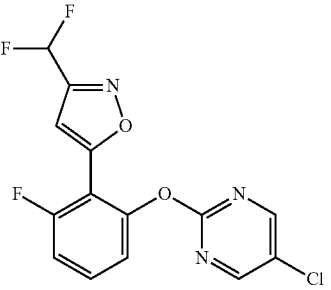 [SMILES: Fc1cccc(Oc2ncc(Cl)cn2)c1-c1cc(C(F)F)no1] | 500<br>250 | 90<br>10 | 100<br>100 |
| | A1 | 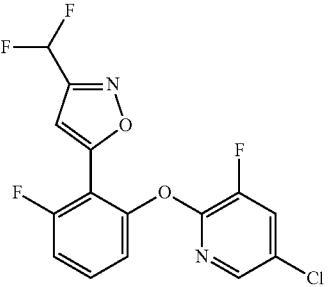 [SMILES: Fc1cc(Cl)cnc1Oc1cccc(F)c1-c1cc(C(F)F)no1] | 500<br>250 | 0<br>0 | 100<br>100 |

TABLE B3-continued
| | | Comparative Test | | | |
|---|---|---|---|---|---|
| TEST | Compound | | Rate | GLYMA | AMARE |
| | A37 | 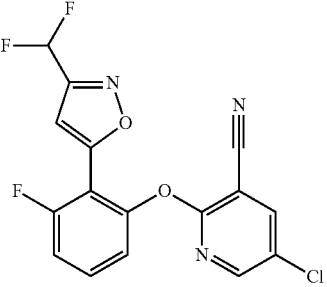 [SMILES: N#Cc1cc(Cl)cnc1Oc1cccc(F)c1-c1cc(C(F)F)no1] | 500<br>250 | 0<br>0 | 100<br>100 |
| 3 | PYRIMIDINE<br>COMPARATOR<br>WO2015/108779<br>CMP 145 | 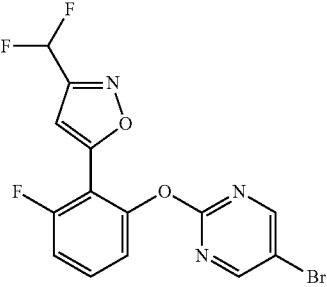 [SMILES: Fc1cccc(Oc2ncc(Br)cn2)c1-c1cc(C(F)F)no1] | 500<br>250 | 40<br>10 | 100<br>100 |
| | A20 | 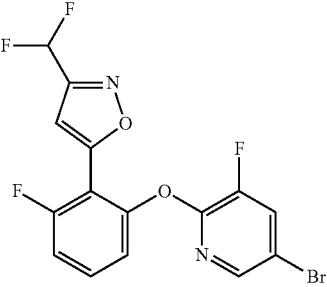 [SMILES: Fc1cc(Br)cnc1Oc1cccc(F)c1-c1cc(C(F)F)no1] | 500<br>250 | 0<br>0 | 100<br>100 |
| 4 | PYRIMIDINE<br>COMPARATOR<br>WO2015/089003<br>CMP 58 | 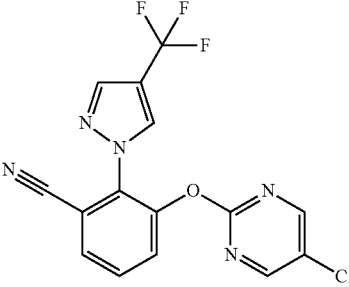 | 500<br>250 | 100<br>90 | 100<br>100 |
| | A33 | 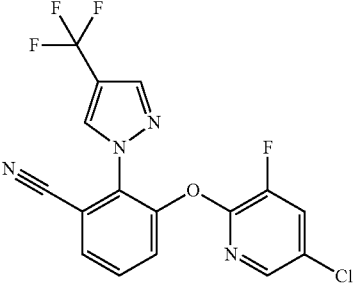 [SMILES: N#Cc1cccc(Oc2ncc(Cl)cc2F)c1-n1cc(C(F)(F)F)cn1] | 500<br>250 | 0<br>0 | 100<br>100 |

TABLE B3-continued

| | Comparative Test | | | |
|---|---|---|---|---|
| TEST | Compound | Rate | GLYMA | AMARE |
| 5 | PYRIMIDINE COMPARATOR 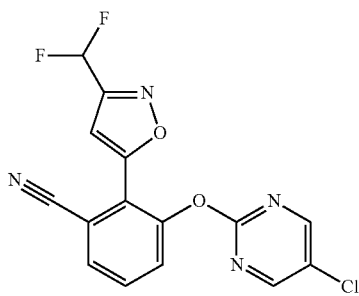 [SMILES: N#Cc1cccc(Oc2ncc(Cl)cn2)c1-c1cc(C(F)F)no1] | 500 250 | 100 90 | 100 100 |
| A162 | 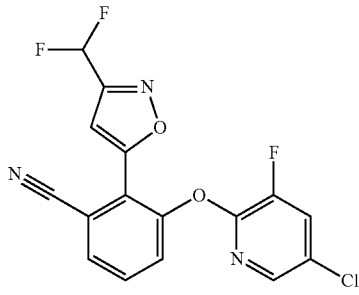 [SMILES: N#Cc1cccc(Oc2ncc(Cl)cc2F)c1-c1cc(C(F)F)no1] | 500 250 | 0 0 | 100 100 |

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (CAS RN 34590-94-8) and 0.2% X-77 (CAS RN 11097-66-8). The test plants were then grown in a glasshouse under controlled conditions in a glasshouse (at 24/16° C., day/night; 14 hours light; 65% humidity) and watered twice daily. After 21 days the test was evaluated (100=total damage to plant; 0=no damage to plant).
Test Plants:
Weed species: *Amaranthus retroflexus* (AMARE)
Crops: Soybean (*Glycine max* (GLYMA))

The results demonstrate that the pyridine compounds of the present invention exhibit much reduced herbicidal damage to the crop (soybean) compared to the pyrimidine compounds of the prior art whilst weed (AMARE) control remains comparable.

The invention claimed is:

1. A compound of Formula (I):

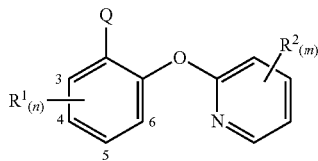

(I)

or an agronomically acceptable salt thereof, wherein

Q is a 5-membered aromatic heterocyclic ring which is optionally substituted by 1 or 2 $R^3$ substituents independently selected from the group consisting of $C_1$-$C_4$alkyl, $C_2$-$C_4$alkenyl, $C_2$-$C_4$alkynyl, cyclopropyl, $C_1$-$C_4$haloalkyl, $C_1$-$C_2$alkoxy-, $C_1$-$C_2$haloalkoxy-, halogen, —C(O)$C_1$-$C_4$alkyl, $NO_2$, —$CH_2CN$, —CN and —S(O)$_p$$C_1$-$C_4$alkyl;

each $R^1$ is independently selected from the group consisting of halogen, —CN, nitro, $C_1$-$C_4$alkyl, $C_2$-$C_4$alkenyl, $C_2$-$C_4$alkynyl, $C_1$-$C_4$haloalkyl, $C_1$-$C_4$alkoxy-, $C_1$-$C_4$haloalkoxy- and —S(O)$_p$$C_1$-$C_4$alkyl;

each $R^2$ is independently selected from the group consisting of halogen, —CN, $NO_2$, $C_1$-$C_4$alkyl, $C_1$-$C_4$haloalkyl, $C_3$-$C_6$cycloalkyl, $C_2$-$C_4$alkenyl, $C_2$-$C_4$alkynyl, —S(O)$_p$$C_1$-$C_4$alkyl, $C_1$-$C_4$alkoxy, —C(O)$C_1$-$C_4$alkyl, —C(O)O$C_1$-$C_4$alkyl and $C_1$-$C_4$haloalkoxy;

m=0, 1 or 2;
n=0, 1 or 2; and
p=0, 1 or 2, with the proviso that Q is not 1,3,4-oxadiazol-2-yl or a C-linked tetrazolyl and wherein if Q is 2-thienyl or 2-furyl then said 2-thienyl or 2-furyl is substituted by 1 or 2 R3 independently selected from the group consisting of C1-C2haloalkyl, halogen and —CN.

2. The compound of Formula (I) according to claim 1, wherein Q is selected from the group consisting of

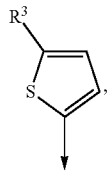

(Q1)

-continued
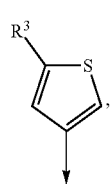
(Q2)
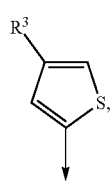
(Q3)
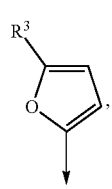
(Q4)
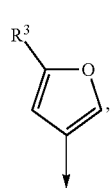
(Q5)
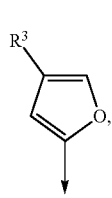
(Q6)
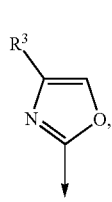
(Q7)
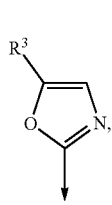
(Q8)
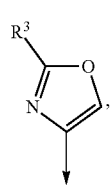
(Q9)
-continued
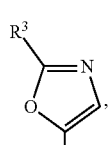
(Q10)
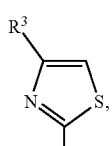
(Q11)
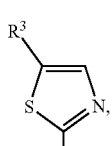
(Q12)
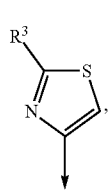
(Q13)
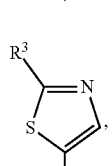
(Q14)
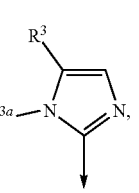
(Q15)
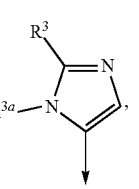
(Q16)
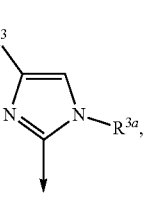
(Q17)

-continued
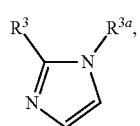 (Q18)
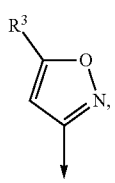 (Q19)
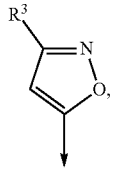 (Q20)
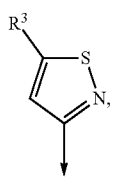 (Q21)
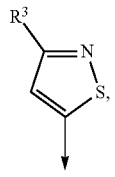 (Q22)
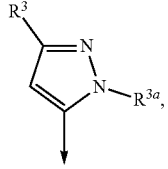 (Q23)
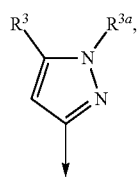 (Q24)
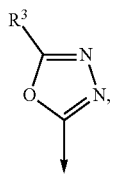 (Q25)
-continued
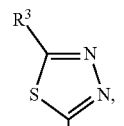 (Q26)
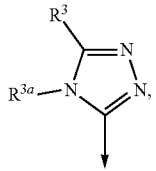 (Q27)
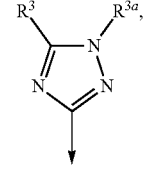 (Q28)
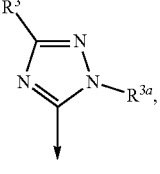 (Q29)
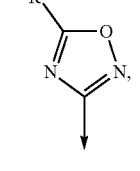 (Q30)
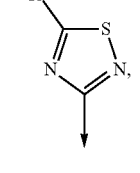 (Q31)
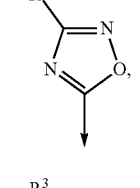 (Q32)
(Q33)
(Q34)

-continued

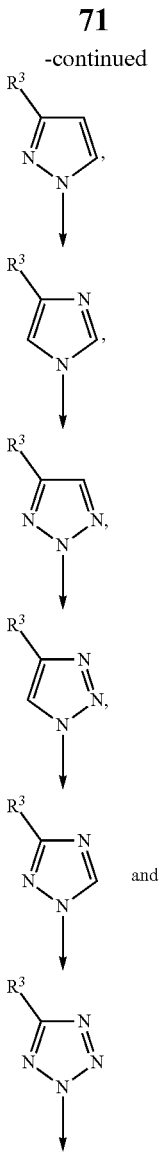

(Q35), (Q36), (Q37), (Q38), (Q39) and (Q40)

wherein $R^3$ is selected from the group consisting of hydrogen, $C_1$-$C_4$alkyl, $C_2$-$C_4$alkenyl, $C_2$-$C_4$alkynyl, cyclopropyl, $C_1$-$C_2$haloalkyl, $C_1$-$C_2$alkoxy-, $C_1$-$C_2$haloalkoxy-, halogen, —C(O)$C_1$-$C_4$alkyl, $NO_2$, —$CH_2CN$, —CN and —S(O)$_p$$C_1$-$C_4$alkyl; and $R^{3a}$ is hydrogen or $C_1$-$C_2$ alkyl with the proviso that Q is not 1,3,4-oxadiazol-2-yl or a C-linked tetrazolyl and wherein if Q is 2-thienyl or 2-furyl then said 2-thienyl or 2-furyl is substituted by 1 or 2 $R^3$ independently selected from the group consisting of $C_1$-$C_2$haloalkyl, halogen and —CN.

3. The compound of Formula (I) according to claim 1, wherein Q is selected from the group consisting of Q19, Q20 and Q34.

4. The compound of Formula (I) according to claim 1, wherein Q is Q20.

5. The compound according to claim 1, wherein n is 1 and $R^1$ is fluorine.

6. The compound according to claim 5, wherein $R^1$ is 3-fluoro.

7. The compound according to claim 1, wherein m is 1 or 2 and $R^2$ is independently selected from the group consisting of fluorine, nitro, cyano and trifluoromethyl.

8. The compound according to claim 1, wherein $R^3$ is difluoromethyl or trifluoromethyl.

9. A herbicidal composition comprising a compound according to claim 1 and an agriculturally acceptable formulation adjuvant.

10. The herbicidal composition according to claim 9, further comprising at least one additional pesticide.

11. The herbicidal composition according to claim 10, wherein the additional pesticide is a herbicide or herbicide safener.

12. A method of controlling weeds at a locus comprising application to the locus of a weed controlling amount of a composition according to claim 9.

13. A compound selected from Compounds A1-A176 as defined below:

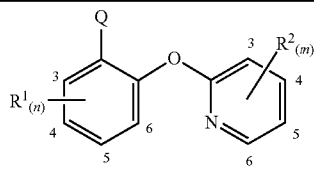

| Compound | n | $R^1$ | Q | m | $R^2$ |
|---|---|---|---|---|---|
| A1 | 1 | 3-F | 5-(3-difluoromethyl)-isoxazole | 2 | 3-F, 5-Cl |
| A2 | 1 | 3-F | 5-(3-difluoromethyl)-isoxazole | 1 | 5-$NO_2$ |
| A3 | 1 | 3-F | 2-(5-trifluoromethyl)-oxazole | 2 | 3-F, 5-Cl |
| A4 | 1 | 3-F | 5-(3-difluoromethyl)-isoxazole | 2 | 3-Cl, 5-Cl |
| A5 | 1 | 3-F | 5-(3-difluoromethyl)-isoxazole | 1 | 6-Cl |
| A6 | 1 | 3-F | 5-(3-difluoromethyl)-isoxazole | 1 | 5-$CF_3$ |
| A7 | 1 | 3-F | 5-(3-difluoromethyl)-isoxazole | 1 | 6-F |
| A8 | 1 | 3-F | 5-(3-difluoromethyl)-isoxazole | 1 | 4-$CF_3$ |
| A9 | 1 | 3-F | 5-(3-difluoromethyl)-isoxazole | 1 | 5-Cl |
| A10 | 1 | 3-F | 5-(3-difluoromethyl)-isoxazole | 2 | 3-F, 5-F |
| A11 | 1 | 3-F | 5-(3-difluoromethyl)-isoxazole | 2 | 4-Cl, 6-Cl |
| A12 | 1 | 3-F | 5-(3-difluoromethyl)-isoxazole | 1 | 5-CN |
| A13 | 1 | 3-F | 5-(3-difluoromethyl)-isoxazole | 2 | 3-F, 4-Cl |
| A14 | 0 | — | 4-(trifluoromethyl)pyrazol-1-yl | 1 | 5-$NO_2$ |

-continued

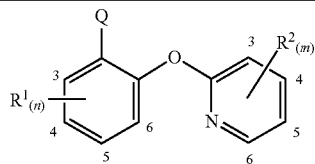

| Compound | n | R¹ | Q | m | R² |
| --- | --- | --- | --- | --- | --- |
| A15 | 0 | — | 4-(trifluoromethyl)pyrazol-1-yl | 1 | 5-$CF_3$ |
| A16 | 0 | — | 4-(trifluoromethyl)pyrazol-1-yl | 2 | 3-F, 5-Cl |
| A17 | 0 | — | 4-(trifluoromethyl)pyrazol-1-yl | 1 | 5-Cl |
| A18 | 0 | — | 4-(trifluoromethyl)pyrazol-1-yl | 2 | 3-F, 5-F |
| A19 | 0 | — | 4-(trifluoromethyl)pyrazol-1-yl | 1 | 5-CN |
| A20 | 1 | 3-F | 5-(3-difluoromethyl)-isoxazole | 2 | 3-F, 5-Br |
| A21 | 1 | 3-F | 5-(3-difluoromethyl)-isoxazole | 2 | 3-F, 5-$CF_3$ |
| A22 | 1 | 3-F | 5-(3-difluoromethyl)-isoxazole | 2 | 3-F, 5-$NO_2$ |
| A23 | 1 | 3-F | 5-(3-difluoromethyl)-isoxazole | 2 | 3-F, 5-CN |
| A24 | 0 | — | 4-(chloro)pyrazol-1-yl | 2 | 3-F, 5-Cl |
| A25 | 1 | 3-F | 3-(5-trifluoromethyl)-isoxazole | 2 | 3-F, 5-Cl |
| A26 | 0 | — | 4-cyanopyrazol-1-yl | 2 | 3-F, 5-Cl |
| A27 | 0 | — | 4-bromopyrazol-1-yl | 2 | 3-F, 5-Cl |
| A28 | 0 | — | imidazo-1-yl | 2 | 3-F, 5-Cl |
| A29 | 0 | — | 1,2,4-triazo-1-yl | 2 | 3-F, 5-Cl |
| A30 | 1 | 3-F | 3-(5-difluoromethyl)-isoxazole | 2 | 3-F, 5-Cl |
| A31 | 1 | 3-F | 5-(3-trifluoromethyl)-isoxazole | 2 | 3-F, 5-Cl |
| A32 | 1 | 3-CN | 4-(trifluoromethyl)pyrazol-1-yl | 1 | 5-Cl |
| A33 | 1 | 3-CN | 4-(trifluoromethyl)pyrazol-1-yl | 2 | 3-F, 5-Cl |
| A34 | 1 | 3-CN | 4-(trifluoromethyl)pyrazol-1-yl | 2 | 3,5-di-F |
| A35 | 1 | 3-F | 2-(5-difluoromethyl)-oxazole | 2 | 3-F, 5-Cl |
| A36 | 1 | 3-OMe | 4-(trifluoromethyl)pyrazol-1-yl | 2 | 3-F, 5-Cl |
| A37 | 1 | 3-F | 5-(3-difluoromethyl)-isoxazole | 2 | 3-CN, 5-Cl |
| A38 | 1 | 3-F | 5-(3-difluoromethyl)-isoxazole | 2 | 3-$NO_2$, 5-Cl |
| A39 | 1 | 3-F | 5-(3-difluoromethyl)-isoxazole | 2 | 3-F, 5-$SO_2$Me |
| A40 | 1 | 3-F | 5-(3-difluoromethyl)-isoxazole | 1 | 5-$SO_2$Me |
| A41 | 1 | 3-F | 5-(3-difluoromethyl)-isoxazole | 1 | 5-Br |
| A42 | 1 | 3-Cl | 5-(3-difluoromethyl)-isoxazole | 2 | 3-F, 5-Cl |
| A43 | 0 | — | 5-(3-difluoromethyl)-isoxazole | 2 | 3-F, 5-Cl |
| A44 | 1 | 3-Br | 5-(3-difluoromethyl)-isoxazole | 2 | 3-F, 5-Cl |
| A45 | 0 | — | 1,2,3-triazo-2-yl | 2 | 3-F, 5-Cl |
| A46 | 1 | 3-$NO_2$ | 4-(trifluoromethyl)pyrazol-1-yl | 2 | 3-F, 5-Cl |
| A47 | 1 | 3-F | 5-(3-difluoromethyl)-isoxazole | 1 | 6-$CF_3$ |
| A48 | 1 | 3-F | 5-(3-difluoromethyl)-isoxazole | 1 | 6-$OCF_2$H |
| A49 | 1 | 3-F | 5-(3-difluoromethyl)-isoxazole | 1 | 3-CN |
| A50 | 1 | 3-F | 5-(3-difluoromethyl)-isoxazole | 2 | 5,6-di-F |
| A51 | 1 | 3-F | 5-(3-difluoromethyl)-isoxazole | 2 | 3-Cl, 5-$CF_3$ |
| A53 | 1 | 3-F | 5-(3-difluoromethyl)-isoxazole | 1 | 3-F |
| A54 | 1 | 3-Me | 4-(trifluoromethyl)pyrazol-1-yl | 2 | 3-F, 5-Cl |
| A55 | 1 | 3-F | 5-(3-difluoromethyl)-isoxazole | 1 | 6-$CHF_2$ |
| A56 | 1 | 3-F | 5-(3-difluoromethyl)-isoxazole | 1 | 4-Et |
| A57 | 1 | 3-I | 4-(trifluoromethyl)pyrazol-1-yl | 1 | 3-F, 5-Cl |
| A58 | 1 | 3-F | 4-(trifluoromethyl)pyrazol-1-yl | 1 | 3-F, 5-Cl |
| A59 | 1 | 3-Br | 4-(trifluoromethyl)pyrazol-1-yl | 1 | 3-F, 5-Cl |
| A60 | 1 | 3-F | 5-(3-difluoromethyl)-isoxazole | 1 | 4-Cl |
| A61 | 2 | 3,4-di-Br | 4-(trifluoromethyl)pyrazol-1-yl | 2 | 3-F, 5-Cl |
| A62 | 1 | 3-F | 5-(3-difluoromethyl)-isoxazole | 1 | 4-$OCF_3$ |
| A63 | 1 | 3-F | 5-(3-difluoromethyl)-isoxazole | 2 | 3-$NO_2$, 4-Me |
| A64 | 1 | 3-F | 5-(3-difluoromethyl)-isoxazole | 1 | 5-$OCF_3$ |
| A65 | 1 | 3-F | 5-(3-difluoromethyl)-isoxazole | 1 | 4-Me |
| A66 | 0 | — | 5-chloro-2-thienyl | 2 | 3-F, 5-Cl |
| A67 | 0 | — | 5-cyano-2-thienyl | 2 | 3-F, 5-Cl |
| A69 | 0 | — | 5-chloro-3-thienyl | 2 | 3-F, 5-Cl |
| A70 | 0 | — | 3-thienyl | 2 | 3-F, 5-Cl |
| A71 | 0 | — | 4-methoxy-2-thienyl | 2 | 3-F, 5-Cl |
| A72 | 0 | — | 2,5-dimethylpyrazol-3-yl | 2 | 3-F, 5-Cl |
| A73 | 0 | — | 2-methyl-5-(trifluoromethyl)pyrazol-3-yl | 2 | 3-F, 5-Cl |
| A74 | 0 | — | 5-methylsulfanyl-1,3,4-thiadiazol-2-yl | 2 | 3-F, 5-Cl |
| A75 | 0 | — | 5-methylsulfonyl-1,3,4-thiadiazol-2-yl | 0 | 3-F, 5-Cl |
| A76 | 1 | 3-F | 5-(3-difluoromethyl)-isoxazole | 2 | 3-Me, 6-CN |
| A77 | 1 | 3-F | 5-(3-difluoromethyl)-isoxazole | 1 | 5-$CHF_2$ |
| A78 | 1 | 3-F | 5-(3-difluoromethyl)-isoxazole | 2 | 4, 5-di-$CF_3$ |
| A79 | 1 | 3-F | 5-(3-difluoromethyl)-isoxazole | 1 | 6-CN |
| A80 | 1 | 3-F | 5-(3-difluoromethyl)-isoxazole | 2 | 3-$CF_3$, 6-Cl |
| A81 | 0 | — | 4-(trifluoromethyl)triazol-2-yl | 2 | 3-F, 5-Cl |
| A82 | 0 | — | 4-(trifluoromethyl)triazole-1-yl | 2 | 3-F, 5-Cl |
| A83 | 1 | 6-Br | 5-(3-difluoromethyl)-isoxazole | 2 | 3-F, 5-Cl |
| A84 | 1 | 3-Br | 5-(3-difluoromethyl)-isoxazole | 2 | 3-CN, 5-F |
| A85 | 1 | 3-Cl | 5-(3-difluoromethyl)-isoxazole | 2 | 3-CN, 5-F |

-continued

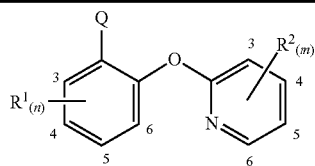

| Compound | n | R¹ | Q | m | R² |
|---|---|---|---|---|---|
| A86 | 1 | 3-Br | 5-(3-difluoromethyl)-isoxazole | 1 | 4-Cl |
| A87 | 1 | 3-Br | 5-(3-difluoromethyl)-isoxazole | 1 | 4-CN |
| A88 | 1 | 3-Br | 5-(3-difluoromethyl)-isoxazole | 1 | 5-NO₂ |
| A89 | 1 | 3-Br | 5-(3-difluoromethyl)-isoxazole | 2 | 3,5-di-Cl |
| A90 | 1 | 3-Br | 5-(3-difluoromethyl)-isoxazole | 1 | 5-CF₃ |
| A91 | 1 | 3-Cl | 5-(3-difluoromethyl)-isoxazole | 1 | 4-CN |
| A92 | 1 | 3-Cl | 5-(3-difluoromethyl)-isoxazole | 1 | 4-Cl |
| A93 | 1 | 6-F | 5-(3-difluoromethyl)-isoxazole | 2 | 3-F, 5-Cl |
| A94 | 1 | 6-Me | 5-(3-difluoromethyl)-isoxazole | 2 | 3-F, 5-Cl |
| A95 | 1 | 6-Cl | 5-(3-difluoromethyl)-isoxazole | 2 | 3-F, 5-Cl |
| A96 | 0 | — | 4-methoxypyrazol-1-yl | 2 | 3-F, 5-Cl |
| A97 | 0 | — | 4-(trifluoromethyl)thien-2-yl | 2 | 3-F, 5-Cl |
| A98 | 1 | 3-Br | 5-(3-difluoromethyl)-isoxazole | 1 | 6-F |
| A99 | 1 | 3-Br | 5-(3-difluoromethyl)-isoxazole | 1 | 4-CF₃ |
| A100 | 1 | 3-Br | 5-(3-difluoromethyl)-isoxazole | 1 | 5-Cl |
| A101 | 1 | 3-Br | 5-(3-difluoromethyl)-isoxazole | 2 | 3,5-di-F |
| A102 | 1 | 3-Br | 5-(3-difluoromethyl)-isoxazole | 1 | 5-CN |
| A103 | 1 | 3-Br | 5-(3-difluoromethyl)-isoxazole | 2 | 3-F, 5-Br |
| A104 | 1 | 3-Br | 5-(3-difluoromethyl)-isoxazole | 2 | 3-F, 5-CF₃ |
| A105 | 1 | 3-Br | 5-(3-difluoromethyl)-isoxazole | 2 | 3-CN, 5-Cl |
| A106 | 1 | 3-Br | 5-(3-difluoromethyl)-isoxazole | 1 | 5-Br |
| A107 | 1 | 3-Br | 5-(3-difluoromethyl)-isoxazole | 1 | 3-CN |
| A108 | 1 | 3-Cl | 5-(3-difluoromethyl)-isoxazole | 1 | 5-NO₂ |
| A109 | 1 | 3-Cl | 5-(3-difluoromethyl)-isoxazole | 2 | 3,5-di-Cl |
| A110 | 1 | 3-Cl | 5-(3-difluoromethyl)-isoxazole | 1 | 5-CF₃ |
| A111 | 1 | 3-Cl | 5-(3-difluoromethyl)-isoxazole | 1 | 6-F |
| A112 | 1 | 3-Cl | 5-(3-difluoromethyl)-isoxazole | 1 | 4-CF₃ |
| A113 | 1 | 3-Cl | 5-(3-difluoromethyl)-isoxazole | 1 | 5-Cl |
| A114 | 1 | 3-Cl | 5-(3-difluoromethyl)-isoxazole | 2 | 3,5-di-F |
| A115 | 1 | 3-Cl | 5-(3-difluoromethyl)-isoxazole | 1 | 5-CN |
| A116 | 1 | 3-Cl | 5-(3-difluoromethyl)-isoxazole | 2 | 3-F, 5-Br |
| A117 | 1 | 3-Cl | 5-(3-difluoromethyl)-isoxazole | 2 | 3-F, 5-CF₃ |
| A118 | 1 | 3-Cl | 5-(3-difluoromethyl)-isoxazole | 2 | 3-CN, 5-CF₃ |
| A119 | 1 | 3-Cl | 5-(3-difluoromethyl)-isoxazole | 1 | 5-Br |
| A120 | 1 | 3-Cl | 5-(3-difluoromethyl)-isoxazole | 1 | 3-CN |
| A121 | 0 | — | 3-(trifluoromethyl)pyrazole-1-yl | 2 | 3-F, 5-Cl |
| A122 | 0 | — | 5-(trifluoromethyl)pyrazole-1-yl | 2 | 3-F, 5-Cl |
| A123 | 0 | — | 3, 5-bis(trifluoromethyl)pyrazol-1-yl | 2 | 3-F, 5-Cl |
| A124 | 1 | 3-F | 5-(3-difluoromethyl)-isoxazole | 2 | 4-Cl, 5-CO₂Et |
| A126 | 0 | — | 5-(3-methyl-1,2,4-oxadiazole) | 2 | 3-F, 5-Cl |
| A128 | 0 | — | 3-(5-methyl-1,2,4-oxadiazole) | 2 | 3-F, 5-Cl |
| A129 | 0 | — | 2-(4-methyl-thiazole) | 2 | 3-F, 5-Cl |
| A130 | 0 | — | 2-(5-methyl-1,3,4-oxadiazole) | 2 | 3-F, 5-Cl |
| A131 | 0 | — | 4-(5-methyl-thiadiazole) | 2 | 3-F, 5-Cl |
| A132 | 0 | — | 2-(1,3,4-oxadiazole) | 2 | 3-F, 5-Cl |
| A137 | 1 | 3-F | 5-(3-difluoromethyl)-isoxazole | 2 | 3-CO₂Et, 6-Cl |
| A142 | 0 | — | 2-(5-difluoromethylsulfanyl)-1,3,4—thiadiazole | 2 | 3-F, 5-Cl |
| A143 | 0 | — | 3-methylimidazo-4-yl | 2 | 3-F, 5-Cl |
| A144 | 0 | — | 2-methylpyrazol-3-yl | 2 | 3-F, 5-Cl |
| A145 | 0 | — | 5-isothiazole | 2 | 3-F, 5-Cl |
| A146 | 0 | — | 5-thiazole | 2 | 3-F, 5-Cl |
| A147 | 0 | — | 2-thiazole | 2 | 3-F, 5-Cl |
| A148 | 0 | — | 3-furan | 2 | 3-F, 5-Cl |
| A149 | 0 | — | 2-furan | 2 | 3-F, 5-Cl |
| A154 | 1 | 3-F | 5-(3-difluoromethyl)-isoxazole | 2 | 5-CO₂Et, 6—Me |
| A156 | 1 | 3-F | 5-(3-difluoromethyl)-isoxazole | 2 | 4-CO₂Et, 6-Br |
| A158 | 1 | 3-CF₃ | 4-(trifluoromethyl)pyrazol-1-yl | 2 | 3-F, 5-Cl |
| A159 | 1 | 3-Cl | 4-(trifluoromethyl)pyrazol-1-yl | 2 | 3-F, 5-Cl |
| A160 | 1 | 3-CN | 5-(3-difluoromethyl)-isoxazole | 2 | 3,5-di-F |
| A161 | 1 | 3-CN | 5-(3-difluoromethyl)-isoxazole | 1 | 5-Cl |
| A162 | 1 | 3-CN | 5-(3-difluoromethyl)-isoxazole | 2 | 3-F, 5-Cl |
| A163 | 0 | — | 3-(5-difluoromethyl)-isoxazole | 2 | 3-F, 5-Cl |
| A167 | 0 | — | pyrazol-1-yl | 2 | 3-F, 5-Cl |
| A168 | 0 | — | (4-difluoromethyl)-triazol-2-yl | 2 | 3-F, 5-Cl |
| A169 | 0 | — | (4-difluoromethyl)-triazol-1-yl | 2 | 3-F, 5-Cl |
| A170 | 0 | — | 2(5-difluoromethyl)-oxazole | 2 | 3-F, 5-Cl |
| A171 | 1 | 4-Cl | thiazol-2-yl | 2 | 3-F, 5-Cl |

-continued
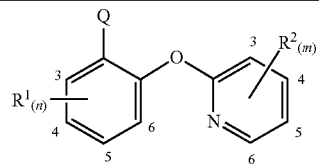
| Compound | n | R¹ | Q | m | R² |
|---|---|---|---|---|---|
| A172 | 1 | 3-F | 5-(3-difluoromethyl)-isoxazole | 2 | 5-Cl, 6-CN |
| A173 | 1 | 3-F | 5-(3-difluoromethyl)-isoxazole | 2 | 3-CN, 4-Cl |
| A174 | 1 | 3-F | thiazol-2-yl | 2 | 3-F, 5-Cl |
| A175 | 1 | 3-Br | thiazol-2-yl | 2 | 3-F, 5-Cl |
| A176 | 1 | 3-Cl | thiazol-2-yl | 2 | 3-F, 5-Cl |
* * * * *

UNITED STATES PATENT AND TRADEMARK OFFICE
CERTIFICATE OF CORRECTION

PATENT NO. : 12,227,495 B2  
APPLICATION NO. : 17/290869  
DATED : February 18, 2025  
INVENTOR(S) : Wailes et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 783 days.

Signed and Sealed this  
Twenty-second Day of July, 2025

Coke Morgan Stewart  
*Acting Director of the United States Patent and Trademark Office*